(12) United States Patent
Papish et al.

(10) Patent No.: US 11,773,040 B2
(45) Date of Patent: Oct. 3, 2023

(54) SELECTIVE HYDRODEOXYGENATION OF AROMATIC COMPOUNDS

(71) Applicants: The Board of Trustees of The University of Alabama, Tuscaloosa, AL (US); University of South Carolina, Columbia, SC (US)

(72) Inventors: Elizabeth Papish, Tuscaloosa, AL (US); Aaron Vannucci, Columbia, SC (US)

(73) Assignees: Board of Trustees of the University of Alabama, Tuscaloosa, AL (US); University of South Carolina, Columbia, SC (US)

( * ) Notice: Subject to any disclaimer, the term of this patent is extended or adjusted under 35 U.S.C. 154(b) by 171 days.

(21) Appl. No.: 17/060,455

(22) Filed: Oct. 1, 2020

(65) Prior Publication Data

US 2021/0198171 A1    Jul. 1, 2021

Related U.S. Application Data

(60) Provisional application No. 62/955,067, filed on Dec. 30, 2019.

(51) Int. Cl.
| | | |
|---|---|---|
| *C07C 1/20* | (2006.01) | |
| *B01J 31/18* | (2006.01) | |
| *C07C 41/18* | (2006.01) | |
| *B01J 31/22* | (2006.01) | |

(52) U.S. Cl.
CPC ............ *C07C 41/18* (2013.01); *B01J 31/181* (2013.01); *B01J 31/1815* (2013.01); *B01J 31/2295* (2013.01); *C07C 1/20* (2013.01); *B01J 2531/821* (2013.01); *C07C 2601/16* (2017.05)

(58) Field of Classification Search
None
See application file for complete search history.

(56) References Cited

U.S. PATENT DOCUMENTS

2019/0083966 A1    3/2019 Papish et al.
2021/0053042 A1*   2/2021 Lin ...................... C07D 307/20

OTHER PUBLICATIONS

Lien, C-H. et al. "Promotion of Activity and Selectivity by Alkanethiol Monolayers for Pd-Catalyzed Benzyl Alcohol Hydrodeoxygenation" J. Phys. Chem. C 2014, 118, 23783-23789 (Year: 2014).*

US Energy Information Administration. International Energy Outlook 2017. 76 pages. Available on-line at: https://www.eia.gov/outlooks/ieo/pdf/0484(2017).pdf (accessed Sep. 11, 2019).

Renewable Energy Policy Network for 21st Century Renewables 2014. Global Status Report. 216 pages. Available on-line at: https://www.ren21.net/wp-content/uploads/2019/05/GSR2014_Full-Report_English.pdf (accessed Sep. 11, 2019).

(Continued)

*Primary Examiner* — Medhanit W Bahta
(74) *Attorney, Agent, or Firm* — Meunier Carlin & Curfman LLC

(57) ABSTRACT

Disclosed are methods of selective hydrodeoxygenation of aromatic compounds by using catalyst systems comprising N-heterocyclic carbene (NHC) and 4-pyridinol-derived pincer ligands and metal complexes containing these ligands.

10 Claims, 2 Drawing Sheets

(56) References Cited

OTHER PUBLICATIONS

Bridgwater, A. V., Renewable fuels and chemicals by thermal processing of biomass. Chem. Eng. J. 2003, 91 (2), 87-102. https://doi.org/10.1016/S1385-8947(02)00142-0.

Raymundo, L. M.; Mullen, C. A.; Strahan, G. D.; Boateng, A. A.; Trierweiler, J. O., Deoxygenation of Biomass Pyrolysis Vapors via in Situ and ex Situ Thermal and Biochar Promoted Upgrading. Energy Fuels 2019, 33 (3), 2197-2207. 10.1021/acs.energyfuels.8b03281.

Rahimi, A.; Ulbrich, A.; Coon, J. J.; Stahl, S. S., Formic-acid-induced depolymerization of oxidized lignin to aromatics. Nature 2014, 515, 249. 10.1038/nature13867.

Huang, X.; Atay, C.; Korányi, T. I.; Boot, M. D.; Hensen, E. J. M., Role of Cu—Mg—Al Mixed Oxide Catalysts in Lignin Depolymerization in Supercritical Ethanol. ACS Catal. 2015, 5 (12), 7359-7370. 10.1021/acscatal.5b02230.

Gasser, C. A.; Čvančarová, M.; Ammann, E. M.; Schäffer, A.; Shahgaldian, P.; Corvini, P. F.-X., Sequential lignin depolymerization by combination of biocatalytic and formic acid/formate treatment steps. Appl. Microbiol. Biotechnol. 2017, 101 (6), 2575-2588. 10.1007/s00253-016-8015-5.

Partenheimer, W., The Aerobic Oxidative Cleavage of Lignin to Produce Hydroxyaromatic Benzaldehydes and Carboxylic Acids via Metal/Bromide Catalysts in Acetic Acid/Water Mixtures. Adv. Synth. Catal. 2009, 351 (3), 456-466. 10.1002/adsc.200800614.

Renders, T.; Van den Bosch, S.; Koelewijn, S. F.; Schutyser, W.; Sels, B. F., Lignin-first biomass fractionation: the advent of active stabilisation strategies. Energy Environ. Sci. 2017, 10 (7), 1551-1557. 10.1039/C7EE01298E.

Das, A.; Rahimi, A.; Ulbrich, A.; Alherech, M.; Motagamwala, A. H.; Bhalla, A.; da Costa Sousa, L.; Balan, V.; Dumesic, J. A.; Hegg, E. L.; Dale, B. E.; Ralph, J.; Coon, J. J.; Stahl, S. S., Lignin Conversion to Low-Molecular-Weight Aromatics via an Aerobic Oxidation-Hydrolysis Sequence: Comparison of Different Lignin Sources. ACS Sustainable Chemistry & Engineering 2018, 6 (3), 3367-3374. 10.1021/acssuschemeng.7b03541.

Gollakota, A. R. K.; Reddy, M.; Subramanyam, M. D.; Kishore, N., A review on the upgradation techniques of pyrolysis oil. Renewable and Sustainable Energy Reviews 2016, 58 (C), 1543-1568. 10.1016/j.rser.2015.12.180.

Luo, H.; Abu-Omar, M. M., Lignin extraction and catalytic upgrading from genetically modified poplar. Green Chem. 2018, 20 (3), 745-753. 10.1039/C7GC03417B.

Nolte, M. W.; Shanks, B. H., A Perspective on Catalytic Strategies for Deoxygenation in Biomass Pyrolysis. Energy Technology 2017, 5 (1), 7-18. 10.1002/ente.201600096.

Zakzeski, J.; Bruijnincx, P. C. A.; Jongerius, A. L.; Weckhuysen, B. M., The Catalytic Valorization of Lignin for the Production of Renewable Chemicals. Chem. Rev. 2010, 110 (6), 3552-3599. 10.1021/cr900354u.

Shao, Y.; Xia, Q.; Dong, L.; Liu, X.; Han, X.; Parker, S. F.; Cheng, Y.; Daemen, L. L.; Ramirez-Cuesta, A. J.; Yang, S.; Wang, Y., Selective production of arenes via direct lignin upgrading over a niobium-based catalyst. Nat. Commun. 2017, 8 (1), 16104. 10.1038/ncomms16104.

Guo, T.; Xia, Q.; Shao, Y.; Liu, X.; Wang, Y., Direct deoxygenation of lignin model compounds into aromatic hydrocarbons through hydrogen transfer reaction. Applied Catalysis A: General 2017, 547, 30-36. https://doi.org/10.1016/j.apcata.2017.07.050.

Baddour, F. G.; Witte, V. A.; Nash, C. P.; Griffin, M. B.; Ruddy, D. A.; Schaidle, J. A., Late-Transition Metal-Modified β-Mo2C Catalysts for Enhanced Hydrogenation during Guaiacol Deoxygenation. ACS Sustainable Chemistry & Engineering 2017, 5 (12), 11433-11439. 10.1021/acssuschemeng.7b02544.

Hsu, P.-J.; Jiang, J.-W.; Lin, Y.-C., Does a Strong Oxophilic Promoter Enhance Direct Deoxygenation? A Study of NiFe, NiMo, and NiW Catalysts in p-Cresol Conversion. ACS Sustainable Chemistry & Engineering 2018, 6 (1), 660-667. 10.1021/acssuschemeng.7b03010.

Ju, C.; Li, M.; Fang, Y.; Tan, T., Efficient hydro-deoxygenation of lignin derived phenolic compounds over bifunctional catalysts with optimized acid/metal interactions. Green Chem. 2018, 20 (19), 4492-4499. 10.1039/C8GC01960F.

Song, W.; Zhou, S.; Hu, S.; Lai, W.; Lian, Y.; Wang, J.; Yang, W.; Wang, M.; Wang, P.; Jiang, X., Surface Engineering of CoMoS Nanosulfide for Hydrodeoxygenation of Lignin-Derived Phenols to Arenes. ACS Catal. 2019, 9 (1), 259-268. 10.1021/acscatal.8b03402.

Hao, P.; Schwartz, D. K.; Medlin, J. W., Effect of Surface Hydrophobicity of Pd/Al2O3 on Vanillin Hydrodeoxygenation in a Water/Oil System. ACS Catal. 2018, 8 (12), 11165-11173. 10.1021/acscatal.8b03141.

Lien, C.-H.; Medlin, J. W., Promotion of Activity and Selectivity by Alkanethiol Monolayers for Pd-Catalyzed Benzyl Alcohol Hydrodeoxygenation. The Journal of Physical Chemistry C 2014, 118 (41), 23783-23789. 10.1021/jp507114g.

Parsell, T. H.; Owen, B. C.; Klein, I.; Jarrell, T. M.; Marcum, C. L.; Haupert, L. J.; Amundson, L. M.; Kenttämaa, H. I.; Ribeiro, F.; Miller, J. T.; Abu-Omar, M. M., Cleavage and hydrodeoxygenation (HDO) of C—O bonds relevant to lignin conversion using Pd/Zn synergistic catalysis. Chem. Sci. 2013, 4 (2), 806-813. 10.1039/C2SC21657D.

Liu, H.; Jiang, T.; Han, B.; Liang, S.; Zhou, Y., Selective Phenol Hydrogenation to Cyclohexanone Over a Dual Supported Pd-Lewis Acid Catalyst. Science 2009, 326, 1250-1252.

DeLucia, N. A.; Das, N.; Overa, S.; Paul, A.; Vannucci, A. K., Low temperature selective hydrodeoxygenation of model lignin monomers from a homogeneous palladium catalyst. Catal. Today 2018, 302, 146-150. https://doi.org/10.1016/j.cattod.2017.05.050.

DeLucia, N. A.; Jystad, A.; Laan, K. V.; Tengco, J. M. M.; Caricato, M.; Vannucci, A. K., Silica Supported Molecular Palladium Catalyst for Selective Hydrodeoxygenation of Aromatic Compounds under Mild Conditions. ACS Catal. 2019, 9060-9071. 10.1021/acscatal.9b02460.

Rodrigues, R. R.; Boudreaux, C. M.; Papish, E. T.; Delcamp, J. H., Photocatalytic Reduction of CO2 to CO and Formate: Do Reaction Conditions or Ruthenium Catalysts Control Product Selectivity? ACS Appl. Energy Mater. 2019, 2, 37-46. 10.1021/acsaem.8b01560.

Das, S.; Rodrigues, R. R.; Lamb, R. W.; Qu, F.; Reinheimer, E.; Boudreaux, C. M.; Webster, C. E.; Delcamp, J. H.; Papish, E. T., Highly Active Ruthenium CNC Pincer Photocatalysts for Visible-Light-Driven Carbon Dioxide Reduction. Inorg. Chem. 2019, 58 (12), 8012-8020. 10.1021/acs.inorgchem.9b00791.

Boudreaux, C. M.; Liyanage, N. P.; Shirley, H.; Siek, S.; Gerlach, D. L.; Qu, F.; Delcamp, J. H.; Papish, E. T., Ruthenium(II) complexes of pyridinol and N-heterocyclic carbene derived pincers as robust catalysts for selective carbon dioxide reduction. Chem. Commun. 2017, 53, 11217-11220. 10.1039/C7CC05706G.

Burks, D. B.; Davis, S.; Lamb, R. W.; Liu, X.; Rodrigues, R. R.; Liyanage, N. P.; Sun, Y.; Webster, C. E.; Delcamp, J. H.; Papish, E. T., Nickel(II) pincer complexes demonstrate that the remote substituent controls catalytic carbon dioxide reduction. Chem. Commun. 2018, 54, 3819-3822. 10.1039/C7CC09507D.

Gradert, C.; Krahmer, J.; Sönnichsen, F. D.; Näther, C.; Tuczek, F., Molybdenum(0)-carbonyl complexes supported by mixed benzimidazol-2-ylidene/phosphine ligands: Influence of benzannulation on the donor properties of the NHC groups. J. Organomet. Chem. 2014, 770, 61-68. https://doi.org/10.1016/j.jorganchem.2014.08.010.

Jeffrey, G. A. Hydrogen-Bonding: An update. Crystallogr. Rev. 2003, 9 (2), 135-176.

Kaljurand, I.; Ku ̈tt, A.; Soova ̈li, L.; Rodima, T.; Ma ̈emets, V.; Leito, I.; Koppel, I. A. Extension of the Self-Consistent Spectrophotometric Basicity Scale in Acetonitrile to a Full Span of 28 p KaUnits: Unification of Different Basicity Scales. J. Org. Chem. 2005, 70 (3), 1019-1028.

Yang, S.; Tang, W.; Yang, Z.; Xu, J. Iridium-Catalyzed Highly Efficient and Site-Selective Deoxygenation of Alcohols. ACS Catal. 2018, 8 (10), 9320-9326.

(56) References Cited

OTHER PUBLICATIONS

Anton, D. R.; Crabtree, R. H., Dibenzo[a,e]cyclooctatetraene in a proposed test for heterogeneity in catalysts formed from soluble platinum-group metal complexes. Organometallics 1983, 2 (7), 855-859. 10.1021/om50001a013.

Widegren, J. A.; Bennett, M. A.; Finke, R. G., Is It Homogeneous or Heterogeneous Catalysis? Identification of Bulk Ruthenium Metal as the True Catalyst in Benzene Hydrogenations Starting with the Monometallic Precursor, Ru(II)(η6-C6Me6)(OAc)2, Plus Kinetic Characterization of the Heterogeneous Nucleation, Then Autocatalytic Surface-Growth Mechanism of Metal Film Formation. J. Am. Chem. Soc. 2003, 125 (34), 10301-10310. 10.1021/ja021436c.

Eberhard, M. R., Insights into the Heck Reaction with PCP Pincer Palladium(II) Complexes. Org. Lett. 2004, 6 (13), 2125-2128. 10.1021/ol049430a.

Stracke, J. J.; Finke, R. G., Water Oxidation Catalysis Beginning with 2.5 μ M [Co4(H 2O) 2(PW 9O 34) 2] 10—: Investigation of the True Electrochemically Driven Catalyst at ≥600 mV Overpotential at a Glassy Carbon Electrode. ACS Catal. 2013, 1209-1219. 10.1021/cs400141t.

Bayram, E.; Linehan, J. C.; Fulton, J. L.; Roberts, J. A. S.; Szymczak, N. K.; Smurthwaite, T. D.; Özkar, S.; Balasubramanian, M.; Finke, R. G., Is It Homogeneous or Heterogeneous Catalysis Derived from [RhCp*Cl2]2? In Operando XAFS, Kinetic, and Crucial Kinetic Poisoning Evidence for Subnanometer Rh4 Cluster-Based Benzene Hydrogenation Catalysis. J. Am. Chem. Soc. 2011, 133 (46), 18889-18902. 10.1021/ja2073438.

Moore, Eric J., Jeffrey M. Sullivan, and Jack R. Norton. Kinetic and thermodynamic acidity of hydrido transition-metal complexes. 3. Thermodynamic acidity of common mononuclear carbonyl hydrides. Journal of the American Chemical Society 108.9 (1986): 2257-2263.

Papish, E. T.; Magee, M. P.; Norton, J. R., Protonation of transition metal hydrides to give dihydrogen complexes. Mechanistic implications and catalytic applications. In Recent Advances in Hydride Chemistry; Elsevier: 2001; pp. 39-74.

Cho, Daeheum, Kyoung Chui Ko, and Jin Yong Lee. "Catalytic mechanism for the ruthenium-complex-catalyzed synthesis of amides from alcohols and amines: a DFT study." Organometallics 32.16 (2013): 4571-4576.

Hull, J. F.; Himeda, Y.; Wang, W.-H.; Hashiguchi, B.; Periana, R.; Szalda, D. J.; Muckerman, J. T.; Fujita, E. Reversible hydrogen storage using CO2 and a proton-switchable iridium catalyst in aqueous media under mild temperatures and pressures. Nat. Chem. 2012, 4 (5), 383-388.

Wang, W.-H.; Hull, J. F.; Muckerman, J. T.; Fujita, E.; Himeda, Y. Second-Coordination-Sphere and Electronic Effects Enhance Iridium(III)-Catalyzed Homogeneous Hydrogenation of Carbon Dioxide in Water Near Ambient Temperature and Pressure. Energy Environ. Sci. 2012, 5 (7), 7923-7926.

Himeda, Y.; Onozawa-Komatsuzaki, N.; Sugihara, H.; Kasuga, K. Simultaneous Tuning of Activity and Water Solubility of Complex Catalysts by Acid-Base Equilibrium of Ligands for Conversion of Carbon Dioxide. Organometallics 2007, 26 (3), 702-712.

Himeda, Y. Conversion of CO2 into Formate by Homogeneously Ctalyzed Hydrogenation in Water: Tuning Catalytic Activity and Water Solubility through the Acid-Base Equilibrium of the Ligand. Eur. J. Inorg. Chem. 2007, 2007 (25), 3927-3941.

Sandhya, K. S.; Remya, G. S.; Suresh, C. H. Pincer Ligand Modifications to Tune the Activation Barrier for H2 Elimination in Water Splitting Milstein Catalyst. Inorg. Chem. 2015, 54 (23), 11150-11156.

Crabtree, R. Iridium compounds in catalysis. Acc. Chem. Res. 1979, 12 (9), 331-337.

Gottlieb, H. E.; Kotlyar, V.; Nudelman, A., NMR Chemical Shifts of Common Laboratory Solvents as Trace Impurities. J. Org. Chem. 1997, 62, 7512-7515.

Yao, Wenzhi, et al. "Determining the Catalyst Properties That Lead to High Activity and Selectivity for Catalytic Hydrodeoxygenation with Ruthenium Pincer Complexes." Organometallics 39.5 (2020): 662-669.

Sheldrick, G. M., A short history of SHELX. Acta Cryst. A 2008, 64, 112-122.

Sheldrick, G. M., Crystal structure refinement with SHELXL. Acta Cryst. 2015, A71, 3-8.

Sheldrick, G., SHELXT—Integrated space-group and crystal-structure determination. Acta Crystallographica Section A 2015, 71 (1), 3-8.

Hübschle, C. B.; Sheldrick, G. M.; Dittrich, B., ShelXle: a Qt graphical user interface for SHELXL. J. Appl. Cryst. 2011, 44, 1281-1284.

Dolomanov, O. V.; Bourhis, L. J.; Gildea, R. J.; Howard, J. A. K.; Puschmann, H., OLEX2: a complete structure solution, refinement and analysis program. J. Appl. Crystallogr. 2009, 42, 339-341.

Schlosser, M.; Bobbio, C.; Rausis, T., Regiochemically Flexible Substitutions of Di-, Tri-, and Tetrahalopyridines: The Trialkylsilyl Trick. J. Org. Chem. 2005, 70, 2494-2502.

Maleczka, R. E.; Shi, F.; Holmes, D.; Smith, M. R., C—H Activation/Borylation/Oxidation: A One-Pot Unified Route to Meta-Substituted Phenols Bearing Ortho-/Para-Directing Groups. J. Am. Chem. Soc. 2003, 125, 7792-7793.

Herbst, A.; Bronner, C.; Dechambenoit, P.; Wenger, O. S., Gold Complexes with Tridentate Cyclometalating and NHC Ligands: A Search for New Photoluminescent Gold(III) Compounds. Organometallics 2013, 32, 1807-1814.

Karak, P.; Dutta, C.; Dutta, T.; Koner, A. L.; Choudhury, J., Orchestrated catalytic double rollover annulation: rapid access to N-enriched cationic and neutral PAHs. Chem. Commun. 2019, 55, 6791-6794.

Berge, et al., Pharmaceutical Salts, Journal of Pharmaceutical Science, 66, 2 (1977).

Danopoulos, Andreas A., et al. "Structural and reactivity studies of "pincer" pyridine dicarbene complexes of Fe0: Experimental and computational comparison of the phosphine and NHC donors." Chemistry—A European Journal 15.22 (2009): 5491-5502.

* cited by examiner

SELECTIVE HYDRODEOXYGENATION OF AROMATIC COMPOUNDS

CROSS-REFERENCE TO RELATED APPLICATIONS

This application claims the benefit of U.S. Provisional Application No. 62/955,067, filed Dec. 30, 2019, the content of which is incorporated herein by reference in its entirety.

STATEMENT ACKNOWLEDGING GOVERNMENT SUPPORT

This invention was made with government support under Grant No. CHE-1800214, Grant No. OIA-1539035, and Grant No. OIA-15939105, all awarded by the National Science Foundation. The government has certain rights in the invention.

BACKGROUND

Total world energy consumption was 575 quadrillion Btu in 2015, and it is predicted to increase by 285 to 736 quadrillion Btu in 2040 (US Energy_Information_Administration International Energy Outlook 2017). In addition, renewable fuels are predicted to be the world's fastest-growing energy source, with consumption increasing by an average of 2.3% per year between 2015 and 2040. Renewables contributed 19% to the total energy consumption in 2012 (Renewable_Energy_Policy_Network_for_21st_Century Renewables 2014 Global Status Report).

The largest fraction of renewables is traditional biomass, which contributes around 9% of the total energy consumption. To convert biomass to a more useful energy form, there are three main thermal processes available, namely pyrolysis, gasification and combustion (Bridgwater, A. V., Renewable fuels and chemicals by thermal processing of biomass. Chem. Eng. J. 2003, 91(2), 87-102). The main product from the pyrolysis of biomass is bio-oil. Bio-oil has problems of thermal instability, affinity for water, corrosivity, high viscosity, and low heating values due to its high oxygen content (Raymundo, L. M., et al., Deoxygenation of Biomass Pyrolysis Vapors via in Situ and ex Situ Thermal and Biochar Promoted Upgrading. Energy Fuels 2019, 33 (3), 2197-2207).

To expand the utility of the bio-oil, selective deoxygenation can be applied to reduce oxygen from the compounds. Furthermore, recent advances in biomass processing and lignin depolymerization have led to a greatly increased need for catalysts capable of selective deoxygenation of aromatic alcohols (Rahimi, A. et al., Nature 2014, 515, 249; Huang, X., et al., ACS Catal. 2015, 5 (12), 7359-7370; Gasser, C. A., et al., Appl. Microbiol. Biotechnol. 2017, 101 (6), 2575-2588; Partenheimer, W., Adv. Synth. Catal. 2009, 351 (3), 456-466.; Renders, T., et al., Energy Environ. Sci. 2017, 10 (7), 1551-1557; Das, A., et al., ACS Sustainable Chemistry & Engineering 2018, 6 (3), 3367-3374).

Deoxygenation of the aromatic alcohols would increase the energy density of the resulting liquid fuel (Gollakota, A. R. K., et al., Renewable and Sustainable Energy Reviews 2016, 58 (C), 1543-1568) and/or lead to the isolation of important industrial chemical feedstocks (Luo, H., et al., Green Chem. 2018, 20 (3), 745-753). Selectively deoxygenating lignin derived compounds without hydrogenation of the aromatic units is of specific interest because aromatics and alkenes are higher value chemicals compared to alkanes, hydrogen use efficiency would be maximized, and carbon loss would be minimized (Nolte, M. W., et al., Energy Technology 2017, 5 (1), 7-18).

Traditional nanoparticle based heterogeneous catalysts can achieve upwards of 80-90% selectivity for the hydrodeoxygenation of model compounds (Zakzeski, J., et al., Chem. Rev. 2010, 110 (6), 3552-3599; Shao, Y.; et al., Nat. Commun. 2017, 8 (1), 16104; Guo, T.; et al., Applied Catalysis A: General 2017, 547, 30-36; Baddour, F. G.; et al., ACS Sustainable Chemistry & Engineering 2017, 5 (12), 11433-11439; Hsu, P.-J.; et al., ACS Sustainable Chemistry & Engineering 2018, 6 (1), 660-667; Ju, C.; et al., Green Chem. 2018, 20 (19), 4492-4499; Song, W.; et al., ACS Catal. 2019, 9 (1), 259-268). Of these model compounds, vanillyl alcohol has been previously studied as a commonly derived chemical from lignin depolymerization. Heterogeneous Pd nanoparticle catalysts have exhibited good product selectivity for the formation of creosol depending on the reaction additives as shown in Scheme 1 below (Hao, P.; et al., ACS Catal. 2018, 8 (12), 11165-11173; Lien, C.-H., et al., The Journal of Physical Chemistry C 2014, 118 (41), 23783-23789; Parsell, T. H.; et al., Chem. Sci. 2013, 4 (2), 806-813):

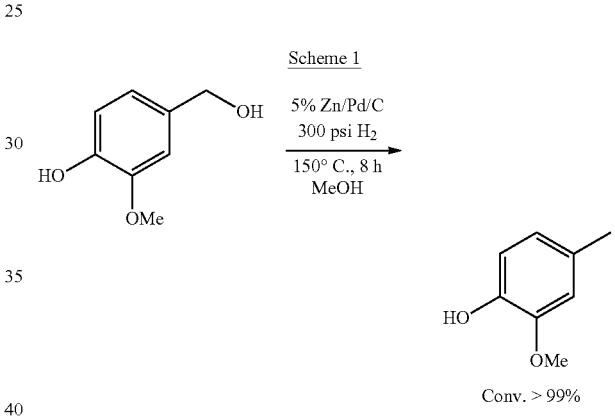

Molecular catalysts have also been examined for catalytic hydrodeoxygenation (HDO) of benzylic alcohols due to the fact that molecular catalysts lack extended metallic surfaces and thus can avoid unwanted ring hydrogenation products (Liu, H.; et al., Science 2009, 326, 1250-1252). A molecular palladium catalyst in homogeneous methanol solution has exhibited complete selectivity for HDO over ring hydrogenation for benzylic substrates (DeLucia, N. A.; et al., Catal. Today 2018, 302, 146-150), and a molecular catalyst attached to the surface of oxide particles has exhibited high selectivity and activity towards the formation of cresol from vanillyl alcohol and vanillin (DeLucia, N. A., et al., ACS Catal. 2019, 9060-9071).

Given the importance of producing highly efficient bio-oils, new methods and new catalysts with improved selectivity, activity, and durability are needed. Also are needed new methods and catalysts for efficient and selective hydrodeoxygenation of aromatic molecules. These needs and other needs are at least partially satisfied by the present disclosure.

SUMMARY

In accordance with the purposes of the disclosed materials and methods, as embodied and broadly described herein, the disclosed subject matter, in one aspect, relates to compounds, compositions and methods of making and using compounds and compositions.

In some aspects, disclosed herein is a method comprising: selectively deoxygenating at least one oxygenated aromatic compound in the presence of a hydrogen gas and a catalyst system to form a reaction product, wherein the catalyst system comprises a catalyst of formula (I):

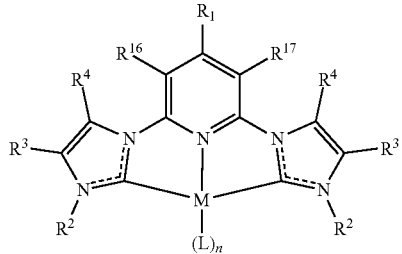

(I)

wherein,
R$^1$ is hydrogen, OH, O$^-$, halogen, amine, C$_1$-C$_{10}$ alkyl, C$_1$-C$_{10}$ alkoxy, C$_2$-C$_{10}$ alkenyl, C$_2$-C$_{10}$ alkynyl, C$_6$-C$_{14}$ aryl, C$_1$-C$_{13}$ heteroaryl, C$_6$-C$_{14}$ aryloxy, C$_3$-C$_{10}$ cycloalkyl, or C$_3$-C$_{10}$ cycloalkenyl, wherein R$^1$ is optionally substituted with C$_1$-C$_{10}$ alkyl, C$_1$-C$_{10}$ alkoxy, C$_2$-C$_{10}$ alkenyl, C$_2$-C$_{10}$ alkynyl, C$_6$-C$_{14}$ aryl, C$_1$-C$_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl;

each R$^2$ is, independent of the other, C$_1$-C$_{10}$ alkyl, C$_2$-C$_{10}$ alkenyl, C$_2$-C$_{10}$ alkynyl, C$_6$-C$_{14}$ aryl, or C$_1$-C$_{13}$ heteroaryl, wherein R$^2$ is optionally substituted with C$_1$-C$_{10}$ alkyl, C$_1$-C$_{10}$ alkoxy, C$_2$-C$_{10}$ alkenyl, C$_2$-C$_{10}$ alkynyl, C$_6$-C$_{14}$ aryl, C$_1$-C$_{13}$ heteroaryl, aldehyde, amino, carboxylic acid, ester, ether, halide, hydroxy, ketone, nitro, cyano, silyl, sulfo-oxo, sulfonyl, sulfone, sulfoxide, or thiol;

each R$^3$ and R$^4$ are, independent of the other, hydrogen, C$_1$-C$_{10}$ alkyl, C$_2$-C$_{10}$ alkenyl, C$_2$-C$_{10}$ alkynyl, C$_6$-C$_{14}$ aryl, or C$_1$-C$_{13}$ heteroaryl, wherein R$^3$ and R$^4$ are optionally substituted with C$_1$-C$_{10}$ alkyl, C$_1$-C$_{10}$ alkoxy, C$_2$-C$_{10}$ alkenyl, C$_2$-C$_{10}$ alkynyl, C$_6$-C$_{14}$ aryl, C$_1$-C$_{13}$ heteroaryl, aldehyde, amino, carboxylic acid, ester, ether, halide, hydroxy, ketone, nitro, cyano, silyl, sulfo-oxo, sulfonyl, sulfone, sulfoxide, or thiol, or R$^3$ and R$^4$ combine together with the atoms to which they are attached to form a cycloalkyl, cyclohetroaryl, aryl, or heteroaryl;

each R$^{16}$ and R$^{17}$ are, independent of the other, hydrogen, OH, O$^-$, halogen, amine, C$_1$-C$_{10}$ alkyl, C$_1$-C$_{10}$ alkoxy, C$_2$-C$_{10}$ alkenyl, C$_2$-C$_{10}$ alkynyl, C$_6$-C$_{14}$ aryl, C$_1$-C$_{13}$ heteroaryl, C$_6$-C$_{14}$ aryloxy, C$_3$-C$_{10}$ cycloalkyl, or C$_3$-C$_{10}$ cycloalkenyl, wherein each R$^{16}$ and R$^{15}$, independent of the other, is optionally substituted with C$_1$-C$_{10}$ alkyl, C$_1$-C$_{10}$ alkoxy, C$_2$-C$_{10}$ alkenyl, C$_2$-C$_{10}$ alkynyl, C$_6$-C$_{14}$ aryl, C$_1$-C$_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl M is Ru or Ir;
each L is independently selected from Cl, Br, CH$_3$CN, DMF, H$_2$O, bipyridine, phenylpyridine, CO$_2$, and a CNC-pincer ligand; and
n is 1, 2, or 3.

Still, in further aspects, the aromatic compound having at least one hydroxyl group of the disclosed methods has a formula (II):

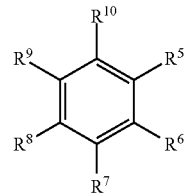

(II)

wherein,
R$^5$ is independently selected from hydrogen, substituted or unsubstituted C$_1$-C$_6$-alkyl; R$^{11}$—OH, —OR$^{12}$, R$^{18}$OR$^{19}$, R$^{20}$COR$^{21}$, substituted or unsubstituted C$_3$-C$_{10}$ cycloalkyls and heteroalkyls, C$_2$-C$_{10}$ alkenyl, and Ar';
R$^6$ is independently selected from hydrogen, hydrogen, substituted or unsubstituted R$^{11}$—OH; —OR$^{12}$, R$^{18}$OR$^{19}$, R$^{20}$COR$^{21}$, substituted or unsubstituted C$_3$-C$_{10}$ cycloalkyls and heteroalkyls, C$_2$-C$_{10}$ alkenyl, and Ar';
R$^7$ is independently selected from hydrogen, substituted or unsubstituted C$_1$-C$_6$-alkyl, R$^{11}$—OH, —OR$^{12}$, R$^{18}$OR$^{19}$, R$^{20}$COR$^{21}$, substituted or unsubstituted C$_3$-C$_{10}$ cycloalkyls and heteroalkyls, C$_2$-C$_{10}$ alkenyl, and Ar';
R$^8$ is independently selected from hydrogen, substituted or unsubstituted C$_1$-C$_6$-alkyl, R$^{11}$—OH; —OR$^{12}$, R$^{18}$OR$^{19}$, R$^{20}$COR$^{21}$, substituted or unsubstituted C$_3$-C$_{10}$ cycloalkyls and heteroalkyls, C$_2$-C$_{10}$ alkenyl, and Ar';
R$^9$ is independently selected from hydrogen, substituted or unsubstituted C$_1$-C$_6$-alkyl, R$^{11}$—OH; —OR$^{12}$, R$^{18}$OR$^{19}$, R$^{20}$COR$^{21}$, substituted or unsubstituted C$_3$-C$_{10}$ cycloalkyls and heteroalkyls, C$_2$-C$_{10}$ alkenyl, and Ar';
R$^{10}$ is independently selected from hydrogen, substituted or unsubstituted C$_1$-C$_6$-alkyl; R$^{11}$—OH; —OR$^{12}$, R$^{18}$OR$^{19}$, R$^{20}$COR$^{21}$, substituted or unsubstituted C$_3$-C$_{10}$ cycloalkyls and heteroalkyls, C$_2$-C$_{10}$ alkenyl, and Ar';
wherein when R$^6$, R$^7$, R$^9$, and R$^{10}$ are all hydrogen, R$^5$ is R$^{11}$—OH, R$^{18}$OR$^{19}$, or R$^{20}$COR$^{21}$,
wherein R$^{11}$ is a bond, substituted or unsubstituted C$_1$-C$_6$ alkyl, C$_2$-C$_{10}$ alkenyl, or Ar";
R$^{12}$ is independently selected from hydrogen, substituted or unsubstituted C$_1$-C$_6$ alkyl, C$_2$-C$_{10}$ alkenyl, and Ar",
R$^{18}$ is independently selected from substituted or unsubstituted C$_1$-C$_6$-alkyl, substituted or unsubstituted C$_3$-C$_{10}$ cycloalkyls and heteroalkyls, C$_2$-C$_{10}$ alkenyl, and Ar';
R$^{19}$ is independently selected from substituted or unsubstituted C$_1$-C$_6$-alkyl, substituted or unsubstituted C$_3$-C$_{10}$ cycloalkyls and heteroalkyls, C$_2$-C$_{10}$ alkenyl, and Ar';
R$^{20}$ is independently selected from a bond, substituted or unsubstituted C$_1$-C$_6$-alkyl, substituted or unsubstituted C$_3$-C$_{10}$ cycloalkyls and heteroalkyls, C$_2$-C$_{10}$ alkenyl, and Ar';
R$^{21}$ is independently selected from hydrogen, hydroxyl, C$_1$-C$_{10}$ alkyl, C$_1$-C$_{10}$ alkoxy, C$_2$-C$_{10}$ alkenyl, C$_2$-C$_{10}$ alkynyl, C$_6$-C$_{14}$ aryl, C$_1$-C$_{13}$ heteroaryl, C$_6$-C$_{14}$ aryloxy, C$_3$-C$_{10}$ cycloalkyl, or C$_3$-C$_{10}$ cycloalkenyl and Ar', wherein R$^{21}$ is optionally substituted with C$_1$-C$_{10}$ alkyl, C$_1$-C$_{10}$ alkoxy, C$_2$-C$_{10}$ alkenyl, C$_2$-C$_{10}$ alkynyl, C$_6$-C$_{14}$ aryl, C$_1$-C$_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl;

Ar' is a C$_6$-C$_{14}$ aryl or heteroaryl group optionally substituted with 1, 2, or 3 optional substituents; and
Ar" is a C$_6$-C$_{14}$ aryl or heteroaryl group optionally substituted with 1, 2, or 3 optional substituents;
Ar'" is a C$_6$-C$_{14}$ aryl or heteroaryl group optionally substituted with 1, 2, or 3 optional substituents;
wherein Ar', Ar", or Ar'", are the same or different.

In still further aspects, the reaction product formed according to the disclosed methods comprises a compound A of formula (III)

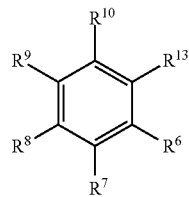
(III)

wherein $R^{13}$ is $R^{11}$—H.

In yet according to other aspects of the disclosure, the reaction product formed according to the disclosed methods can also comprise a compound B of formula (IV):

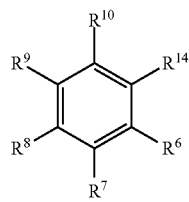
(IV)

wherein $R^{14}$ is —$OR^{15}$, wherein $R_{15}$ is a $C_1$-$C_{10}$ alkyl group.

In still further aspects and as disclosed herein, the compound A is selectively formed over the compound B.

Also disclosed herein is a catalyst of formula (I):

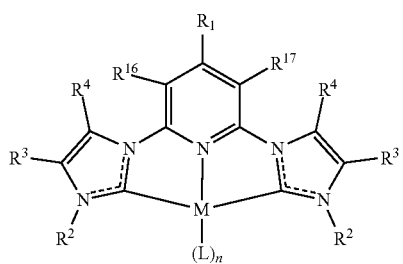
(I)

wherein, $R^1$ is hydrogen, OH, O$^-$, halogen, amine, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, $C_6$-$C_{14}$ aryloxy, $C_3$-$C_{10}$ cycloalkyl, or $C_3$-$C_{10}$ cycloalkenyl, wherein $R^1$ is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl;

each $R^2$ is, independent of the other, $C_1$-$C_{10}$ alkyl, $C_2$-$C_{10}$ alkenyl, $C_2$-$C_{10}$ alkynyl, $C_6$-$C_{14}$ aryl, or $C_1$-$C_{13}$ heteroaryl, wherein $R^2$ is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, or thiol;

each $R^3$ and $R^4$ are, independent of the other, hydrogen, $C_1$-$C_{10}$ alkyl, $C_2$-$C_{10}$ alkenyl, $C_2$-$C_{10}$ alkynyl, $C_6$-$C_{14}$ aryl, or $C_1$-$C_{13}$ heteroaryl, wherein $R^3$ and $R^4$ are optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, or thiol, or $R^3$ and $R^4$ combine together with the atoms to which they are attached to form a cycloalkyl, cycloheteroaryl, aryl, or heteroaryl;

each $R^{16}$ and $R^{17}$ are, independent of the other, hydrogen, OH, O$^-$, halogen, amine, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, $C_6$-$C_{14}$ aryloxy, $C_3$-$C_{10}$ cycloalkyl, or $C_3$-$C_{10}$ cycloalkenyl, wherein each $R^{16}$ and $R_{15}$, independent of the other, is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl;

M is Ru or Ir;

each L is independently selected from Cl, Br, $CH_3CN$, DMF, $H_2O$, bipyridine, phenylpyridine, $CO_2$, and a CNC-pincer ligand; and n is 1, 2, or 3.

Additional advantages will be set forth, in part, in the detailed figures and claims which follow, and in part will be derived from the detailed description, or can be learned by practice of the invention. The advantages described below will be realized and attained by means of the elements and combinations particularly pointed out in the appended claims. It is to be understood that both the foregoing general description and the following detailed description are exemplary and explanatory only and are not restrictive.

Figure 1:
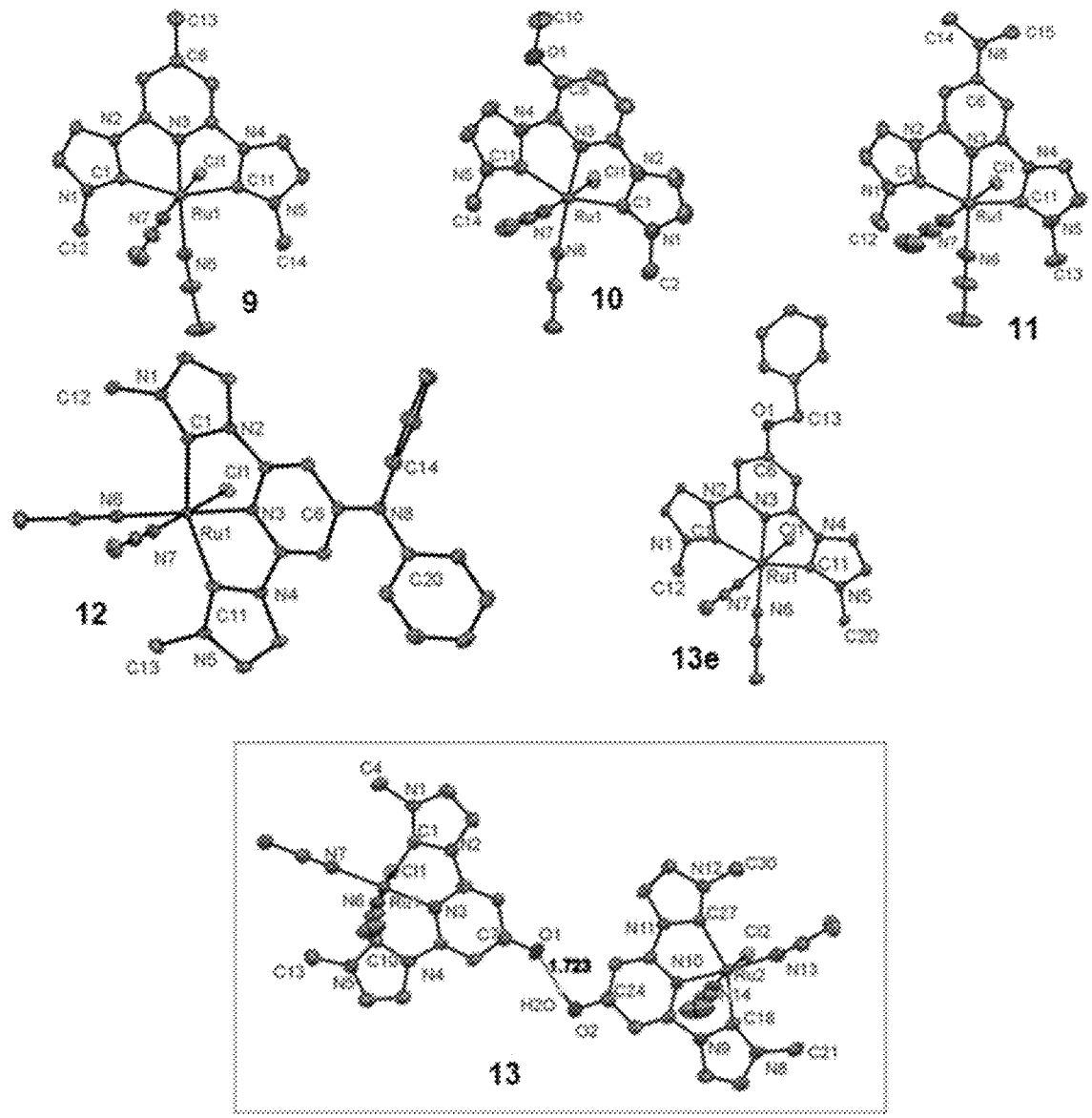
FIG. 1 depicts molecular diagrams of complexes 9, 10, 11 (same as $1^{NMe2}$) 12, 13e, and 13 (same as $1^{OH}$) based on crystallographic data with hydrogen atoms (except for H-bonded one in 13 (same as $1^{OH}$)) and counter-anions removed for clarity. Thermal ellipsoids are drawn at the 40% probability level.

The accompanying figures, which are incorporated in and constitute a part of this specification, illustrate several aspects described below.

DETAILED DESCRIPTION

The materials, compounds, compositions, and methods described herein may be understood more readily by reference to the following detailed description of specific aspects of the disclosed subject matter, the Figures, and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Definitions

As used herein, the terms "optional" or "optionally" means that the subsequently described event or circumstance can or cannot occur and that the description includes instances where said event or circumstance occurs and instances where it does not.

It is appreciated that certain features of the disclosure, which are, for clarity, described in the context of separate aspects, can also be provided in combination in a single aspect, Conversely, various features of the disclosure, which are, for brevity, described in the context of a single aspect, can also be provided separately or in any suitable subcombination.

As used in the description and the appended claims, the singular forms "a," "an," and "the" include plural referents unless the context clearly dictates otherwise. Thus, for example, reference to "a composition" includes mixtures of two or more such compositions, reference to "an agent" includes mixtures of two or more such agents and the like.

It is also to be understood that the terminology used herein is for the purpose of describing particular aspects only and is not intended to be limiting. As used in the specification and the claims, the term "comprising" can include the aspects "consisting of" and "consisting essentially of."

For the terms "for example" and "such as," and grammatical equivalences thereof, the phrase "and without limitation" is understood to follow unless explicitly stated otherwise.

As used herein, the term "substituted" means that a hydrogen atom is removed and replaced by a substituent. It is contemplated to include all permissible substituents of organic compounds. As used herein, the phrase "optionally substituted" means unsubstituted or substituted. It is to be understood that substitution at a given atom is limited by valency. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with a permitted valence of the substituted atom and the substituent and that the substitution results in a stable compound, e.g., a compound that does not spontaneously undergo transformation such as by rearrangement, cyclization, elimination, etc. In still further aspects, it is understood that when the disclosure describes a group being substituted, it means that the group is substituted with one or more (i.e., 1, 2, 3, 4, or 5) groups as allowed by valence selected from alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "compound," as used herein, is meant to include all stereoisomers, geometric isomers, tautomers, and isotopes of the structures depicted. Compounds described herein identified by name or structure as one particular tautomeric form are intended to include other tautomeric forms unless otherwise specified.

All compounds, and salts thereof (e.g., pharmaceutically acceptable salts), can be found together with other substances such as water and solvents (e.g., hydrates and solvates).

Compounds provided herein also can include tautomeric forms. Tautomeric forms result from the swapping of a single bond with an adjacent double bond together with the concomitant migration of a proton. Tautomeric forms include prototropic tautomers that are isomeric protonation states having the same empirical formula and total charge. Example prototropic tautomers include ketone-enol pairs, amide-imidic acid pairs, lactam lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds provided herein can also include all isotopes of atoms occurring in the intermediates or final compounds. Isotopes include those atoms having the same atomic number but different mass numbers. For example, isotopes of hydrogen include hydrogen, tritium, and deuterium.

Also provided herein are salts of the compounds described herein. It is understood that the disclosed salts can refer to derivatives of the disclosed compounds wherein the parent compound is modified by converting an existing acid or base moiety to its salt form. Examples of the salts include, but are not limited to, mineral or organic acid salts of basic residues such as amines; alkali or organic salts of acidic residues such as carboxylic acids; and the like. The salts of the compounds provided herein include the conventional non-toxic salts of the parent compound formed, for example, from non-toxic inorganic or organic acids. The salts of the compounds provided herein can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. In various aspects, a nonaqueous media like ether, ethyl acetate, alcohols (e.g., methanol, ethanol, isopropanol, or butanol) or acetonitrile (ACN) can be used. Lists of suitable salts are found in Remingtons's Pharmaceutical Sciences, 17th ed., Mack Publishing Company, Easton, Pa., 1985, p. 1418 and Journal of Pharmaceutical Science, 66, 2 (1977). Conventional methods for preparing salt forms are described, for example, in Handbook of Pharmaceutical Salts: Properties, Selection, and Use, Wiley-VCH, 2002.

In various aspects, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art. As used herein, chemical structures that contain one or more stereocenters depicted with dashed and bold bonds (i.e.,) are meant to indicate absolute stereochemistry of the stereocenter(s) present in the chemical structure. As used herein, bonds symbolized by a simple line do not indicate a stereo-preference. Unless otherwise indicated to the contrary, chemical structures, which include one or more stereocenters, illustrated herein without indicating absolute or relative stereochemistry encompass all possible stereoisomeric forms of the compound (e.g., diastereomers and enantiomers) and mixtures thereof. Structures with a single bold or dashed line and at least one additional simple line encompass a single enantiomeric series of all possible diastereomers.

The resolution of racemic mixtures of compounds can be carried out using appropriate methods. An exemplary method includes fractional recrystallization using a chiral resolving acid that is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid, or the various optically active camphorsulfonic acids such as camphorsulfonic acid. Other resolving agents suitable for fractional crystallization methods include stereoisomerically pure forms of methylbenzylamine (e.g., S and R forms, or diastereomerically pure forms), 2-phenylglycinol, norephedrine, ephedrine, N-methylephedrine, cyclohexylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent compositions can be determined by one skilled in the art.

The expressions "ambient temperature" and "room temperature" as used herein are understood in the art and refer generally to a temperature, e.g., a reaction temperature, that is about the temperature of the room in which the reaction is carried out, for example, a temperature from about 20° C. to about 30° C.

"$R^1$," "$R^2$," "$R^3$," "$R^4$," etc. are used herein as generic symbols to represent various specific substituents. These symbols can be any substituent, not limited to those disclosed herein, and when they are defined to be certain substituents in one instance, they can, in another instance, be defined as some other substituents.

At various places in the present specification, divalent linking substituents are described. It is specifically intended that each divalent linking substituent includes both the forward and backward forms of the linking substituent. For example, —NR(CR'R")$_n$—includes both —NR(CR'R")$_n$— and —(CR'R")$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

Throughout the definitions, the term "$C_n$-$C_m$" indicates a range that includes the endpoints, wherein n and m are integers and indicate the number of carbons. Examples include, without limitation, $C_1$-$C_4$, $C_1$-$C_6$, and the like.

The term "aliphatic" as used herein refers to a non-aromatic hydrocarbon group and includes branched and unbranched, alkyl, alkenyl, or alkynyl groups. As used herein, the term "$C_n$-$C_m$ alkyl," employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, teri-butyl, isobutyl, sec-butyl; higher homologs such as 2-methyl-l-butyl, n-pentyl, 3-pentyl, n-hexyl, 1,2,2-trimethylpropyl, heptyl, octyl, nonyl, decyl, dodecyl, tetradecyl, hexadecyl, eicosyl, tetracosyl, and the like. In various aspects, the alkyl group contains from 1 to 24 carbon atoms, from 1 to 12 carbon atoms, from 1 to 10 carbon atoms, from 1 to 8 carbon atoms, from 1 to 6 carbon atoms, from 1 to 4 carbon atoms, from 1 to 3 carbon atoms, or 1 to 2 carbon atoms. The alkyl group can also be substituted or unsubstituted. Throughout the specification, "alkyl" is generally used to refer to both unsubstituted alkyl groups and substituted alkyl groups; however, substituted alkyl groups are also specifically referred to herein by identifying the specific substituent(s) on the alkyl group. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below and the like. When "alkyl" is used in one instance, and a specific term such as "alkylalcohol" is used in another, it is not meant to imply that the term "alkyl" does not also refer to specific terms such as "alkylalcohol" and the like.

As used herein, "$C_n$-$C_m$ alkenyl" refers to an alkyl group having one or more double carbon-carbon bonds and having n to m carbons, Example alkenyl groups include, but are not limited to, ethenyl, n-propenyl, isopropenyl, n-butenyl, seobutenyl, and the like. In various aspects, the alkenyl moiety contains 2 to 6, 2 to 4, or 2 to 3 carbon atoms. Asymmetric structures such as ($R^1R^2$)C=C($R^3R^4$) are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, cyano, silyl, sulfo-oxo, sulfonyl, sulfone, sulfoxide, thiol, thiol, or phosphonyl, as described below.

As used herein, "$C_n$-$C_m$ alkynyl" refers to an alkyl group having one or more triple carbon-carbon bonds and having n to m carbons. Exemplary alkynyl groups include, but are not limited to, ethynyl, propyn-1-yl, propyn-2-yl, and the like. In various aspects, the alkynyl moiety contains 2 to 6, 2 to 4, or 2 to 3 carbon atoms. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl, as described below As used herein, the term "$C_n$-$C_m$ alkylene," employed alone or in combination with other terms, refers to a divalent alkyl linking group having n to m carbons. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like. In various aspects, the alkylene moiety contains 2 to 6, 2 to 4, 2 to 3, 1 to 6, 1 to 4, or 1 to 2 carbon atoms.

As used herein, the term "$C_n$-$C_m$ alkoxy," employed alone or in combination with other terms, refers to a group of formula —O-alkyl, wherein the alkyl group has n to m carbons. Examples of alkoxy groups include methoxy, ethoxy, propoxy (e.g., w-propoxy and isopropoxy), ten-butoxy, and the like. In various aspects, the alkyl group has 1 to 6, 1 to 4, or 1 to 3 carbon atoms.

The terms "amine" or "amino" as used herein are represented by the formula —$NR^1R^2$, where $R^1$ and $R^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above. "Amido" is —C(O)$NR^1R^2$.

As used herein, the term "$C_n$-$C_m$ alkylamino" refers to a group of formula —NH(alkyl), wherein the alkyl group has n to m carbon atoms. In various aspects, the alkyl group has 1 to 6, 1 to 4, or 1 to 3 carbon atoms.

As used herein, the term "$C_n$-$C_m$ alkoxycarbonyl" refers to a group of formula —C(O)O-alkyl, wherein the alkyl group has n to m carbon atoms. In various aspects, the alkyl group has 1 to 6, 1 to 4, or 1 to 3 carbon atoms.

As used herein, the term "$C_n$-$C_m$ alkylcarbonyl" refers to a group of formula —C(O)-alkyl, wherein the alkyl croup has n to m carbon atoms. In various aspects, the alkyl group has 1 to 6, 1 to 4, or 1 to 3 carbon atoms.

As used herein, the term "$C_n$-$C_m$ alkylcarbonylamino" refers to a group of formula —NHC(O)-alkyl, wherein the alkyl group has n to m carbon atoms. In various aspects, the alkyl group has 1 to 6, 1 to 4, or 1 to 3 carbon atoms.

As used herein, the term "$C_n$-$C_m$ alkylsulfonylamino" refers to a group of formula —NHS(O)$_2$-alkyl, wherein the alkyl group has n to m carbon atoms. In various aspects, the alkyl group has 1 to 6, 1 to 4, or 1 to 3 carbon atoms.

The term "aldehyde," as used herein, is represented by the formula —C(O)H. Throughout this specification, "C(O)" or "CO" is a shorthand notation for C=O, which is also referred to herein as a "carbonyl."

The term "carboxylic acid," as used herein, is represented by the formula —C(O)OH. A "carboxylate" or "carboxyl" group as used herein is represented by the formula —C(O)O$^-$.

The term "ester" as used herein is represented by the formula —OC(O)$R^1$ or —C(O)O$R^1$, where $R^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $R^1OR^2$, where $R^1$ and $R^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $R^1C(O)R^2$, where $R^1$ and $R^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

As used herein, the term "aminosulfonyl" refers to a group of formula —S(O)$_2$NH$_2$.

As used herein, the term "$C_n$-$C_m$ alkylaminosulfonyl" refers to a group of formula —S(O)$_2$NH(alkyl), wherein the alkyl group has n to m carbon atoms. In various aspects, the alkyl group has 1 to 6, 1 to 4, or 1 to 3 carbon atoms.

As used herein, the term "di($C_n$-$C_m$ alkyl)aminosulfonyl" refers to a group of formula —S(O)$_2$N(alkyl)$_2$, wherein each alkyl group independently has n to m carbon atoms. In various aspects, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_n$-$C_m$ alkylaminosulfonylamino" refers to a group of formula —NHS(O)$_2$NH(alkyl), wherein the alkyl group has n to m carbon atoms. In various aspects, the alkyl group has 1 to 6, 1 to 4, or 1 to 3 carbon atoms.

As used herein, the term "di($C_n$-$C_m$ alkyl)aminosulfonylamino" refers to a group of formula —NHS(O)$_2$N(alkyl)$_2$, wherein each alkyl group independently has n to m carbon atoms. In various aspects, each alkyl group has, independently, 1 to 6, 1 to 4, or 1 to 3 carbon atoms.

As used herein, the term "aminocarbonylamino," employed alone or in combination with other terms, refers to a group of formula —NHC(O)NH$_2$.

As used herein, the term "$C_n$-$C_m$ alkylaminocarbonylamino" refers to a group of formula —NHC(O)NH(alkyl), wherein the alkyl group has n tom carbon atoms. In various aspects, the alkyl group has 1 to 6, 1 to 4, or 1 to 3 carbon atoms.

As used herein, the term "di($C_n$-$C_m$ alkyl)aminocarbonylamino" refers to a group of formula —NHC(O)N(alkyl)$_2$, wherein each alkyl group independently has n to m carbon atoms. In various aspects, each alkyl group has, independently, 1 to 6, 1 to 4, or 1 to 3 carbon atoms.

As used herein, the term "$C_n$-$C_m$ alkylcarbamyl" refers to a group of formula —C(O)—NH(alkyl), wherein the alkyl group has n to m carbon atoms. In various aspects, the alkyl group has 1 to 6, 1 to 4, or 1 to 3 carbon atoms.

As used herein, the term "thio" refers to a group of formula —SH.

As used herein, the term "$C_n$-$C_m$ alkylthio" refers to a group of formula —S— alkyl, wherein the alkyl group has n to m carbon atoms. In various aspects, the alkyl group has 1 to 6, 1 to 4, or 1 to 3 carbon atoms.

As used herein, the term "$C_n$-$C_m$ alkylsulfinyl" refers to a group of formula —S(O)-alkyl, wherein the alkyl group has n to m carbon atoms. In various aspects, the alkyl group has 1 to 6, 1 to 4, or 1 to 3 carbon atoms.

As used herein, the term "$C_n$-$C_m$ alkylsulfonyl" refers to a group of formula —S(O)$_2$-alkyl, wherein the alkyl group has n to m carbon atoms. In various aspects, the alkyl group has 1 to 6, 1 to 4, or 1 to 3 carbon atoms.

As used herein, the term "carbamyl" to a group of formula —C(O)NH$_2$.

As used herein, the term "carbonyl" employed alone or in combination with other terms, refers to a —C(=O)— group, which may also be written as C(O).

As used herein, the term "carboxy" refers to a group of formula —C(O)OH.

As used herein, the term "$(C_n\text{-}C_m)(C_n\text{-}C_m)$amino" refers to a group of formula —N(alkyl)$_2$, wherein the two alkyl groups each has, independently, n to m carbon atoms. In various aspects, each alkyl group independently has 1 to 6, 1 to 4, or 1 to 3 carbon atoms.

As used herein, the term "di($C_n\text{-}C_m$-alkyl)carbamyl" refers to a group of formula —C(O)N(alkyl)$_2$, wherein the two alkyl groups each has, independently, n to m carbon atoms. In various aspects, each alkyl group independently has 1 to 6, 1 to 4, or 1 to 3 carbon atoms.

As used herein, "halogen" refers to F, Cl, Br, or I.

The term "hydroxyl" as used herein is represented by the formula —OH.

The term "cyano" as used herein is represented by the formula —CN.

The term "nitro" as used herein is represented by the formula —NO$_2$.

The term "phosphonyl" is used herein to refer to the phospho-oxo group represented by the formula —P(O)(OR$^1$)$_2$, where R$^1$ can be absent, hydrogen, an alkyl, alkenyl, alkynyl, aryl, heteroaryl, cycloalkyl, or cycloalkenyl.

The term "silyl" as used herein is represented by the formula —SiR$^1$R$^2$R$^3$, where R$^1$, R$^2$, and R$^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —S(O)$_2$R$^1$, where R$^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH—.

As used herein, "$C_n\text{-}C_m$ haloalkoxy" refers to a group of formula —O-haloalkyl having n to m carbon atoms. An example haloalkoxy group is OCF$_3$. In various aspects, the haloalkoxy group is fluorinated only. In various aspects, the alkyl group has 1 to 6, 1 to 4, or 1 to 3 carbon atoms.

As used herein, the term "$C_n\text{-}C_m$ haloalkyl," employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In various aspects, the haloalkyl group is fluorinated only. In various aspects, the alkyl group has 1 to 6, 1 to 4, or 1 to 3 carbon atoms.

As used herein, the term "amine base" refers to a mono-substituted amino group (i.e., primary amine base), di-substituted amino group (i.e., secondary amine base), or a tri-substituted amine group (i.e., tertiary amine base). Exemplary mono-substituted amine bases include methylamine, ethylamine, propylamine, butylamine, and the like. Example di-substituted amine bases include dimethylamine, diethylamine, dipropylamine, dibutylamine, pyrrolidine, piperidine, azepane, morpholine, and the like. In various aspects, the tertiary amine has the formula N(R')$_3$, wherein each R' is independently $C_1$-6 alkyl, 3-10 member cycloalkyl, 4-10 membered heterocycloalkyl, 1-10 membered heteroaryl, and 5-10 membered aryl, wherein the 3-10 member cycloalkyl, 4-10 membered heterocycloalkyl, 1-10 membered heteroaryl, and 5-10 membered aryl is optionally substituted by 1, 2, 3, 4, 5, or 6 Ci-6 alkyl groups. Exemplary tertiary amine bases include trimethylamine, triethylamine, tripropylamine, triisopropylamine, tributylamine, tri-tert-butylamine, N,N-dimethylethanamine, N-ethyl-N-methylpropan-2-amine, N-ethyl-N-isopropylpropan-2-amine, morpholine, N-methylmorpholine, and the like. In various aspects, the term "tertiary amine base" refers to a group of formula N(R)$_3$, wherein each R is independently a linear or branched C$_1$-6 alkyl group.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Cycloalkyl groups can have 3, 4, 5, 6, 7, 8, 9, or 10 ring-forming carbons (C$_{3-10}$). Ring-forming carbon atoms of a cycloalkyl group can be optionally substituted by oxo or sulfido (e.g., C(O) or C(S)). Cycloalkyl groups also include cycloalkylidenes. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In various aspects, cycloalkyl is cyclopropyl, cyclobutyl, cyclopentyl, cyclohexyl, cyclopentyl, or adamantyl. In various aspects, the cycloalkyl has 6-10 ring-forming carbon atoms. In various aspects, cycloalkyl is cyclohexyl or adamantyl. Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom, including a ring-forming atom of the fused aromatic ring.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, and 7-membered heterocycloalkyl groups. Heterocycloalkyl groups can also include spirocycles. Examples of heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or S(O)$_2$, etc.). The heterocycloalkyl group can be attached through a ring-forming carbon atom or a ring-forming heteroatom. In various aspects, the heterocycloalkyl group contains 0 to 3 double bonds. In various aspects, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom, including a ring-forming atom of the fused aromatic ring. In various aspects, the heterocycloalkyl has 4-10, 4-7 or 4-6 ring atoms with 1 or 2 heteroatoms independently selected from nitrogen, oxygen, or sulfur and having one or more oxidized ring members.

The term "cycloalkenyl," as used herein, is a non-aromatic carbon-based ring composed of at least three carbon atoms and containing at least one double bond, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl, as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In various aspects, aryl groups have from 6 to about 20 carbon atoms, from 6 to about 15 carbon atoms, or from 6 to about 10 carbon atoms. In various aspects, the aryl group is a substituted or unsubstituted phenyl.

As used herein, "heteroaryl" refers to a monocyclic or polycyclic aromatic heterocycle having at least one heteroatom ring member selected from sulfur, oxygen, phosphorus, and nitrogen. In various aspects, the heteroaryl ring has 1, 2, 3, or 4 heteroatom ring members independently selected from nitrogen, sulfur and oxygen. In various aspects, any ring-forming N in a heteroaryl moiety can be an N-oxide. In various aspects, the heteroaryl has 5-10 ring atoms and 1, 2, 3 or 4 heteroatom ring members independently selected from nitrogen, sulfur and oxygen. In various aspects, the heteroaryl has 5-6 ring atoms and 1 or 2 heteroatom ring members independently selected from nitrogen, sulfur and oxygen. In various aspects, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl, and pyridazinyl.

The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl, as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

At certain places, the definitions or aspects refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

As used herein, the term "electron withdrawing group" (EWG), employed alone or in combination with other terms, refers to an atom or group of atoms substituted onto a π-system (e.g., substituted onto an aryl or heteroaryl ring) that draws electron density away from the π-system through induction (e.g., withdrawing electron density about a σ-bond) or resonance (e.g., withdrawing electron density about a π-bond or π-system). Example electron withdrawing groups include, but are not limited to, halo groups (e.g., fluoro, chloro, bromo, iodo), nitriles (e.g., —CN), carbonyl groups (e.g., aldehydes, ketones, carboxylic acids, acid chlorides, esters, and the like), nitro croups (e.g., —NO$_2$), haloalkyl groups (e.g., —CH$_2$F, —CHF$_2$, —CF$_3$, and the like), alkenyl groups (e.g., vinyl), alkynyl groups (e.g., ethynyl), sulfonyl groups (e.g., S(O)R, S(O)$_2$R), sulfonate groups (e.g., —SO$_3$H), and sulfonamide groups (e.g., S(O)N(R)$_2$, S(O)$_2$N(R)=). In various aspects, the electron withdrawing group is selected from the group consisting of halo, C$_2$-C$_6$ alkenyl, C$_2$-C$_6$ alkynyl, C$_1$-C$_3$ haloalkyl, ON, NO$_2$, C(=O)OR$^{al}$, O(=O)R$^{bl}$, C(=O)NR$^{cl}$R$^{dl}$, C(=O)SR$^{el}$, —NR$^{cl}$S(O)R$^{el}$, —NR$^{cl}$S(O)$_2$R$^{el}$, S(=O)R$^{el}$, S(=O)$_2$R$^{el}$, S(=O)NR$^{cl}$R$^{dl}$, S(=O)$_2$NR$^{cl}$R$^{dl}$, and P(O)(OR$^{al}$)$_2$. In various aspects, the electron withdrawing group is selected from the group consisting of C(=O)OR$^{al}$, C(=O)R$^{bl}$, C(=O)NR$^{cl}$R$^{dl}$, C(=O)SR$^{el}$, S(=O)R$^{el}$, S(=O)$_2$R$^{el}$, S(=O)NR$^{cl}$R$^{dl}$, and S(=O)$_2$NR$^{cl}$R$^{dl}$. In various aspects, the electron withdrawing group is C(=O)OR$^{al}$. In various aspects, the electron withdrawing group is C(=O)OR$^{al}$, wherein R$^{al}$, R$^{bl}$, R$^{cl}$, R$^{dl}$, and R$^{el}$ are independently selected at each occurrence from alkyl, alkenyl, alkynyl, cycloalkyl, cycloalkenyl, heterocycloalkyl, aryl, or heteroaryl, each of which R$^{al}$, R$^{bl}$, R$^{cl}$, R$^{dl}$, or R$^{el}$ may be optionally substituted with one or more substituents as described herein.

"R$^1$," "R$^2$," "R$^3$," "R$^n$," etc., where n is some integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within the second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Dashed lines in a chemical structure are used to indicate that a bond may be present or absent, or that it may be a delocalized bond between the indicated atoms.

Preparation of the compounds described herein can involve a reaction in the presence of an add or a base. Example acids can be inorganic or organic adds and include, but are not limited to, strong and weak acids. Example adds include, but are not limited to, hydrochloric add, hydrobromic add, sulfuric acid, phosphoric acid; p-toluenesulfonic add, 4-nitrobenzoic acid, methanesulfonic add, benzenesulfonic add, trifluoroacetic acid, and nitric acid. Example weak adds include; but are not limited to, acetic acid, propionic acid, butanoic acid; benzoic acid, tartaric acid, pentanoic add; hexanoic add, heptanoic add, octanoic acid, nonanoic add, and decanoic add. Examples of bases include, without limitation, lithium hydroxide, sodium hydroxide, potassium hydroxide, lithium carbonate, sodium carbonate, potassium carbonate, sodium bicarbonate; and amine bases. Example strong bases include, but are not limited to, hydroxide, alkoxides, metal amides, metal hydrides, metal dialkylamides, and arylamines, wherein; alkoxides include lithium, sodium and potassium salts of methyl, ethyl and t-butyl oxides; metal amides include sodium amide, potassium amide and lithium amide, metal hydrides include sodium hydride, potassium hydride and lithium hydride; and metal dialkylamides include lithium, sodium, and potassium salts of methyl, ethyl, n-propyl, iso-propyl, n-butyl, t-butyl, trimethylsilyl and cyclohexyl substituted amides (e.g., lithium N-isopropylcyclohexylamide).

The following abbreviations may be used herein: AcOH (acetic acid); aq. (aqueous); atm. (atmosphere(s)); $Br_2$ (bromine); Bn (benzyl); calc. (calculated); d (doublet); dd (doublet of doublets); DCM (dichloromethane); DMF (N,N-dimethylformamide); Et (ethyl); $Et_2O$ (diethyl ether); EtOAc (ethyl acetate); EtOH (ethanol); EWG (electron withdrawing group); g (gram(s)); h (hour(s)); HCl (hydrochloric add/hydrogen chloride); HPLC (high performance liquid chromatography); $H_2S_4$ (sulfuric add); Hz (hertz); (iodine); IPA (isopropyl alcohol); J (coupling constant); KOH (potassium hydroxide); $K_3PO_4$ (potassium phosphate); LCMS (liquid chromatography-mass spectrometry); GC (gas chromatography), DCA (lithium N-isopropylcyclohexylamide); m (multiplet); M (molar); MS (Mass spectrometry); Me (methyl); MeCN (acetonitrile); MeOH (methanol); mg (milligram(s)); min, (minutes(s)); mL (milliliter(s)); mmol (millimole(s)); N (normal); $NaBH_4CN$ (sodium cyanoborohydride); NHP (N-heterocyclic phosphine); NHP—C1 (N-heterocyclic phosphine chloride); $Na_2CO_3$ (sodium carbonate); $NaHCO_3$ (sodium bicarbonate); NaOH (sodium hydroxide); $Na_2SO_4$ (sodium sulfate); nM (nanomolar); NMR (nuclear magnetic resonance spectroscopy); PCb (trichlorophosphine); PMP (4-methoxyphenyl); RP-HPLC (reverse phase high performance liquid chromatography); t (triplet or tertiary); t-Bu (teri-butyl); TEA (triethylamine); TFA (trifluoroacetic acid); THF (tetrahydrofuran); TLC (thin layer chromatography); μg (microgram(s)); μL (microliter(s)); μM (micromolar); wt % (weight percent).

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value.

Similarly, when values are expressed as approximations, by use of the antecedent "about," it will be understood that the particular value forms another aspect. It will be further understood that the endpoints of each of the ranges are significant both in relation to the other endpoint and independently of the other endpoint. Unless stated otherwise, the term "about" means within 5% (e.g., within 2% or 1%) of the particular value modified by the term "about."

As used herein, the term "composition" is intended to encompass a product comprising the specified ingredients in the specified amounts, as well as any product which results, directly or indirectly, from a combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

Reference will now be made in detail to specific aspects of the disclosed materials, compounds, compositions, articles, and methods, examples of which are illustrated in the accompanying Examples and Figures.

Methods

As summarized above, disclosed herein are the methods comprising selectively deoxygenating an aromatic compound having at least one hydroxyl group in the presence of a hydrogen gas and a catalyst system to form a reaction product, wherein the catalyst system comprises a catalyst of formula (I):

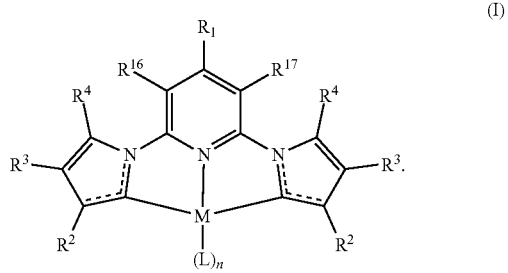

In such aspects, $R^1$ is hydrogen, OH, O$^-$, halogen, amine, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, $C_6$-$C_{14}$ aryloxy, $C_3$-$C_{10}$ cycloalkyl, or $C_3$-$C_{10}$ cycloalkenyl, wherein $R^1$ is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl;

each $R^2$ is, independent of the other, $C_1$-$C_{10}$ alkyl, $C_2$-$C_{10}$ alkenyl, $C_2$-$C_{10}$ alkynyl, $C_6$-$C_{14}$ aryl, or $C_1$-$C_{13}$ heteroaryl, wherein $R^2$ is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, or thiol; each $R^3$ and $R^4$ are, independent of the other, hydrogen, $C_1$-$C_{10}$ alkyl, $C_2$-$C_{10}$ alkenyl, $C_2$-$C_{10}$ alkynyl, $C_6$-$C_{14}$ aryl, or $C_1$-$C_{13}$ heteroaryl, wherein $R^3$ and $R^4$ are optionally substituted with $C_1$-$C_{10}$ alkyl, $C_1$-$C_{10}$ alkoxy, $C_2$-$C_{10}$ alkenyl, C2-C10 alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, or thiol, or $R^3$ and $R^4$ combine together with the atoms to which they are attached to form a cycloalkyl, cycloheteroaryl, aryl, or heteroaryl; each $R^{16}$ and $R^{17}$ are, independent of the other, hydrogen, OH, O−, halogen, amine, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, $C_6$-$C_{14}$ aryloxy, $C_3$-$C_{10}$ cycloalkyl, or $C_3$-$C_{10}$ cycloalkenyl, wherein each $R^{16}$ and $R^{15}$, independent of the other, is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl;

M is Ru or Ir;

each L is independently selected from Cl, Br, $CH_3CN$, DMF, $H_2O$, bipyridine, phenylpyridine, $CO_2$, and a CNC-pincer ligand; and n is 1, 2, or 3.

In some aspects, the aromatic compound having at least one hydroxyl group can have a formula (II):

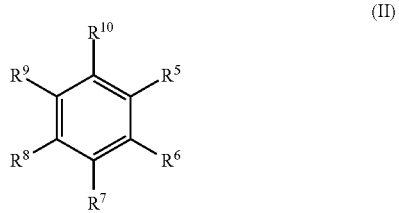

(II)

wherein, $R^5$ is independently selected from hydrogen, substituted or unsubstituted $C_1$-$C_6$-alkyl; $R^{11}$—OH; —$OR^{12}$, $R^{18}OR^{19}$, $R^{20}COR^{21}$, substituted or unsubstituted $C_3$-$C_{10}$ cycloalkyls and heteroalkyls, $C_2$-$C_{10}$ alkenyl, and Ar';

$R^6$ is independently selected from hydrogen, hydrogen, substituted or unsubstituted $R^{11}$—OH; —$OR^{12}$, $R^{18}OR^{19}$, $R^{20}COR^{21}$, substituted or unsubstituted $C_3$-$C_{10}$ cycloalkyls and heteroalkyls, $C_2$-$C_{10}$ alkenyl, and Ar';

$R^7$ is independently selected from hydrogen, substituted or unsubstituted $C_1$-$C_6$-alkyl, $R^{11}$—OH, —$OR^{12}$, $R^{18}OR^{19}$, $R^{20}COR^{21}$, substituted or unsubstituted $C_3$-$C_{10}$ cycloalkyls and heteroalkyls, $C_2$-$C_{10}$ alkenyl, and Ar';

$R^8$ is independently selected from hydrogen, substituted or unsubstituted $C_1$-$C_6$-alkyl, $R^{11}$—OH, —$OR^{12}$, $R^{18}OR^{19}$, $R^{20}COR^{21}$, substituted or unsubstituted $C_3$-$C_{10}$ cycloalkyls and heteroalkyls, $C_2$-$C_{10}$ alkenyl, and Ar';

$R^9$ is independently selected from hydrogen, substituted or unsubstituted $C_1$-$C_6$-alkyl, $R^{11}$—OH, —$OR^{12}$, $R^{18}OR^{19}$, $R^{20}COR^{21}$, substituted or unsubstituted $C_3$-$C_{10}$ cycloalkyls and heteroalkyls, $C_2$-$C_{10}$ alkenyl, and Ar';

$R^{10}$ is independently selected from hydrogen, substituted or unsubstituted $C_1$-$C_6$-alkyl, $R^{11}$—OH, —$OR^{12}$, $R^{18}OR^{19}$, $R^{20}COR^{21}$, substituted or unsubstituted $C_3$-$C_{10}$ cycloalkyls and heteroalkyls, $C_2$-$C_{10}$ alkenyl, and Ar';

wherein when $R^6$, $R^7$, $R^9$, and $R^{10}$ are all hydrogen, $R^5$ is $R^{11}$—OH, $R^{18}OR^{19}$, or $R^{20}COR^{21}$;

wherein $R^{11}$ is a bond, substituted or unsubstituted $C_1$-$C_6$ alkyl, $C_2$-$C_{10}$ alkenyl, or Ar'';

$R^{12}$ is independently selected from hydrogen, substituted or unsubstituted $C_1$-$C_6$ alkyl, $C_2$-$C_{10}$ alkenyl, and Ar''', $R^{18}$ is independently selected from substituted or unsubstituted $C_1$-$C_6$-alkyl, substituted or unsubstituted $C_3$-$C_{10}$ cycloalkyls and heteroalkyls, $C_2$-$C_{10}$ alkenyl, and Ar';

$R^{19}$ is independently selected from substituted or unsubstituted $C_1$-$C_6$-alkyl, substituted or unsubstituted $C_3$-$C_{10}$ cycloalkyls and heteroalkyls, $C_2$-$C_{10}$ alkenyl, and Ar';

$R^{20}$ is independently selected from a bond, substituted or unsubstituted $C_1$-$C_6$-alkyl, substituted or unsubstituted $C_3$-$C_{10}$ cycloalkyls and heteroalkyls, $C_2$-$C_{10}$ alkenyl, and Ar';

$R^{21}$ is independently selected from hydrogen, hydroxyl, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, $C_6$-$C_{14}$ aryloxy, $C_3$-$C_{10}$ cycloalkyl, or $C_3$-$C_{10}$ cycloalkenyl and Ar', wherein $R^{21}$ is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl;

Ar' is a $C_6$-$C_{14}$ aryl or heteroaryl group optionally substituted with 1, 2, or 3 optional substituents; and Ar'' is a $C_6$-$C_{14}$ aryl or heteroaryl group optionally substituted with 1, 2, or 3 optional substituents;

Ar''' is a $C_6$-$C_{14}$ aryl or heteroaryl group optionally substituted with 1, 2, or 3 optional substituents; and wherein Ar', Ar'', or Ar''', are the same or different.

In still further aspects, wherein $R^5$ is $R^{11}$—OH, $R^{18}OR^{19}$, or $R^{20}COR^{21}$, $R^6$ is independently selected from hydrogen, substituted or unsubstituted $C_1$-$C_6$-alkyl, $R^{11}$—OH; —$OR^{12}$, substituted or unsubstituted $C_3$-$C_{10}$ cycloalkyls and heteroalkyls, $C_2$-$C_{10}$ alkenyl, and Ar'; $R^7$ is independently selected from hydrogen, substituted or unsubstituted $R^{11}$—OH; —$OR^{12}$, substituted or unsubstituted $C_3$-$C_{10}$ cycloalkyls and heteroalkyls, $C_2$-$C_{10}$ alkenyl, and Ar'; $R^8$ is independently selected from hydrogen, substituted or unsubstituted $R^{11}$—OH; —$OR^{12}$, substituted or unsubstituted $C_3$-$C_{10}$ cycloalkyls and heteroalkyls, $C_2$-$C_{10}$ alkenyl, and Ar'; wherein $R^9$ is independently selected from hydrogen, substituted or unsubstituted $R^{11}$—OH; —$OR^{12}$, substituted or unsubstituted $C_3$-$C_{10}$ cycloalkyls and heteroalkyls, $C_2$-$C_{10}$ alkenyl, and Ar'; $R^{10}$ is independently selected from hydrogen, substituted or unsubstituted $R^{11}$—OH; —$OR^{12}$, substituted or unsubstituted $C_3$-$C_{10}$ cycloalkyls and heteroalkyls, $C_2$-$C_{10}$ alkenyl, and Ar'; $R^{11}$ is a bond, substituted or unsubstituted $C_1$-$C_6$ alkyl, $C_2$-$C_{10}$ alkenyl, or Ar''; $R^{12}$ is independently selected from hydrogen, substituted or unsubstituted $C_1$-$C_6$ alkyl, $C_2$-$C_{10}$ alkenyl, $R^{18}$ is independently selected from substituted or unsubstituted $C_1$-$C_6$-alkyl, substituted or unsubstituted $C_3$-$C_{10}$ cycloalkyls and heteroalkyls, $C_2$-$C_{10}$ alkenyl, and Ar'; $R^{19}$ is independently selected from substituted or unsubstituted $C_1$-$C_6$-alkyl, substituted or unsubstituted 03-C10 cycloalkyls and heteroalkyls, $C_2$-$C_{10}$ alkenyl, and Ar'; $R^{20}$ is independently selected from a bond, substituted or unsubstituted $C_1$-$C_6$-alkyl, substituted or unsubstituted $C_3$-$C_{10}$ cycloalkyls and heteroalkyls, $C_2$-$C_{10}$ alkenyl, and Ar'; $R^{21}$ is independently selected from hydrogen, hydroxyl, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, $C_6$-$C_{14}$ aryloxy, $C_3$-$C_{10}$ cycloalkyl, or $C_3$-$C_{10}$ cycloalkenyl and Ar', wherein $R^{21}$ is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl; and Ar''', Ar' is a $C_6$-$C_{14}$ aryl or heteroaryl group optionally substituted with 1, 2, or 3 optional substituents; Ar'' a $C_6$-$C_{14}$ aryl or heteroaryl group optionally substituted with 1, 2, or 3 optional substituents; Ar''' a $C_6$-$C_{14}$ aryl or heteroaryl group optionally substituted with 1, 2, or 3 optional substituents; and wherein Ar', Ar'', and Ar''' are same or different.

In certain aspects, the oxygenated aromatic compound can comprise various oxygen containing groups. In still further aspects, the oxygenated aromatic compound can comprise more than one oxygen group. In some aspects, the oxygenated compounds can comprise a hydroxyl group. In still further aspects, the term "oxygenated aromatic compounds" can include, without limitations, any known in the art phenols, alkyl phenols, alkoxy-substituted aromatic compounds (for example, and without limitation, anisole and substituted anisoles), and aromatic carbonyl compounds. The oxygenated compounds also can comprise aliphatic oxygenates such as alcohols and carbonyls.

In yet other aspects, the oxygenated compound can comprise more than one hydroxyl group. In certain aspects, the aromatic compound can comprise at least two hydroxyl groups. In still further aspects, the aromatic compound can comprise more than two hydroxyl groups.

It is understood that the aromatic compound can comprise oxygen containing groups in any position on an aromatic ring. In certain aspects, when more than one oxygen containing groups are present, this group can be positioned in para, meta, or ortho positions on the aromatic ring.

In still further aspects, the aromatic compound having at least one hydroxyl group can be selected from

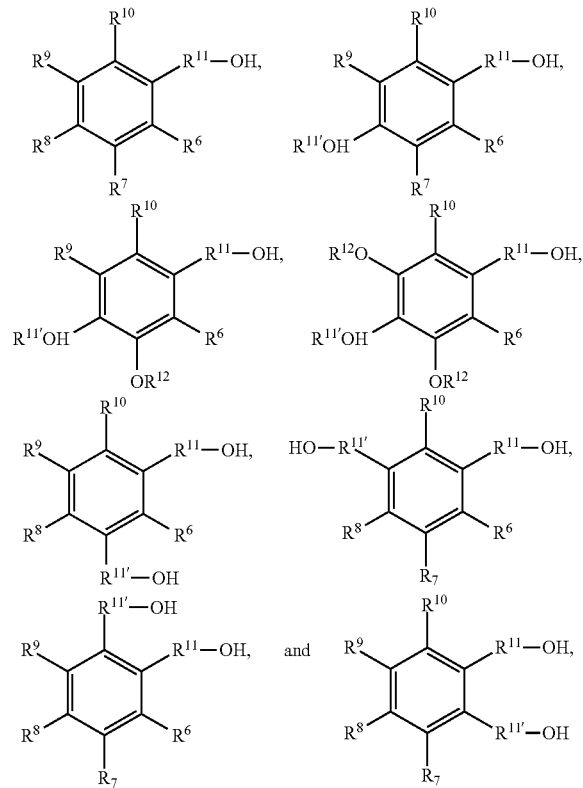

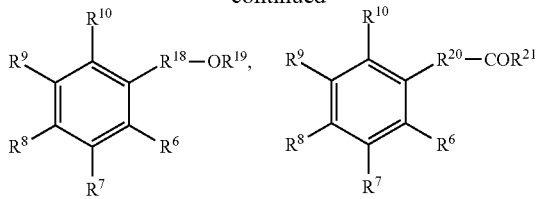

wherein $R^{11}$ can be a bond, substituted or unsubstituted $C_1$-$C_6$ alkyl, $C_2$-$C_{10}$ alkenyl, and Ar'''; and wherein $R^{11'}$ and $R^{11}$ are the same or different. Yet in other aspects, $R^{11}$ and $R^{11'}$ are not the same. In yet other aspects, $R^{18}$ is independently selected from substituted or unsubstituted $C_1$-$C_6$-alkyl, substituted or unsubstituted $C_3$-$C_{10}$ cycloalkyls and heteroalkyls, $C_2$-$C_{10}$ alkenyl, and Ar'; $R^{19}$ is independently selected from substituted or unsubstituted $C_1$-$C_6$-alkyl, substituted or unsubstituted $C_3$-$C_{10}$ cycloalkyls and heteroalkyls, $C_2$-$C_{10}$ alkenyl, and Ar'; $R^{20}$ is independently selected from a bond, substituted or unsubstituted substituted or unsubstituted $C_3$-$C_{10}$ cycloalkyls and heteroalkyls, $C_2$-$C_{10}$ alkenyl, and Ar'; $R^{21}$ is independently selected from hydrogen, hydroxyl, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, $C_6$-$C_{14}$ aryloxy, $C_3$-$C_{10}$ cycloalkyl, or $C_3$-$C_{10}$ cycloalkenyl and Ar', wherein $R^{21}$ is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl.

It is further understood that $R^{18}$—O—$R^{19}$ and $R^{20}COR^{21}$ can be located in any position on the ring and are not limited to $R^5$ position. In yet other aspects, one or more of $R^{18}$—O—$R^{19}$ or $R^{20}COR^{21}$ can be present. In still further aspects, both $R^{18}$—O—$R^{19}$ and $R^{20}COR^{21}$ can be present in any position on the ring.

In still further exemplary aspects, the aromatic compounds can comprise any known in aromatic compounds comprising at least one hydroxyl group. In certain exemplary aspects, the aromatic compounds described herein can comprise lignin, paracoumaryl alcohol, benzyl alcohol, coniferyl alcohol, cinnannyl alcohol, sinapyl alcohol, vanillyl alcohol, anisyl alcohol, veratrole alcohol, methoxybenzyl alcohol, guiacol, and their derivatives, for example, and without limitation alkylated derivatives of the cited alcohols. In still further aspects, the aromatic compounds described herein can comprise a phenylethyl-phenyl ether and it is derivatives.

In still further aspects, the disclosed herein catalyst can be any catalyst disclosed in U.S. Patent Application Publication No. 2019/0083966, which disclosure is incorporated herein by reference in its entirety.

In a still further aspect, $R^1$ can be hydrogen, OH, O⁻, halogen, or optionally substituted amine, alkyl, aryl, alkoxy, or aryloxy. In yet other exemplary aspects, $R^1$ is $OC_1$-$C_{12}$ alkyl, e.g., $OCH_3$. In other examples, $R^1$ is methoxy substituted with $CO^2H$. In some exemplary aspects, $R^1$ is not H.

In some exemplary aspects, each $R^2$ can be optionally substituted alkyl or aryl. Yet, in other aspects, both $R^2$ are methyl.

In some aspects, both $R^3$ and $R^4$ can combine together with the atoms to which they are attached to form a cycloalkyl, cycloheteroaryl, aryl, or heteroaryl. In specific examples, both $R^3$ and $R^4$ can combine together with the atoms to which they are attached to form an aryl or heteroaryl. In yet other aspects, $R^3$ and $R^4$ can be the same or different. In some exemplary aspects, both $R^3$ and $R^4$ can be hydrogen.

In still further aspects, each $R^{16}$ and $R^{17}$, independent of the other, can be hydrogen, OH, O⁻, halogen, amine, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, $C_6$-$C_{14}$ aryloxy, $C_3$-$C_{10}$ cycloalkyl, or 03-C10 cycloalkenyl, wherein each $R^{16}$ and $R_{15}$, independent of the other, is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl.

In certain aspects, M can be Ru, Pt, Pd or Ir. In still further aspects, M is Ru. In yet other aspects, M is Ir. Yet, in other aspects, M can be any transition metal capable of forming a complex with the disclosed compounds. In certain aspects, M can comprise Fe, Co, or Ni. In yet other aspects, M can be Pt. In specific examples, M can be Ni. In other examples, M can be Pd. In still other examples, M can be Fe. In yet further examples, M can be Co.

In still further aspects, the catalyst of formula (I) can exist as ions with a 1+, 2+, or 3+ charge. In such aspects, disclosed herein are compounds wherein the catalyst of formula (I) is associated with one or more counteranions. In some exemplary aspects, suitable counteranions comprise iodide (I⁻), bromide (Br⁻), trifluoroacetate ($CF_3COO^-$), triflate (OTf⁻, $CF_3SO_3^-$), tetrafluoroborate ($BF_4^-$), and hexafluorophosphate ($PF_6^-$).

In certain aspects, L is Cl, Br, $CH_3CN$, DMF, $H_2O$, bipyridine or phenylpyridine. In some exemplary aspects, L is Cl or Br. In still further aspects, at least one L can be Cl. In other aspects, one or more L can be $CH_3CN$. In other aspects, one or more L can be dimethylformamide (DMF). In still further aspects, one or more L can be $H_2O$. In still further aspects, one or more L can be bipyridine or phenylpyridine. In yet further exemplary aspects, L can be a CNC-pincer ligand. The pincer precursor used to form the ligand is shown below:

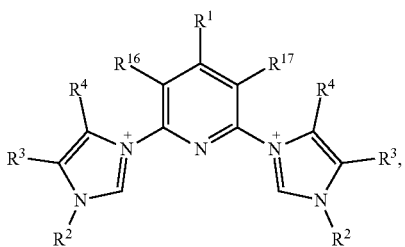

wherein $R^1$, $R^2$, $R^3$, and $R^4$ can be any substituent as described herein. In certain aspects, $R^1$ is hydrogen, OH, O—, halogen, amino, alkyl, alkenyl, alkynyl, aryl, heteroaryl, alkoxy, aryloxy, cycloalkyl, or cycloalkenyl, wherein $R^1$ is optionally substituted with alkyl, alkoxy, alkenyl, alkynyl, aryl, heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl. In yet other aspects, $R^1$ is OH, O⁻, halogen, or optionally substituted amine, alkyl, aryl, alkoxy, or aryloxy, e.g., $OC_{1-12}$ alkyl such as $OCH_3$. In still further aspects, R1 can be methoxy substituted with $CO_2H$.

In certain aspects, each $R^2$ can be, independent of the other, alkyl, alkenyl, alkynyl, aryl, or heteroaryl optionally substituted with alkyl, alkoxy, alkenyl, alkynyl, aryl, heteroaryl, aldehyde, amino, carboxylic acid, ester, ether, halide, hydroxy, ketone, nitro, cyano, silyl, sulfo-oxo, sulfonyl, sulfone, sulfoxide, or thiol. In specific examples, each $R^2$ can be optionally substituted alkyl or aryl. In specific examples, both $R^2$ are methyl.

In still further aspects, each $R^3$ and $R^4$ can be, independent of the other, hydrogen, alkyl, alkenyl, alkynyl, aryl, or heteroaryl optionally substituted with alkyl, alkoxy, alkenyl, alkynyl, aryl, heteroaryl, aldehyde, amino, carboxylic acid, ester, ether, halide, hydroxy, ketone, nitro, cyano, silyl, sulfo-oxo, sulfonyl, sulfone, sulfoxide, or thiol, or $R^3$ and $R^4$ can combine together with the atoms to which they are attached to form a cycloalkyl, cycloheteroaryl, aryl, or heteroaryl. In exemplary aspects, both $R^3$ and $R^4$ can combine together with the atoms to which they are attached to form a cycloalkyl, cycloheteroaryl, aryl, or heteroaryl, preferably an aryl or heteroaryl. In other exemplary aspects, both $R^3$ and $R^4$ can be hydrogen.

In still further aspects, each $R^{16}$ and $R^{17}$ can be independent of the other, hydrogen, OH, O⁻, halogen, amine, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, $C_6$-$C_{14}$ aryloxy, $C_3$-$C_{10}$ cycloalkyl, or $C_3$-$C_{10}$ cycloalkenyl, wherein each $R^{16}$ and $R_{15}$, independent of the other, is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl. In some exemplary aspects, $R^{16}$ and $R^{17}$ can be hydrogen. In yet other exemplary and non-limiting aspects, $R^{16}$ can be —O— group and $R^{17}$ can be hydrogen.

Without wishing to be bound by any theory, it is believed that CNC pincer ligands can modulate electron density at the metal center with and without an electron donor group (O⁻) at the para (to N) position to greatly enhance the electron donor properties for the pyridine ring (A. A. Danopoulos, et al., *Chem. Eur. J.*, 2009, 15, 5491-5502).

In yet other aspects, L can be a CNC pincer ligand formed from the pincer precursor as described above where $R^2$ is $CH_3$:

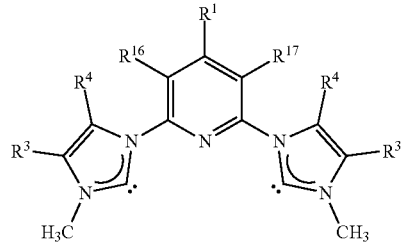

In some exemplary aspects, disclosed herein are the following ruthenium compounds:

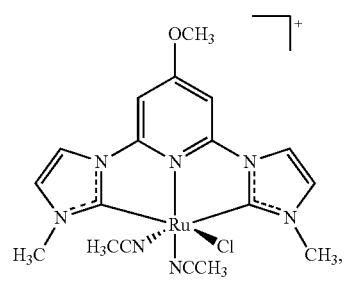

-continued
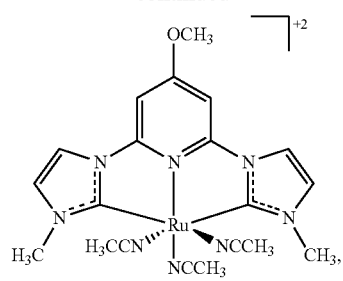
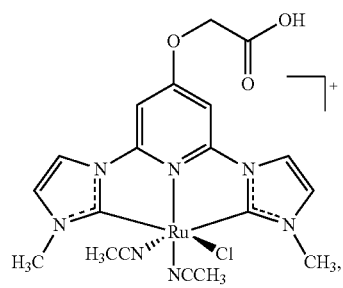
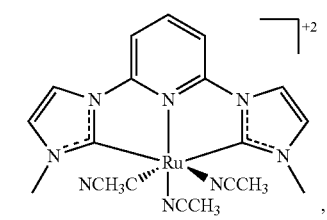
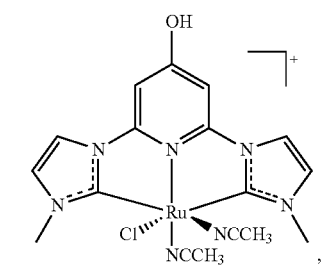
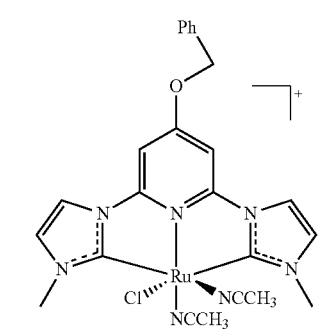
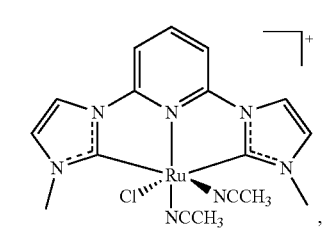
-continued
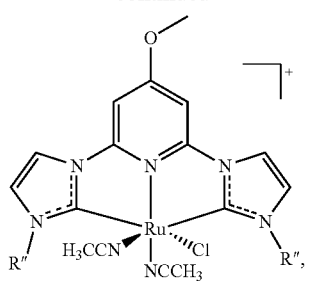
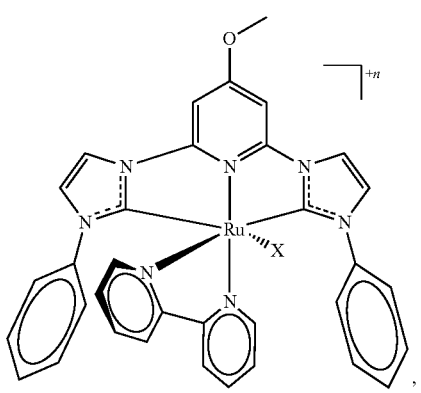
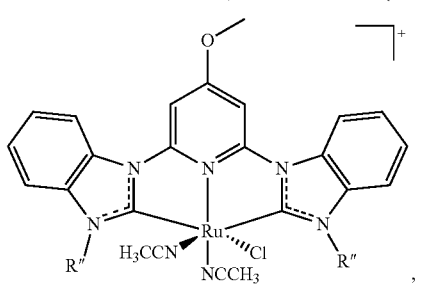
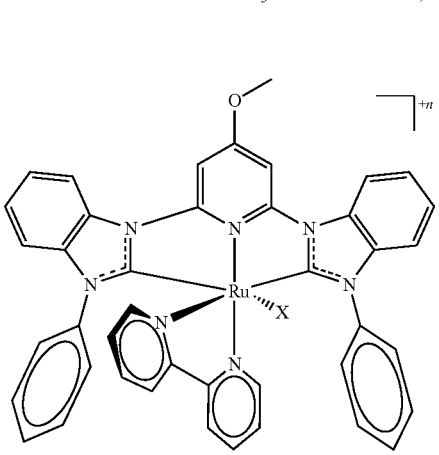
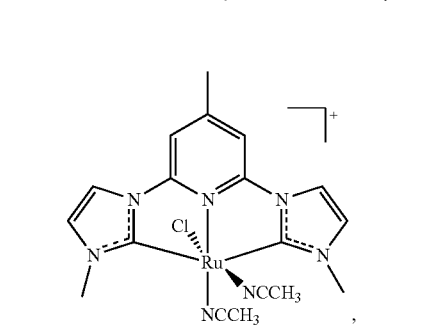

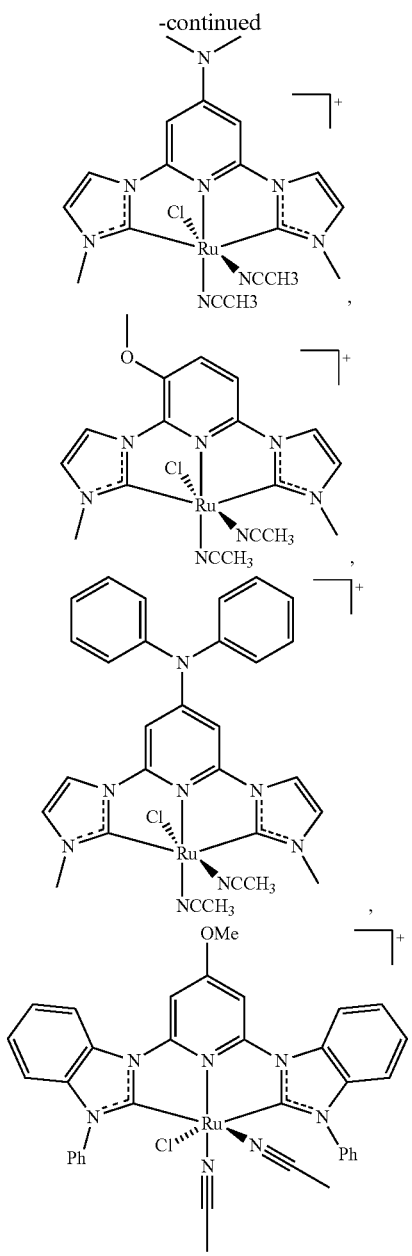
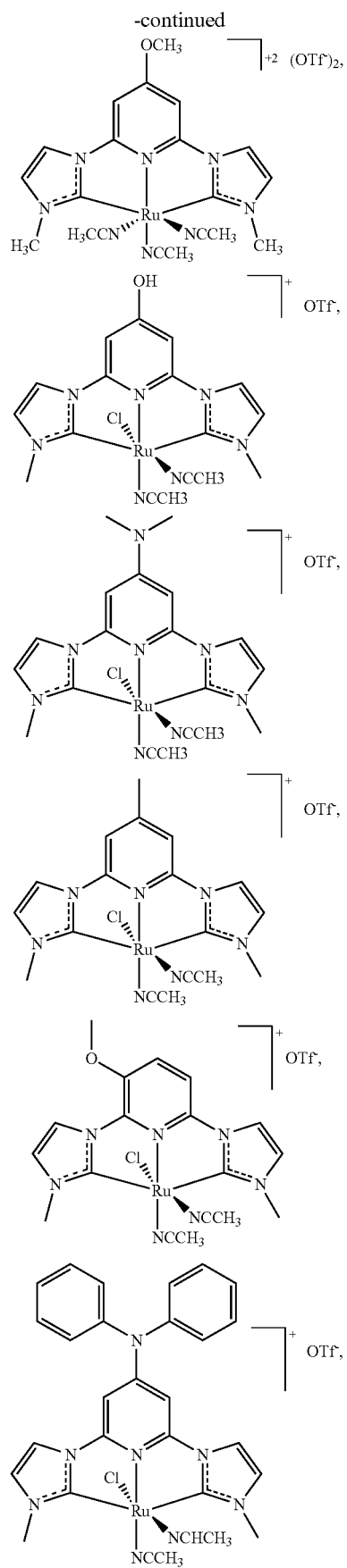
wherein R″ is methyl or phenyl, and X is Cl, Br, or CH$_3$CN, wherein n=1 wherein X is Cl or Br, and n=2 wherein X is CH$_3$CN.
In still further aspects, exemplary ruthenium compounds can comprise:
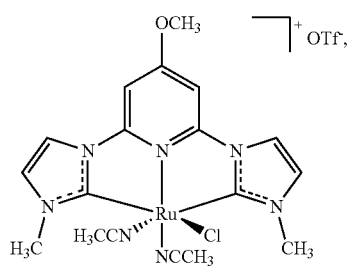

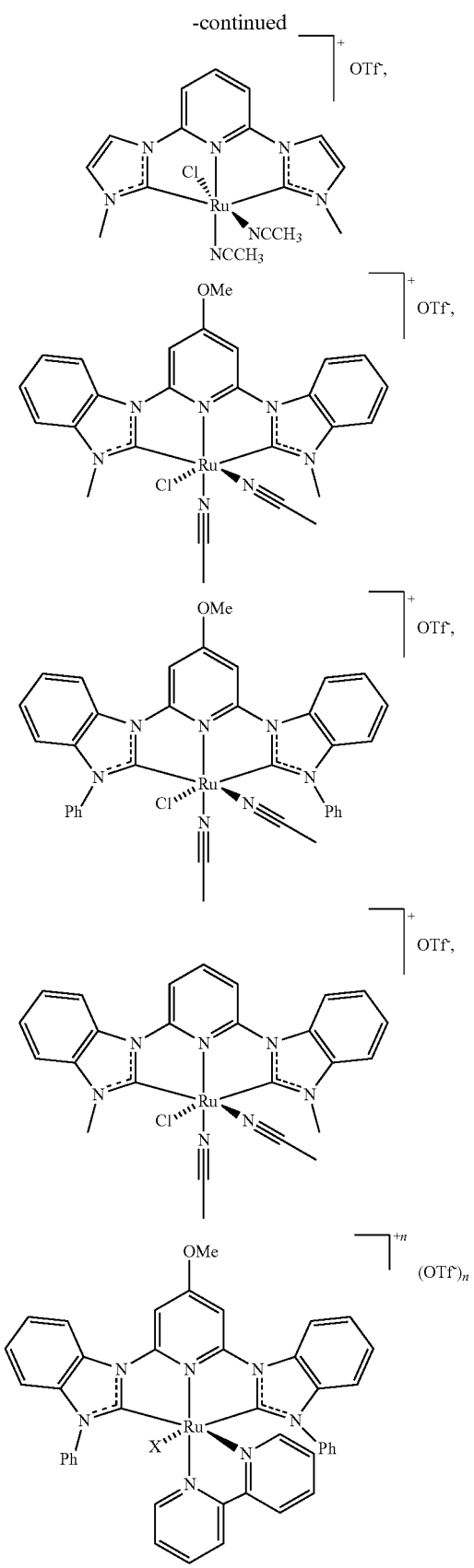

wherein X is Cl or NCCH₃, and wherein
n=1 when X is Cl; and n=2 when X is NCCH₃.

It is understood that the use of the OTf counteranions is exemplary only, and it can be replaced by any of the counteranions disclosed herein.

It is understood that the catalyst disclosed herein can comprise other metals. In some exemplary aspects, the catalyst can comprise nickel compounds, for example:

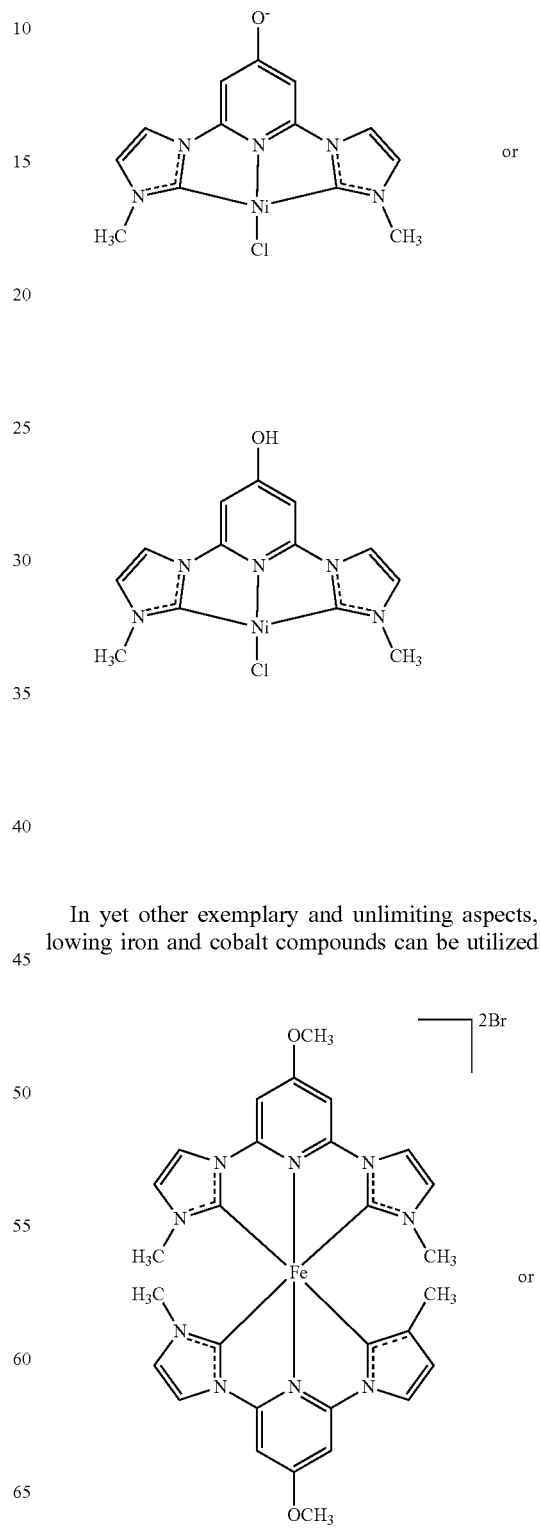

In yet other exemplary and unlimiting aspects, the following iron and cobalt compounds can be utilized:

-continued

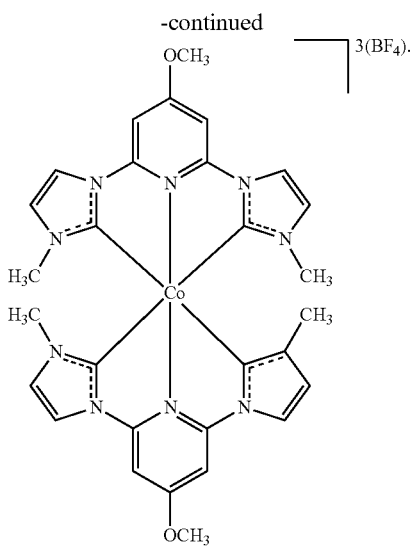

The Br and BF$_4$ counteranions can be substituted with any of the counteranions disclosed herein.

In still further aspects, the catalyst is present in an amount of greater than 0 mol % to about 1.5 mol %, including exemplary values of about 0.05 mol %, about 0.1 mol %, about 4 mol %, about 0.2 mol %, about 0.3 mol %, about 0.0.5 mol %, about 0.6 mol %, about 0.7 mol %, about 0.8 mol %, about 0.9 mol %, about 1.0 mol %, about 1.1 mol %, about 1.2 mol %, about 1.3 mol %, and about 1.4 mol %.

In some exemplary aspects, the catalysts disclosed herein are not anchored to a substrate. In yet other aspects, the catalysts are present in a solvent. Any known in the art solvents can be utilized, for example, and without limitation, methanol, ethanol, isopropanol, acetonitrile, diethyl ether, tetrahydrofuran, nitromethane, and the like.

In some exemplary and unlimiting aspects, the catalysts disclosed herein can be anchored to a surface. In some aspects, the suitable surfaces can comprise metal and metal oxide semiconductors such as TiO$_2$, NiO, SnO$_2$, ZnO. In yet other exemplary aspects, the surfaces comprise, without limitation, glass, metal-coated glass, polymer materials, metal-coated polymers, metal, metal alloy, quartz, paper, transparent conducting material, nanowires, and nanotubes. In some exemplary aspects, the polymer materials are polyalkylenes, polyesters, polyamides, polycarbonates, and polyalkoxyls. In specific examples, the surface can be Mo-coated glass, Au-coated glass, Ni-coated glass, indium tin oxide-coated glass, Mo-coated polyethylene terephthalate, Au-coated polyethylene terephthalate, Ni-coated polyethylene terephthalate, indium tin oxide-coated polyethylene terephthalate, non-woven indium tin oxide, or any other suitable material. In one aspect, a surface can be electrically conductive, for example, to carry charge to or from a film or layer of nanocrystals. In specific examples, the surface can be a metal or metal coated surface.

In still further aspects, the catalyst system of the current disclosure further comprises an external acid or base. It is understood that any known in the art acids and bases can be utilized. In yet other aspects, the catalyst system does not comprise an external acid.

For example, and without limitation, the catalyst system can comprise inorganic acids. In yet other aspects, the inorganic acids are mineral acids. In yet other aspects, the catalyst system can comprise an organic acid. In still further exemplary aspects, the catalyst system can comprise an inorganic base or an organic base. In yet other aspects, the acids and/or base can comprise an Arrhenius acid (base), a Lewis acid (and/or Lewis base), a Brønstead-Lowry acid (and/or Brønstead-Lowry). In still further aspects, any known in the art acids can be used. It is understood that the acids can be monoprotic or polyprotic. In yet other aspects, the bases can comprise any known in the art bases.

In still further aspects, acids (bases) can comprise a strong acid (and/or strong base), a weak acid (and/or weak base). It is understood that the terms "strong" acids and bases are used herein as it commonly used in general chemistry. It is understood that the term "strong" acid (and/or base), when refers to acids (bases) that are capable of forming aqueous solutions, refers to acids (bases) that are fully dissociated in water. The term "weak" acid (and/or base), when refers to acids (bases) that are capable of forming aqueous solutions, refers to acids (bases) that partially dissociate into their ions in water. It is further understood that the degree of the acid/base strength can be determined based on its level of dissociation in water.

In some exemplary aspects, the strong acids comprise hydrochloric acids (HCl), perchloric acid (HClO$_4$), hydrobromic acid (HBr), nitric acid (HNO$_3$), sulfuric acid (H$_2$SO$_4$), hydroiodic acid (HI), p-toluenesulfonic acid, or methanesulfonic acid. In still further aspects, the weak acids can comprise acetic acid, citric acid, lactic acid, phosphoric acid, carbonic acid, hydrofluoric acid, and the like.

In still further aspects, the strong bases comprise LiOH, NaOH, KOH, Ca(OH)$_2$, Ba(OH)$_2$, Sr(OH)$_2$, tetramethylammonium hydroxide, sodium tert-butoxide, and the like. The weak acids can comprise NaHCO$_3$, Na$_2$CO$_3$, or K$_2$CO$_3$.

In still further aspects, the catalyst system of the instant disclosure comprises an external base. In exemplary aspects, the base can be inorganic or organic, as described above. Any known in the art bases can be present in the disclosed catalyst system, including a strong base, a weak base, or a Lewis base.

In still further aspects, the base is present in an amount from about 50 mol % to 100 mol %, including exemplary values of about 55 mol %, about 60 mol %, about 65 mol %, about 70 mol %, about 75 mol %, about 80 mol %, about 85 mol %, about 90 mol %, and about 95 mol %.

In still further aspects, wherein the reaction product comprises a compound A of formula (III)

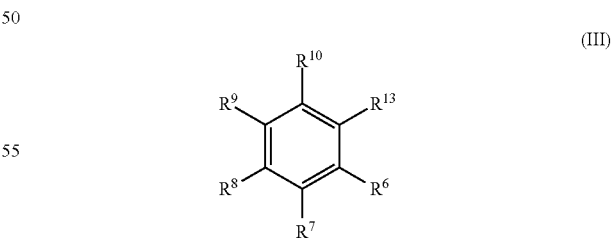

wherein $R^{13}$ is $R^{11}$—H. It is understood that $R^6$-$R^{10}$ can be any of the disclosed above substituents. In yet other aspects, $R^{13}$ can be $R^{18}$—H or $R^{20}$—H. It is understood that in such aspects, $R^6$-$R^{10}$ can be any of the disclosed above substituents.

In still further aspects, when the aromatic compound comprising at least one hydroxyl group is selected from

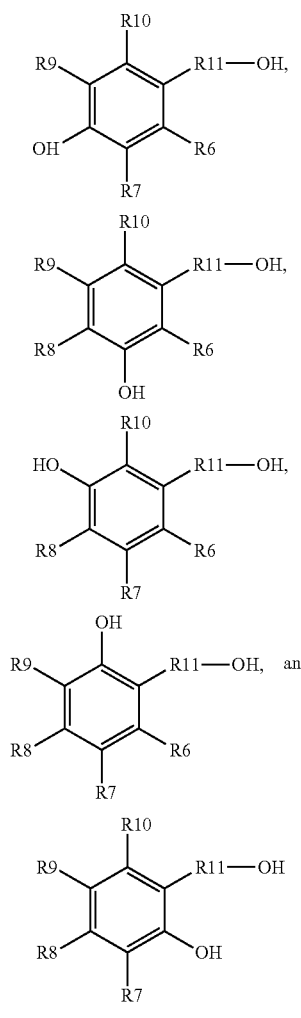

The compound A can comprise:

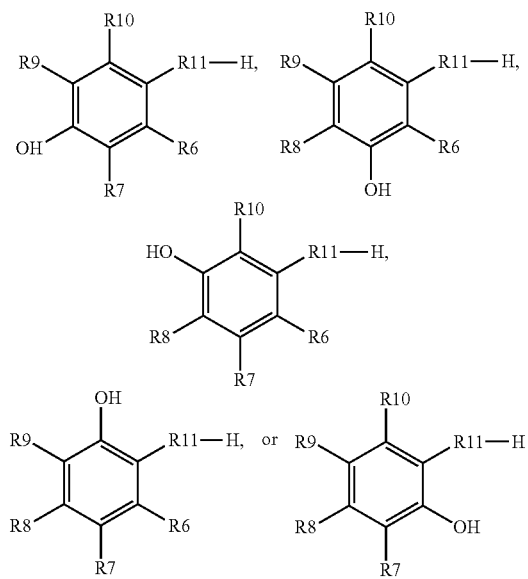

It is understood that in some aspects, the reaction product can comprise additional compounds. In some exemplary aspects, the reaction product can further comprise a compound B of formula (IV):

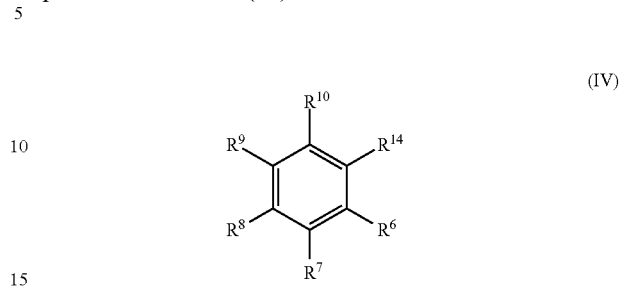

wherein $R^{14}$ is $—OR^{16}$, wherein $R_{15}$ is $C_1$-$C_{10}$ alkyl group, and $R^6$-$R^{10}$ can be selected from any of the disclosed above substituents. In still further aspects, when the aromatic compound comprising at least one hydroxyl group is selected from:

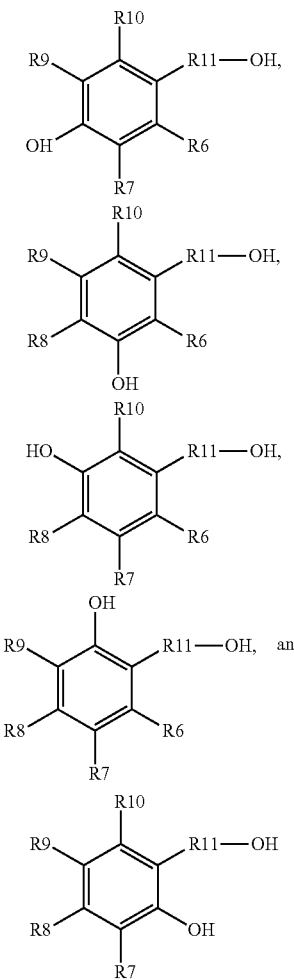

The compound B can comprise:

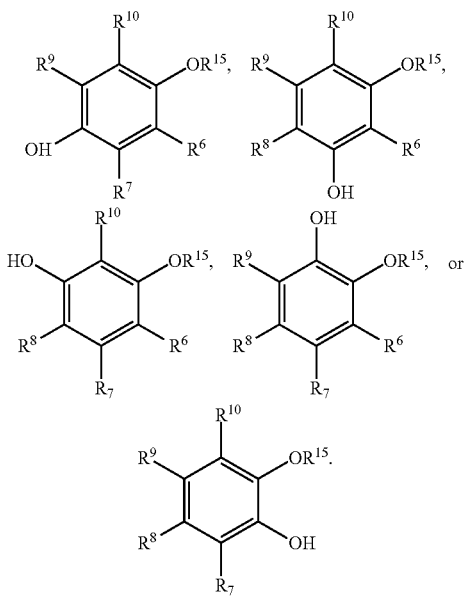

In certain aspects, the compound A is selectively formed over the compound B. In such exemplary aspects, the selectivity of the compound A is from about 50% to 100%, including exemplary values of about 55%, about 60%, about 65%, about 70%, about 75%, about 80%, about 85%, about 90%, and about 95%. It is understood that the compound A can have any selectivity value between any two foregoing values. For example, compound A can have selectivity from about 75% to about 90%, or from about 85% to 100%. In still further aspects, the compound A has a yield from about 50% to 100%, including exemplary values of about 55%, about 60%, about 65%, about 70%, about 75%, about 80%, about 85%, about 90%, and about 95%. It is understood that the compound A can have any yield value between any two foregoing values. For example, compound A can have yield from about 75% to about 90%, or from about 85% to 100%.

Catalyst

It is understood that the catalysts disclosed herein are not limited to the use in deoxygenation reactions only. It is further understood that the disclosed herein catalyst can be utilized in any reaction where their catalytic efficiency in the desired range.

Also, disclosed herein are catalysts of formula (I):

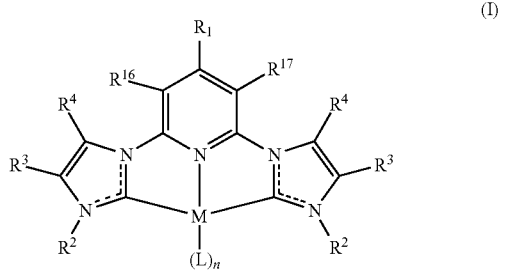

(I)

wherein,
$R^1$ is hydrogen, OH, O$^-$, halogen, amine, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, $C_6$-$C_{14}$ aryloxy, $C_3$-$C_{10}$ cycloalkyl, or $C_3$-$C_{10}$ cycloalkenyl, wherein $R^1$ is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl;

each $R^2$ is, independent of the other, $C_1$-$C_{10}$ alkyl, $C_2$-$C_{10}$ alkenyl, $C_2$-$C_{10}$ alkynyl, $C_6$-$C_{14}$ aryl, or $C_1$-$C_{13}$ heteroaryl, wherein $R^2$ is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, or thiol;

each $R^3$ and $R^4$ are, independent of the other, hydrogen, $C_1$-$C_{10}$ alkyl, $C_2$-$C_{10}$ alkenyl, $C_2$-$C_{10}$ alkynyl, $C_6$-$C_{14}$ aryl, or $C_1$-$C_{13}$ heteroaryl, wherein $R^3$ and $R^4$ are optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, or thiol, or $R^3$ and $R^4$ combine together with the atoms to which they are attached to form a cycloalkyl, cycloheteroaryl, aryl, or heteroaryl;

each $R^{16}$ and $R^{17}$ are, independent of the other, hydrogen, OH, O$^-$, halogen, amine, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, $C_6$-$C_{14}$ aryloxy, $C_3$-$C_{10}$ cycloalkyl, or $C_3$-$C_{10}$ cycloalkenyl, wherein each $R^{16}$ and $R_{15}$, independent of the other, is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl;

M is Ru or Ir;

each L is independently selected from Cl, Br, CH$_3$CN, DMF, H$_2$O, bipyridine, phenylpyridine, CO$_2$, and a CNC-pincer ligand; and n is 1, 2, or 3.

In still some exemplary aspects, the catalyst can be selected from:

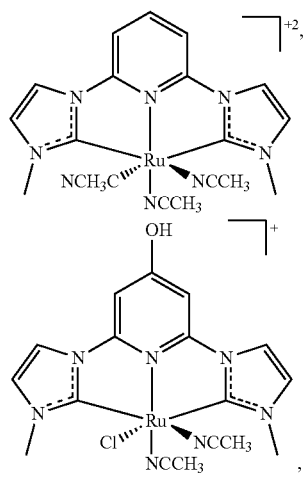

-continued

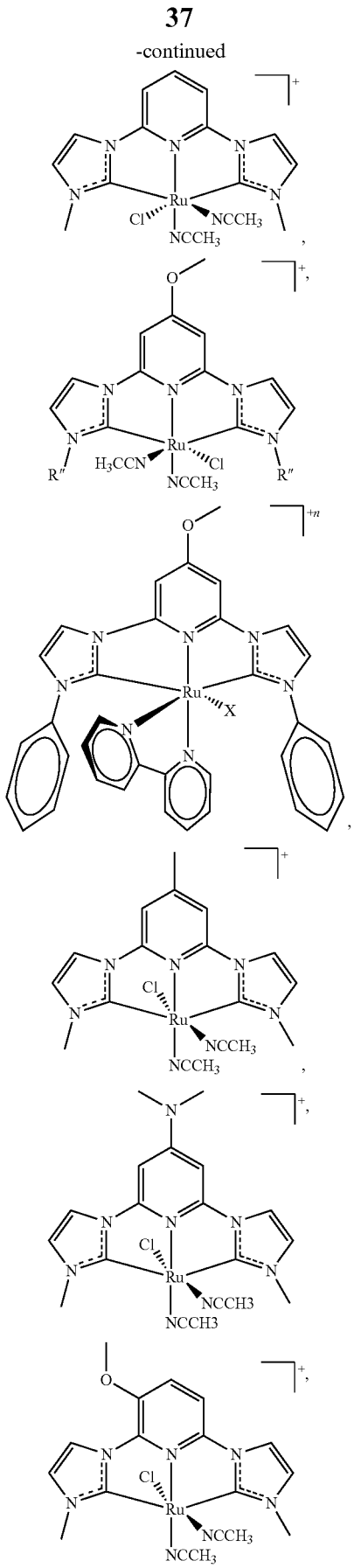

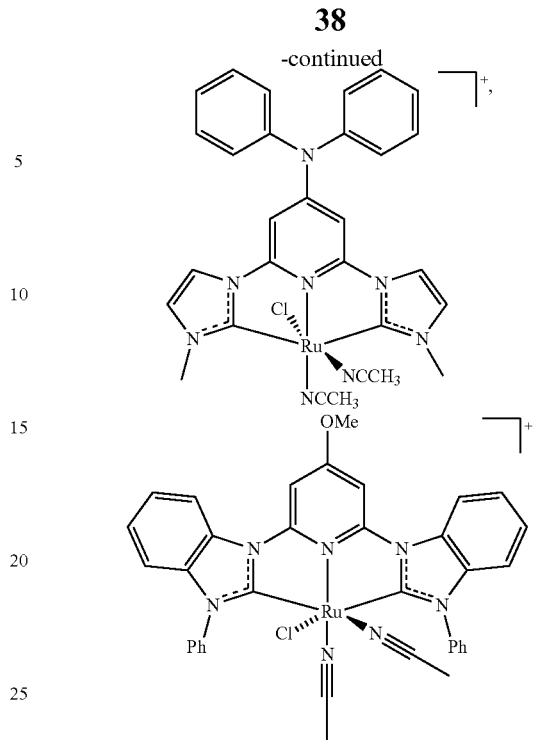

wherein R" is methyl or phenyl, and X is Cl, Br, or CH$_3$CN, and wherein n=1,
when X is Cl or Br, and n=2, wherein X is CH$_3$CN.

EXAMPLES

The following examples are set forth below to illustrate the methods and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

All solvents were dried on a glass contour solvent purification system built by Pure Process Technology, LLC or were used through commercially available dry solvents. Other commercially available reagents were used without further purification necessary. All reactions were prepared and executed under an inert N$_{2(g)}$ environment utilizing Schlenk line techniques or glovebox and oven or flame dried flask. Purifications were conducted open to air unless otherwise stated.

NMR spectra were recorded in a Bruker AVANCE 360 (360 MHz, $^1$H frequency) or AVANCE 500 (500 MHz, $^1$H frequency) NMR spectrometer. FT-IR spectra were recorded in a Bruker Alpha ATR-IR spectrophotometer. Mass spectra were obtained in a Waters AutoSpec-Ultima NT mass spectrometer or Waters Xero G2-XS QTOF. Elemental analyses were done by Atlantic Microlab, Inc. Electrochemical analysis was conducted with a CH Instruments potentiostat (CHI-600E). UV-Vis spectra were recorded with an Ocean Optics FLAME-CHEM-UV-VIS instrument and a cuvette with 1 cm path length in an ambient atmosphere.

$^1$H and {$^1$H}$^{13}$C chemical shifts in NMR were assigned with respect to the residual peaks from deuterated NMR solvents (Gottlieb, H. E.; et al., *The Journal of Organic Chemistry* 1997, 62, 7512-7515). No reference was used for 19F chemical shifts, only the number of peaks are checked.

Additional examples can be found in "Determining the Catalyst Properties that Lead to High Activity and Selectivity for Catalytic Hydrodeoxygenation with Ruthenium Pincer Complexes" by E. T. Papish et al., Organometallics 2020, 39, 5, 662-669, the entire content of which is incorporated herein by reference.

Example 1

The ability of a series of molecular ruthenium catalysts (Scheme 2) (Rodrigues, R. R.; et al., *ACS Appl. Energy Mater.* 2019, 2, 37-46; Das, S.; et al., *Inorg. Chem.* 2019, 58 (12), 8012-8020; Boudreaux, C. M.; et al., *Chem. Commun.* 2017, 53, 11217-11220; Burks, D. B.; et al., *Chem. Commun.* 2018, 54, 3819-3822) to perform selective HDO on vanillyl alcohol was examined. The coordination environment around the Ru center and the electron donating ability of the catalysts were systematically varied to gain an understanding of the catalyst reactivity and how it depends upon ligand design. The results show that the electron donor strength of the ligands plays an important role in the catalytic activity of these catalysts, and this work thus lays the groundwork for the rational design of future molecular HDO catalysts.

Scheme 2

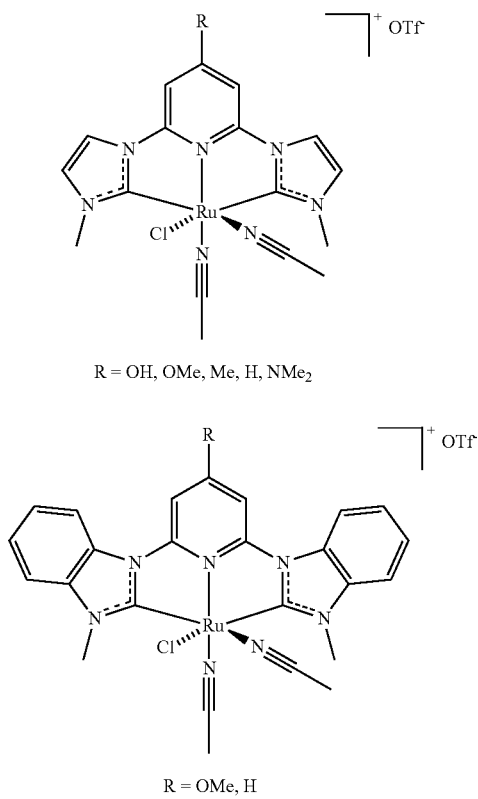

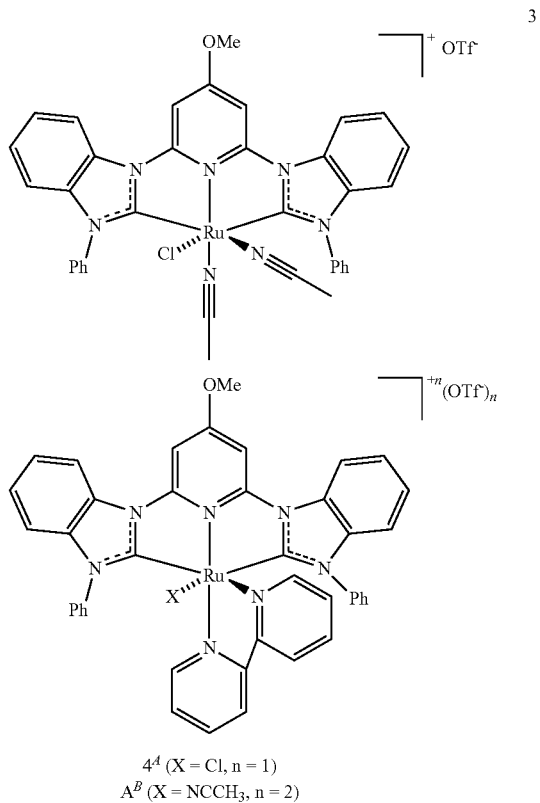

Catalysts of type $1^R$ (as shown in Scheme 2) contain a CNC pincer featuring an imidazole based NHC ring bonded to a pyridine derivative. The advantage of this class of catalysts is the ease of synthetic preparation and the ability to vary the R-group on the pyridine ring. The para position on the pyridine ring (R) can be OMe or H (Boudreaux, C. M., et al., *Chem. Commun.* 2017, 53, 11217-11220) or it can be OH, NMe$_2$ or Me. For catalysts of type $2^R$, the imidazole based NHC ring is replaced with benzimidazole, which weakens the NHC donor strength (Rodrigues, R. R.; et al., *ACS Appl. Energy Mater.* 2019, 2, 37-46; Das, S.; et al., *Inorg. Chem.* 2019, 58 (12), 8012-8020; Boudreaux, C. M.; et al., *Chem. Commun.* 2017, 53, 11217-11220; Gradert, C.; et al., *J. Organomet. Chem.* 2014, 770, 61-68), Complex $2^H$ is previously unreported and was characterized by $^1$H NMR, $^{13}$C NMR, $^{19}$F NMR, MS, and IR methods (as described below). Catalyst 3 builds upon $2^{OMe}$ by replacing methyl wingtips with phenyl wingtips on the NHC rings. Catalysts $4^A$ and $4^B$ increase the coordination number of the ruthenium center and were synthesized by adding 2,2'-bipyridine (bipy) to 3 using a multistep route described previously (Burks, D. B.; et al., *Chem. Commun.* 2018, 54, 3819-3822). Four of these catalysts ($2^{OMe}$, 3, $4^A$, $4^B$) were synthesized and characterized as previously shown (Boudreaux, C. M.; et al., *Chem. Commun.* 2017, 53, 11217-11220). In comparing some these catalysts to each other, the donor strength of the pincer (and extent of metal to ligand backbonding from Ru to NCCH$_3$ by IR spectroscopy) was found to decrease in the order $1^{OMe}$>$2^{OMe}$>3 with the same substituents on Ru and on the pyridine of the pincer. Furthermore, the presence of π donor R groups (e.g., OH, OMe) can result in a more electron rich pincer.

Example 2

Vanillyl alcohol (VA) was used as a surrogate for lignin-derived monomers, and catalytic conversion of VA was carried out as shown in Scheme 3. For all catalysts and conditions studied, the catalytic reaction yielded two major products labeled as A and B in Scheme 3 and ring hydrogenation products were not observed. Product A (creosol) reduces the oxygen content of VA through the desired hydrodeoxygenation reaction. Product B (methyl vanillyl ether) is the alkylation product (Williamson ether synthesis) in methanol solvent and is considered an undesired product as it does not reduce the oxygen content of VA. In fact, control experiments in which the transition metal catalyst was omitted (Table 1, entries 16-17) illustrate that product B can be obtained as the major product readily by treating VA with methanol under hydrogen (290 psi) in the presence of a base (44% yield) or acid (>99% yield). However, no significant yield of product A is obtained without a transition metal catalyst (Table 1, entry 15). ("Cat." Refers to the catalyst structures shown in Scheme 3)

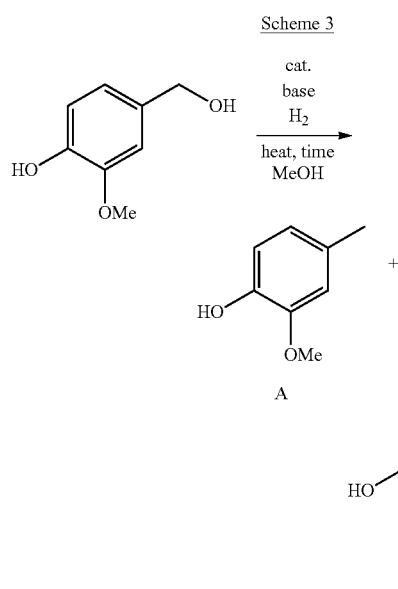

Scheme 3

TABLE 1

Screening Ruthenium Pincer Catalyst for Hydrodeoxygenation of Vanillyl Alcohol[a]

| Entry | Catalyst | % Conv.[b] | Yield of A, (%)[c] | Yield of B, (%)[c] |
|---|---|---|---|---|
| 1 | $1^{OH}$ | 91(1) | 39.1(5) | 52.2(8) |
| 2 | $1^{OMe}$ | 99.9(1) | 30.7(4) | 69.2(4) |
| 3 | $1^{NMe2}$ | 93.6(2) | 24.2(4) | 69.4(3) |
| 4 | $1^{Me}$ | 99.5(4) | 20.9(2) | 78.6(4) |
| 5 | $1^{H}$ | 18.5(4) | 15.0(4) | 1.9(1) |
| 6 | $2^{OMe}$ | 100.0[d] | 16.8(5) | 83.2(5) |
| 7 | $2^{H}$ | 99.98(1) | 16.3(4) | 83.7(4) |
| 8 | 3 | 99.6(1) | 21.4(7) | 78.2(7) |
| 9 | $4^{A}$ | 14(1) | 2(2) | 11(2) |
| 10 | $4^{B}$ | 100.0[d] | 2.1(2) | 97.9(2) |
| 11[e] | $1^{OH}$ | 98.0(4) | 95.8(7) | 0.2(1) |
| 12[e] | $1^{OMe}$ | 92(4) | 88(5) | 3(2) |
| 13[e] | $1^{NMe2}$ | 91(4) | 89(4) | 1.6(3) |
| 14[f] | $1^{NMe2}$ | 100.0[d] | 2(1) | 98(1) |
| 15 | none | 19.0(8) | 1.8(4) | 15.5(7) |
| 16[g] | none | 45.9(4) | 1.9(7) | 43.6(6) |
| 17[f] | none | 100.0[d] | 0.16(9) | 99.95(9) |

[a]All experiments were done in triplicate and analyzed by GC. Estimated standard deviation in the last digit is reported in parentheses. Conditions: 0.0642 M vanillyl alcohol in methanol, 1 mol % of catalyst, 290 psi $H_2$, 100° C. for 1 h.
[b]Conversion is calculated based on starting material consumption.
[c]Yield is calculated from the GC.
[d]Quantitative conversion was observed in all three experiments.
[e]50 mol % $Na_2CO_3$ was added.
[f]1 mol % HOTf was added.
[g]10 mol % $Na_2CO_3$ was added.

Two of the catalysts tested in Table 1 contain acidic ($1^{OH}$) or basic ($1^{NMe2}$) groups, and thus the π donor properties of the ligands can be modified by the addition of external acids or bases (Scheme 4). Entry 11 (Table 1) shows that the presence of a base (50 mol % $Na_2CO_3$) with $1^{OH}$ facilitated the HDO reaction and led to a 96% yield for product A in just 1 hour. Thus, nearly quantitative conversion to A is obtained by deprotonating $1^{OH}$, which enhances the π donor properties of the pincer ligand. Furthermore, $1^{NMe2}$ can be deactivated by protonation of the $NMe_2$ group with acid (entry 14) to generate a cationic pincer ligand bearing a σ withdrawing $NMe_2H^+$ group. The results here look similar to entry 17 in Table 1, illustrating that triflic acid has completely deactivated $1^{NMe2}$. Thus, both $1^{OH}$ and $1^{NMe2}$ are switchable HDO catalysts that can be activated or deactivated by acids and bases (Scheme 4).

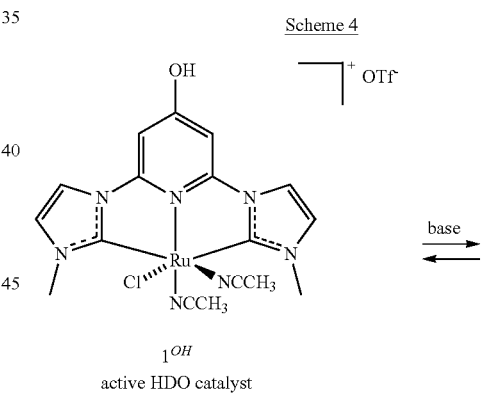

Scheme 4

$1^{OH}$
active HDO catalyst $1^{O-}$
more active HDO catalyst

The addition of base to $1^{OMe}$ and $1^{NMe2}$ was further explored. Without wishing to be bound by any theory, it was assumed that base should not affect the structure of $1^{OMe}$ and thus any changes in observed reactivity would not be attributed to changes in the catalyst. As illustrated by entry 12 of Table 1, using a base with $1^{OMe}$ to generate 88% yield of A showing that the base accelerates the HDO reaction even in the absence of a protic ligand (cf. entry 2 with 31% yield of A). Adding a base to $1^{NMe2}$ would ensure that the basic amino group is neutral (rather than partially protonated) and thus lead to a better π donor group. Entry 13 shows that the addition of base enhances catalysis with $1^{NMe2}$, and an 89% yield of the HDO product is obtained (vs. 24% without base, entry 3). A comparison of these results demonstrated that the selectivity to the desired product is increased with the base present for all three catalysts: $1^R$ where R=OH, OMe, NMe2. This also gives insight into H2 activation reaction, which likely occurs via Ru+H$_2$→Ru—H+H$^+$. Again, without wishing to be bound by any theory, it is speculated that the generation of H$^+$ can be detrimental to the reaction selectivity likely by promoting a Williamson ether synthesis reaction to form the undesired product B. Thus, it was assumed that the base can play two roles: preventing acid build up and undesired pathways, and, when the catalyst is designed properly, the base can further activate the catalyst. However, base alone does not lead to the desired product A (entry 16, Table 1). To further enhance the catalytic activity, the experimental conditions were systematically varied. Increasing reaction temperature did not have a significant effect on reaction selectivity or activity (as shown below). In addition, catalyst decomposition was observed at temperatures>150° C.

Further, the identity and loading of the base were explored (Table 2). It was shown that strong bases such as NaOH and NaOtBu can have a detrimental effect on the reaction (entries 1 and 2). Weak bases, on the other hand, such as Na$_2$CO$_3$, can result in optimal conversion and selectivity at high base loadings (entries 4-9). The use of a very weak base (NaHCO$_3$, entry 3) did not lead to good conversion. It was shown that the quantitative formation of A can be achieved at the conditions where 50 or 100 mol % of Na$_2$CO$_3$ and 1 mol % of $1^{OH}$ are used.

TABLE 2

Hydrodeoxygenation of Vanillyl Alcohol with $1^{OH}$.
Evaluating the Identity and Quantity of Base[a]

| Entry | Base (mol %) | % Conv.[b] | Yield of A, (%)[c] | Yield of B, (%)[c] |
|---|---|---|---|---|
| 1 | NaOtBu (10) | 41.6(4) | 38.1(4) | 1.65(6) |
| 2 | NaOH (10) | 50.8(8) | 47(1) | 2.1(1) |
| 3 | NaHCO$_3$ (10) | 29.2(8) | 27(1) | 0.6(2) |
| 4 | K$_2$CO$_3$ (10) | 51.1(5) | 46.8(6) | 0.8(6) |
| 5 | Na$_2$CO$_3$ (1.1) | 20(2) | 16(2) | 0.5(2) |
| 6 | Na$_2$CO$_3$ (10) | 51(2) | 48(2) | 1.1(2) |
| 7 | Na$_2$CO$_3$ (25) | 73(1) | 69.5(4) | 2(1) |
| 8 | Na$_2$CO$_3$ (50) | 98.0(4) | 95.8(7) | 0.2(1) |
| 9 | Na$_2$CO$_3$ (110) | 99.73(6) | 98.8(3) | 0.4(3) |

[a]All experiments were done in triplicate and analyzed by GC. Estimated standard deviation in the last digit is reported in parentheses. Conditions: 0.0642 M vanillyl alcohol in methanol, 1 mol % of catalyst, 290 psi H$_2$, 100° C. for 1 h.
[b]Conversion is calculated based on starting material consumption.
[c]Yield is calculated from the GC.

As described in detail below, using product B as a substrate and under optimal catalytic conditions (with $1^{OH}$ or $1^{OMe}$ as the catalyst), a slower formation of A can be achieved when compared to the conversion of VA directly to A. Without wishing to be bound by any theory, it was proposed that product B formation does not facilitate the formation of A. Again, without wishing to be bound by any theory, two possibilities were suggested: 1) B must be converted to VA by any adventitious water present before the HDO reaction can occur or alternatively, 2) B goes directly to A, but by a mechanism that is different from that employed when VA is a starting material, and it must be inherently slower. The methylated substrate B is not expected to bind to ruthenium as readily as deprotonated VA.

Once the optimum base loadings were established, a lower catalyst loading of $1^{OH}$ was further investigated to probe whether the catalyst can operate efficiently under very dilute conditions. Without increasing the reaction time beyond one hour, the lowest catalyst loading that results in quantitative conversion to product A was 0.05 mol % (Na$_2$CO$_3$=2.5 mol %, T=150° C., TON=2,000). By lowering the temperature to 100° C., quantitative conversion can be obtained with 0.01 mol % catalyst loading in 3 days (Na$_2$CO$_3$=0.5 mol %, TON=10,000). Surprisingly, an increase in the turnover number of five-fold was achieved. This increase can be further increased at either lower catalyst loadings or longer reaction times. Catalyst $1^{OH}$ performs better than heterogeneous catalysts in the literature which only achieve 90% yield of product A (Hao, P.; et al., *ACS Catal.* 2018, 8 (12), 11165-11173) or which achieve similar results (>99% yield of A and selectivity) but only at much higher (e.g., 5 wt. % for Zn/Pd/C) catalyst loadings (DeLucia, N. A.; et al., *Catal. Today* 2018, 302, 146-150; DeLucia, N. A.; et al., *ACS Catal.* 2019, 9060-9071).

Example 3

For every catalytic system, there is a need to interrogate whether the active catalyst is homogeneous or heterogeneous in nature. To probe this issue for $1^{OH}$, the mercury test, as shown below, was performed. Since mercury is known to coat the surface of nanoparticles, typically a lower activity is observed for heterogeneous systems (Anton, D. R.; et al., *Organometallics* 1983, 2 (7), 855-859; Widegren, J. A.; et al., *J. Am. Chem. Soc.* 2003, 125 (34), 10301-10310; Eberhard, M. R., *Org. Lett.* 2004, 6 (13), 2125-2128).

When entry 8 of Table 2 was repeated with a few drops of mercury added to the reaction vessel, a 95% yield of A by GC was obtained (done in triplicate). Since, within experimental error, this result is the same as entry 8, it was assumed that mercury does not alter the catalytic activity of $1^{OH}$ with 50 mol % Na$_2$CO$_3$ at 100° C. Without wishing to be bound by any theory, it was suggested that this catalyst is homogeneous and molecular under these conditions. It is understood, however, that the nature of the true catalyst in solution is often sensitive to the specific conditions employed, and therefore, caution is needed in deciding the nature of the catalyst (Stracke, J. J.; et al., *ACS Catal.* 2013, 1209-1219; Bayram, E.; et al., *J. Am. Chem. Soc.* 2011, 133 (46), 18889-18902).

Similarly, since the catalyst $1^{OMe}$ with 50 mol % Na$_2$CO$_3$ present (entry 12, Table 1) showed a large run variation in results, the mercury test on this system was performed as well. Similar results of 91(4)% conversion, 88(4)% yield of A, 2(1)% yield of B were obtained. Again, without wishing to be bound by any theory, it was suggested that the variation seen is not due to nanoparticle formation for $1^{OMe}$ with base.

In this study, the electronic properties of ruthenium pincer complexes, along with the ability to provide free sites for substrate binding, were related to the ability for these complexes to function as HDO catalysts. At least one labile site was found to be necessary for any catalytic activity (e.g., for the formation of the methylation product, B) to be observed. Two to three labile ligand sites, however, proved necessary but not sufficient for good yields of the HDO product A. The best yields and selectivity for A were achieved with the most electron rich pincer ligand (1 rather than 2 or 3) with π donor substituents ($1^{NMe2}$, $1^{OMe}$, $1^{OH}$) in the presence of a weak base ($Na_2CO_3$). Under low catalyst loadings (0.01 mol %), $1^{OH}$ in the presence of base serves as a homogeneous catalyst that is able to achieve a quantitative and selective conversion of vanillyl alcohol to the desired HDO product, A.

Example 4

1.1 Synthesis of 2,6-bis(1H-benzo[d]imidazol-1-yl) pyridine (7)

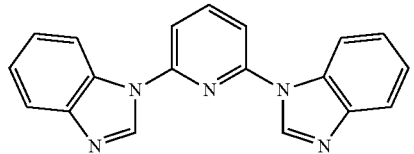

7

The compound was synthesized similarly to the procedures known in the art (Herbst, A.; et al., *Organometallics* 2013, 32, 1807-1814) and according to Scheme 5, as shown below.

NaH (1.014 g, 25.32 mmol, 3.0 eq.) was added to a 3-necked round bottom flask. Under $N_2$, compound 5 (2.89 g, 24.48 mmol, 2.9 eq) in dry DMF (50 mL) was added to the flask. After stirring for 1 hour, compound 6 (2.0 g, 8.44 mmol, 1.0 eq.) was added to the reaction flask and heated overnight at 60° C. Then, the flask was heated at 140° C. for 2 days. The reaction was cooled to room temperature and treated with $H_2O$. A pink to light brown precipitate was collected as the crude product. The crude product was purified by recrystallization in $^iPrOH$, and compound 7 was obtained as pink to white crystal (1.3 g, 49.5% yield). $^1H$ NMR (360 MHz, CDCl3) δ 8.68 (s, 2H), 8.18-8.13 (m, 3H), 7.94-7.91 (m, 2H), 7.60 (d, 2H, $J_{HH}$=8.00 Hz), 7.45-7.40 (m, 2H).

Scheme 5

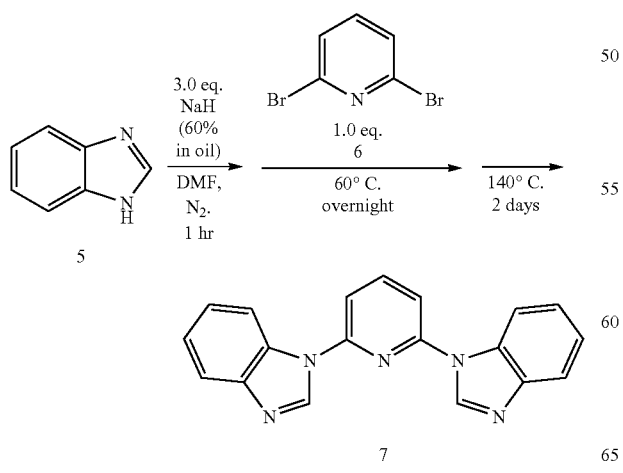

1.2 Synthesis of the Preligand 3,3'-(pyridine-2,6-diyl)bis(1-methyl-1H-benzo[d]imidazol-3-ium) triflate (8)

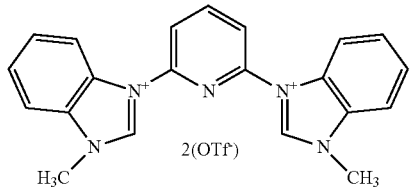

8

Compound 7 (250 mg, 0.803 mmol, 1.0 eq.) was added in a 3-necked round bottom flask with dry DMF. Under $N_2$, MeOTf (0.91 mL, 8.03 mmol, 10.0 eq.) was added drop wisely with stirring at 0° C. The reaction was allowed to warm up to room temperature and stirred overnight at room temperature. The reaction mixture was concentrated under vacuum, then washed with $Et_2O$ for 7 times, followed by washing with DCM for 7 times. Ligand 8, according to Scheme 6, was obtained as a pure white powder (253.6 mg, 49.4%). $^1H$ NMR (360 MHz, DMSO, ppm)[3] δ 10.59 (s, 2H), 8.75 (t, 1H, $J_{HH}$=8.03 Hz), 8.44 (d, 2H, $J_{HH}$=8.19 Hz), 8.29 (d, 2H, $J_{HH}$=8.08 Hz), 8.20 (d, 2H, $J_{HH}$=8.22 Hz), 7.84 (t, 2H, $J_{HH}$=7.45 Hz), 7.76 (t, 2H, $J_{HH}$=8.07 Hz), 4.27 (s, 6H); $^{19}F$ NMR (339 MHz, DMSO, ppm) δ 77.75.

Scheme 6

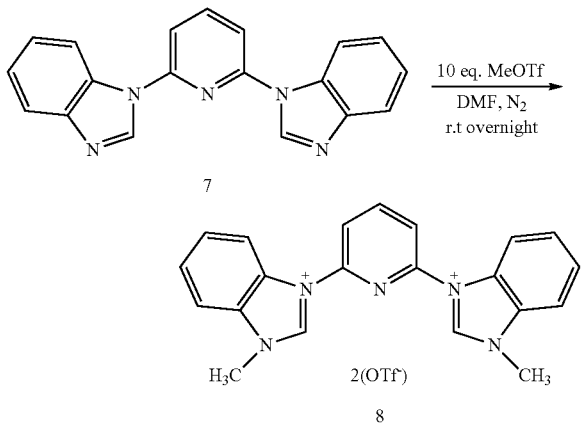

1.3 Synthesis of Catalyst $2^H$

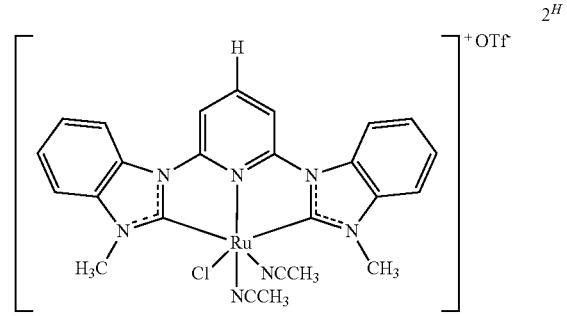

[CymRuCl2]2 (25 mg, 0.0408 mmol, 1.0 eq.), ligand 8 (49.6 mg, 0.0776 mmol, 1.9 eq.), and MeCN (5 mL) were added to a 3-necked round bottom flask in glovebox. After sealing and moving the flask out of the glovebox, Et$_3$N (0.114 mL, 0.816 mmol, 20.0 eq.) was added to the flask by using a syringe and needle. The flask was then purged with N$_2$. The reaction mixture was heated with stirring at 60° C. for 24 hours. After cooling to room temperature, the liquid was separated from the solid crude product. The solid was washed by using Et$_2$O for 3 times. The combined liquid was diluted with Et$_2$O to recover more product. Catalyst 2$^H$, according to Scheme 7, was obtained as bright yellow solid (30.8 mg, 64.9%). $^1$H NMR (500 MHz, DMSO, ppm) δ 8.49 (d, 2H, J$_{HH}$=7.83 Hz), 8.36 (d, 2H, J$_{HH}$=8.26 Hz), 8.17 (t, 1H, J$_{HH}$=8.26 Hz), 7.97 (d, 2H, J$_{HH}$=8.04 Hz), 7.65-7.58 (m, 4H), 4.42 (s, 6H), 2.86 (s, 3H), 2.05 (s, 3H); {$^1$H}$^{13}$C NMR (126 MHz, DMSO, ppm) δ 207.25, 155.61, 139.90, 136.10, 131.27, 128.55, 124.62, 124.38, 124.10, 111.79, 111.71, 106.69, 34.21, 3.77, 3.61; $^{19}$F NMR (339 MHz, DMSO, ppm) δ 77.75. HRMS (ESI) calculated for C$_{21}$H$_{17}$N$_5$ClRu (M-triflate-2×MeCN): 476.0216, found 476.0216. FT-IR (ATR, cm$^{-1}$): 3564.16, 3117.62, 2985.62, 2927.87, 2274.85, 1618.54, 1594.06, 1569.22, 1479.49, 1437.82, 1393.25, 1363.34, 1326.67, 1255.32, 1223.16, 1187.31, 1160.60, 1146.53, 1091.85, 1028.56, 959.65, 927.18, 870.73, 842.88, 809.68, 781.10, 743.53, 733.24, 678.09, 636.97, 573.87, 548.26, 516.80, 459.22, 431.61.

Scheme 7

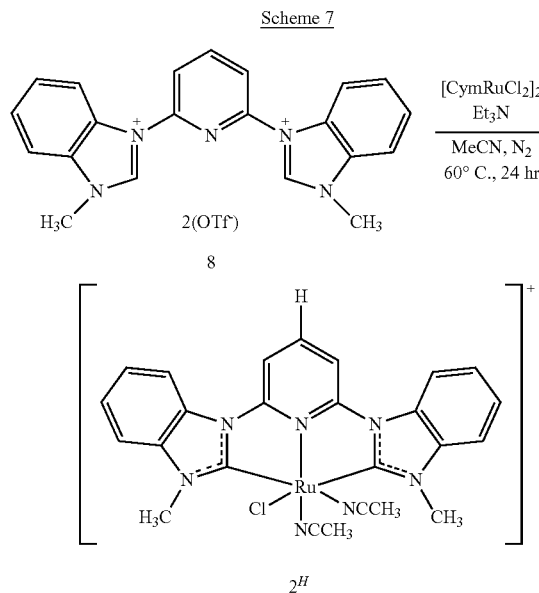

1.4 General Procedures

To a 20 mL vial with a stir bar, 1$^{OH}$ (2 mg, 0.00321 mmol), vanillyl alcohol (49.5 mg, 0.321 mmol), and Na$_2$CO$_3$ (8.5 mg, 0.08025 mmol), were added. Methanol (5 mL) was injected into the vial by using a syringe and needle right before placing the vial in the Parr vessel. The reaction vial was semi submerged into about 350 mL methanol in a Parr vessel, which contained a metal frame to support the reaction vessel and stir bar at the bottom. The Parr vessel was sealed and purged with ultra-high purity H2 gas for 5 times. The Parr vessel was then pressurized to 290 psi (20 bar) and heated at 100° C. with stirring for 1 hr. After heating was completed, the Parr vessel was cooled with a water-ice bath to about 40° C. After releasing the pressure, a sample was taken from the reaction mixture for GC analysis.

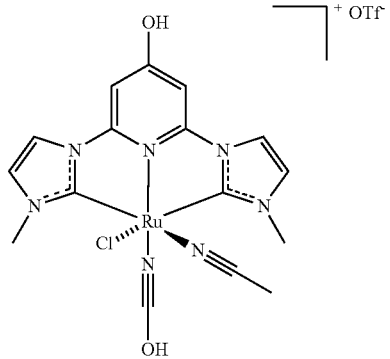

1.5 Method for Gas Chromatography

1 μL of the sample was injected into the inlet at 250° C. with pressure 27.8 psi. ⅒ of the sample was split into the column with a flow rate of 3.0 mL/min and pressure 27.8 psi. The column was kept at 80° C. for 1 min, then heated to 200° C. with a heating ramp rate of 15° C./min. The temperature was held for 2 min after reaching 200° C.

1.4 Optimizing the Catalyst Loading at 4 h Reaction Time

As shown in Table 3, a substantially quantitative conversion can still be maintained at 2.5 mol %. At 1 mol %, it is not a quantitative conversion, but it leaves room for optimization. Therefore, 1 mol % was used for further optimization.

TABLE 3

Hydrodeoxygenation of Vanillyl Alcohol with 1$^{OH}$ and Na$_2$CO$_3$: Optimize Catalyst Loading at 4 h Reaction Time.[a]

| Entry | Amount of 1$^{OH}$ | Amount of Na$_2$CO$_3$ | % Conv.[b] | Yield of A, (%)[c] | Yield of B, (%)[c] |
|---|---|---|---|---|---|
| 1 | 5 mol % | No base | 74.7(2) | 59(3) | 14(2) |
| 2 | 5 mol % | 50 mol % | 99(1) | 96(2) | 1(2) |
| 3 | 2.5 mol % | 25 mol % | 99.65(4) | 97.4(5) | 0.8(6) |
| 4 | 1 mol % | 10 mol % | 86(3) | 81(1) | 3(3) |

[a]All experiments were done in triplicate and analyzed by GC. Conditions: vanillyl alcohol in methanol (0.0128 M for entries 1-2 and 0.0257 M for entry 3, and 0.0624M for entry 4), 290 psi H$_2$, 100° C. for 4 h. 1:10 catalyst to base ration was kept for entries 2-4.
[b]Conversion is calculated based on starting material consumption.
[c]Yield is calculated from the GC.

1.5 Optimizing the Reaction Temperature

As shown in Table 4, the substantially quantitative conversion was observed for reaction temperature above 150° C. However, the unusual color change of the reaction solution was observed for temperature above 160° C. Without wishing to be bound by any theory, it is believed that such change can be caused by catalyst decomposition. To avoid the changes in color, the temperature of 150° C. was chosen for further testing.

TABLE 4

Hydrodeoxygenation of Vanillyl Alcohol with $1^{OH}$ and $Na_2CO_3$: Optimize the Reaction Temperature.[a]

| Entry | Temperature | % Conv.[b] | Yield of A, (%)[c] | Yield of B, (%)[c] |
|---|---|---|---|---|
| 1 | 100° C. | 73(1) | 69.5(4) | 3(1) |
| 2 | 120° C. | 99.97(1) | 99.77(2) | 0.20(2) |
| 3 | 150° C. | 100.0[d] | 100.0[d] | 0[e] |
| 4 | 160° C. | 100.0[d] | 100.0[d] | 0[e] |
| 5 | 180° C. | 100.0[d] | 100.0[d] | 0[e] |

[a]All experiments were done in triplicate and analyzed by GC. Conditions: 0.0642 M vanillyl alcohol in methanol, 1 mol % $1^{OH}$, 25 mol % $Na_2CO_3$, 290 psi $H_2$, for 1 h.
[b]Conversion is calculated based on starting material consumption.
[c]Yield is calculated from the GC.
[d]Quantitative conversion was observed in all three experiments.
[e]No peak was observed in all three experiments.

1.6 Hydrodeoxygenation of Methyl Vanillyl Ether (Scheme 8)

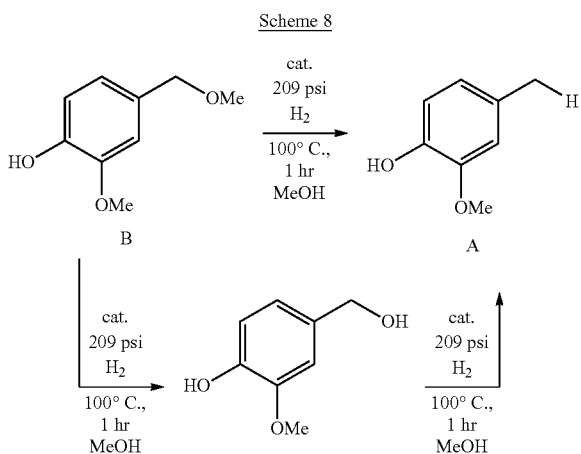

Scheme 8

Experiments were done for this deoxygenation reaction by using compound B as starting material, the reaction conditions are shown in Table 5. Some product A generation was observed for the experiments. Based on these observations, and without being bound by any theory, it was hypothesized that a low selectivity obtained by using other catalysts is because catalysts other than $1^{OH}$ with base have either poor ability to convert product B to product A or have poor ability to convert product B back to starting material for deoxygenation reaction. In addition, increasing base loading doesn't enhance the product A generation from product B, but can enhance conversion from vanillyl alcohol to product A. This may suggest higher base loading facilitates the catalysis from vanillyl alcohol, which reduces the reaction time and allows less amount of product B generation.

TABLE 5

Experimental Conditions for Hydrodeoxygenation of Methyl Vanillyl Ether[a]

| Entry | Conditions | Yield of A (%)[b] |
|---|---|---|
| 1 | $1^{OH}$ 1 mol % with $Na_2CO_3$ 25 mol % | 50(1) |
| 2 | $1^{OH}$ 1 mol % with $Na_2CO_3$ 50 mol % | 60.4(8) |

TABLE 5-continued

Experimental Conditions for Hydrodeoxygenation of Methyl Vanillyl Ether[a]

| Entry | Conditions | Yield of A (%)[b] |
|---|---|---|
| 3 | $1^{OH}$ 1 mol % with no base | 12.6(3) |
| 4 | $1^{OMe}$ 1 mol % with no base | 15.4(8) |

[a]All experiments were done in triplicate and analyzed by GC. Conditions: 0.0642 M methyl vanillyl ether in methanol, 1 mol % $1^{OH}$, 25 mol % $Na_2CO_3$, 290 psi $H_2$, for 1 h.
[b]Yield is calculated from the GC.

1.7 Tests Using Solids (Mostly $Na_2CO_3$) Leftover from Catalysis

As shown in Table 6 below, the use of $1^{OMe}$ as a catalyst resulted in high variability of results (see entry 1, Table 6 below, which shows a relatively high standard deviation in % conversion and product yields). Without wishing to be bound by any theory, it was speculated that the solid $Na_2CO_3$ could provide a support for a heterogeneous catalyst. To test this hypothesis, the solids leftover from a catalytic run (which are mostly $Na_2CO_3$) were isolated. These solids were tested as a catalyst (entry 2, Table 6). However, a low % yield of A was achieved, suggesting that these solids are not active in the formation of A. Some base-driven formation of B does occur, as is observed for $Na_2CO_3$ generally.

General Procedure:

To a 20 mL vial with a stir bar, $1^{OMe}$ (2 mg, 0.00321 mmol), vanillyl alcohol (49.5 mg, 0.321 mmol), and $Na_2CO_3$ (8.5 mg, 0.08025 mmol) were added. Methanol (5 mL) was injected into the vial by using a syringe and needle right before placing the vial in the Parr vessel. The reaction vial was semi-submerged into about 350 mL methanol in a Parr vessel, which contains a metal frame to support the reaction vessel and stir bar at the bottom. The Parr vessel was sealed and purged with ultra-high purity $H_2$ gas for 5 times. The Parr vessel was then pressurized to 290 psi (20 bar) and heated at 100° C. with stirring for 1 hr. After heating was completed, the Parr vessel was cooled with a water-ice bath to about 40° C. After releasing the pressure, a sample was taken from the reaction mixture for GC analysis. The reaction mixture was then filtered through Celite contained in a filter pipet. The solid with Celite was washed with 1 mL MeOH twice and dried by air briefly, and was transferred to a new 20 mL vial with a stir bar. Vanillyl alcohol (49.5 mg, 0.321 mmol) was added to the vial. Methanol (5 mL) was injected into the vial by using a syringe and needle right before placing the vial in the Parr vessel. The reaction vial was semi-submerged into about 350 mL methanol in a Parr vessel, which contains a metal frame to support the reaction vessel and stir bar at the bottom. The Parr vessel was sealed and purged with ultra-high purity H2 gas 5 times. The Parr vessel was then pressurized to 290 psi (20 bar) and heated at 100° C. with stirring for 1 hr. After heating was completed, the Parr vessel was cooled with a water-ice bath to about 40° C. After releasing the pressure, a sample was taken from the reaction mixture for GC analysis.

TABLE 6

Tests Using Solids Leftover from Catalysis.[a]

| Entry | Catalyst | % Conv.[d] | Yield of A, (%)[e] | Yield of B, (%)[e] |
|---|---|---|---|---|
| 1[b] | $1^{OMe}$ | 92(4) | 88(5) | 3(2) |
| 2[c] | Solid from entry 1 | 47.69(3) | 4(2) | 43.2 (2) |

[a]All experiments were done in triplicate and analyzed by GC. Conditions: 0.0642 M vanillyl alcohol in methanol, 290 psi $H_2$, for 1 h.
[b]1 mol % $1^{OMe}$, 50 mol % $Na_2CO_3$.
[c]Solid material (mostly $Na_2CO_3$) was isolated from a reaction in entry 1 by filtering thru Celite.
[d]Conversion is calculated based on starting material consumption.
[e]Yield is calculated from the GC.

1.8 Mercury Test to Probe Homogeneous vs. Heterogeneous Catalysis

General Procedure: To a 20 mL vial with a stir bar, $1^{OH}$ (2 mg, 0.00321 mmol), vanillyl alcohol (49.5 mg, 0.321 mmol), and $Na_2CO_3$ (8.5 mg, 0.08025 mmol) were added. A few drops of Hg were added to the vial by using a pipet. Methanol (5 mL) was injected into the vial by using a syringe and needle right before placing the vial in the Parr vessel. The reaction vial was semi-submerged into about 350 mL methanol in a Parr vessel, which contains a metal frame to support the reaction vessel and stir bar at the bottom. The Parr vessel was sealed and purged with ultra-high purity $H_2$ gas for 5 times. The Parr vessel was then pressurized to 290 psi (20 bar) and heated at 100° C. with stirring for 1 hr. After heating was completed, the Parr vessel was cooled with a water-ice bath to about 40° C. After releasing the pressure, a sample was taken from the reaction mixture for GC analysis. The results are shown in Table 7.

TABLE 7

Hg Tests for the Catalysis.[a]

| Entry | Catalyst | % Conv.[b] | Yield of A, (%)[c] | Yield of B, (%)[c] |
|---|---|---|---|---|
| 1 | $1^{OH}$ | 91.7(8) | 40.3(7) | 50.9(1) |
| 2[d] | $1^{OH}$ | 98.3(6) | 95(1) | 2.9(4) |
| 3 | $1^{OMe}$ | 99.94(1) | 24(2) | 76(2) |
| 4[d] | $1^{OMe}$ | 91(4) | 88(4) | 2(1) |

[a]All experiments were done in triplicate and analyzed by GC. Conditions: 0.0642 M vanillyl alcohol in methanol, 1 mol % of the catalyst listed above, a few drops of Hg, 290 psi $H_2$, for 1 h.
[b]Conversion is calculated based on starting material consumption.
[c]Yield is calculated from the GC.
[d]50 mol % $Na_2CO_3$ were added.

Example 5

General Considerations:

All the syntheses are done as described here. Reactions are prepared and performed under an inert atmosphere ($N_2$) using glovebox or Schlenk line techniques using oven dried glassware unless otherwise stated. Work up and purifications are done open to the air. 2,6-difluoro-N,N-dimethylpyridin-4-amine was synthesized following a literature procedure (Schlosser, M.; Bobbio, C.; Rausis, T., *The Journal of Organic Chemistry* 2005, 70 (7), 2494-2502). 2,6-difluoro-pyridin-3-ol was isolated as minor product while synthesizing 2,6-difluoro-pyridin-4-ol form 2,6-difluoropyridine (Scheme 13).

Solvents and Reagents:

Dry solvents (either commercial or dried on a glass contour solvent purification system built by Pure Process Technology, LLC) are used for reactions unless described otherwise. Reagent grade solvents are used for workup and purification. All the reagents are used as received from the commercial supplier without further purification.

Instruments and Services:

NMR spectra are recorded in a Bruker AVANCE 360 (360 MHz, $^1H$ frequency) or AVANCE 500 (500 MHz, $^1H$ frequency) NMR spectrometer. FT-IR spectra are recorded in a Bruker Alpha ATR-IR spectrophotometer. Mass spectra are obtained in a Waters AutoSpec-Ultima NT mass spectrometer or Waters Xero G2-XS QTOF. Elemental analyses are done by Atlantic Microlab, Inc.

NMR Chemical Shift Reference:

$^1H$ and $\{^1H\}^{13}C$ chemical shifts are assigned with respect to the residual peaks from deuterated NMR solvents (Gottlieb, H. E.; Kotlyar, V.; Nudelman, A., *The Journal of Organic Chemistry* 1997, 62 (21), 7512-7515). No reference is used for $^{19}F$ chemical shifts, only the number of peaks are checked.

Figure 2:
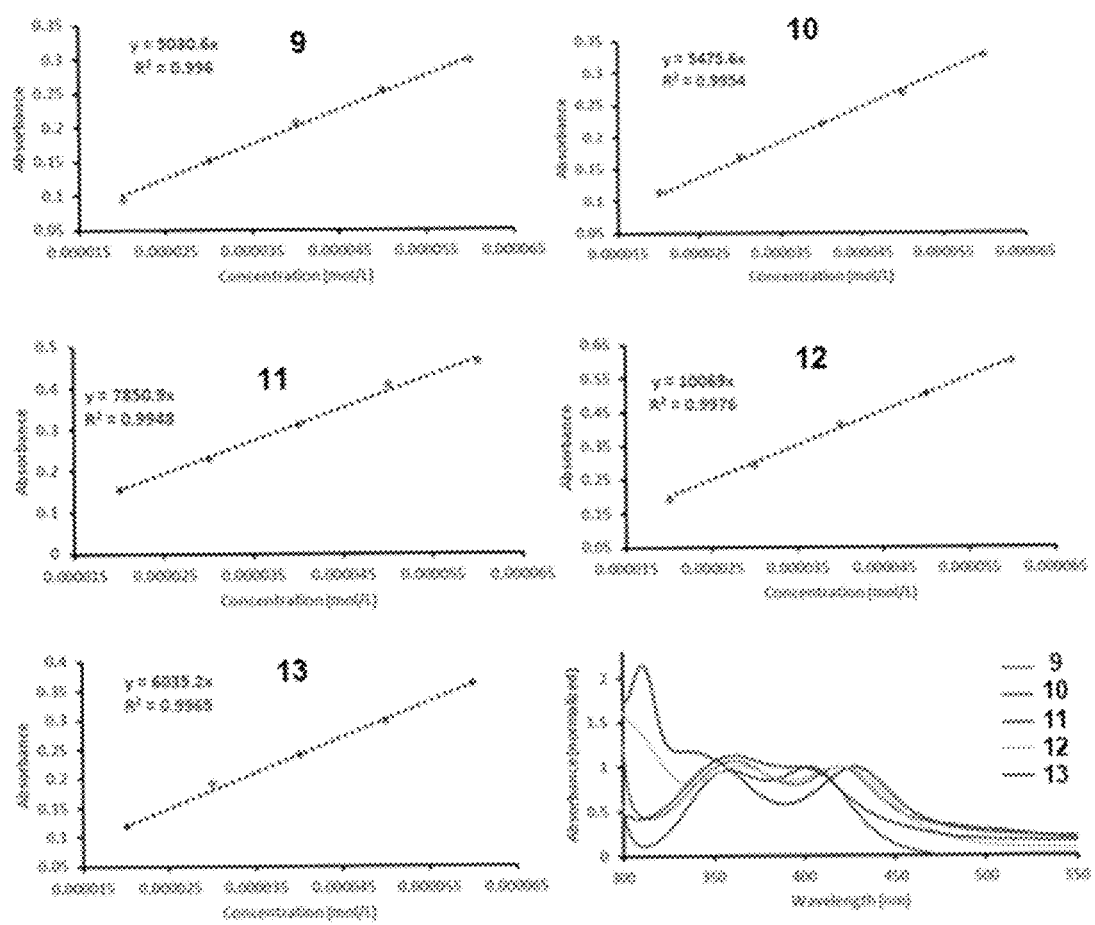
FIG. 2 depicts a Beer's law and normalized absorption spectra in acetonitrile for compounds 9, 10, 11 (same as $1^{Nme2}$), 12, and 13 (same as $1^{OH}$).

SC-XRD Structure Determination:

Complexes 9, 10, 13 (same as $1^{OH}$) and 13e: Single crystals of appropriate dimension were mounted on a Mitgen cryoloop in a random orientation. Preliminary examination and data collection were performed on a Bruker Apexll CCD-based X-ray diffractometer equipped with an Oxford N-Helix Cryosystem low temperature device and a fine focus Mo-target X-ray tube (λ=0.71073 Å) operated at 1500 W power (50 kV, 30 mA). The X-ray intensities were measured at low temperature (223 (2) K). The collected frames were integrated with the Saint (Bruker Saint Plus, Saint Plus 8.34 A; Bruker AXS Inc.: Madison, Wisconsin, USA, 2007) software using a narrow-frame algorithm. Data were corrected for absorption effects using the multi-scan method in SADABS (Bruker *SADABS, TWINABS*, SADABS 2012/1; Bruker AXS Inc.: Madison, Wisconsin, USA, 2001). The space groups were assigned using XPREP of the Bruker ShelXTL (Sheldrick, G. M., *Acta Crystallographica Section A* 2008, 64 (1), 112-122) package, solved with ShelXT (Sheldrick, G. M., *Acta Crystallographica Section A* 2008, 64 (1), 112-122 and refined with ShelXL (Sheldrick, G. M., *Acta Crystallographica Section A* 2008, 64 (1), 112-122) and the graphical interface ShelXle (Hübschle, C. B.; Sheldrick, G. M.; Dittrich, B., *J. Appl. Cryst.* 2011, 44, 1281-1284.) and Olex2 (Dolomanov, O. V.; Bourhis, L. J.; Gildea, R. J.; Howard, J. A. K.; Puschmann, H., *J. Appl. Crystallogr.* 2009, 42 (2), 339-341). All non-hydrogen atoms were refined anisotropically. H atoms attached to carbon were positioned geometrically and constrained to ride on their parent atoms. Specific structure determination details are listed in Tables 8-11. Molecular diagrams of complexes 9, 10, 11 (same as $1^{NMe2}$), 12, 13e, and 13 (same as $1^{OH}$) based on crystallographic data with hydrogen atoms (except for H-bonded one in 13) and counter-anions removed for clarity shown in FIG. 1. The adherence to Beer's law and normalized absorption spectra in acetonitrile for compounds 9, 10, 11 (same as $1^{NMe2}$), 12, and 13 (same as $1^{OH}$) is shown in FIG. 2.

TABLE 8

Comparison of selected bond lengths ((in Å) in Ru-CNC pincer complexes - 9, 10, 11 ($1^{NMe2}$), 12, 13e, and 13.

| | Ru-$C_{avg.}$ | Ru-$N_{py}$ | Ru-Cl |
|---|---|---|---|
| Complex 9 | 2.062(2) | 1.997(2) | 2.4108(6) |
| Complex 10 | 2.061(7) | 1.991(3) | 2.426(1) |

TABLE 8-continued

Comparison of selected bond lengths ((in Å) in Ru-CNC pincer complexes - 9, 10, 11 ($1^{NMe2}$), 12, 13e, and 13.

|  | Ru-C$_{avg.}$ | Ru-N$_{py}$ | Ru-Cl |
|---|---|---|---|
| Complex 11 | 2.069(4) | 1.999(3) | 2.407(1) |
| Complex 12 | 2.057(4) | 1.998(2) | 2.4321(6) |
| Complex 13e | 2.051(4) | 1.999(3) | 2.430(2) |
| [a]Complex 13 | 2.048(5) | 1.999(9) | 2.428(4) |

[a]average of pyridinol and pyridinone units.

TABLE 9

Selected metric parameters for the crystal structures of complexes 9 and 10.

|  | Complex 9 | Complex 10 |
|---|---|---|
| Crystal data |  |  |
| Chemical formula | C$_{18}$H$_{21}$ClN$_7$RU·CF$_3$SO$_3$ | C$_{18}$H$_{21}$N$_7$OClRU·CF$_3$SO$_3$ |
| M$_r$ | 621.01 | 637.01 |
| Crystal System, Space group | Monoclinic, P2$_1$/c | Monoclinic, P2$_1$/c |
| Temperature (K) | 223 K | 223 |
| Unit cell dimensions | a = 13.7319 (5) Å<br>b = 23.7671 (8) Å<br>β = 95.596 (2)°<br>c = 7.9901 (3) Å | a = 12.8858 (12) Å<br>b = 25.125 (2) Å<br>β = 107.037 (4)°<br>c = 8.2567 (8) Å |
| V(Å$^3$) | 2595.28 (16) | 2555.8 (4) |
| Z | 4 | 4 |
| Radiation type | Mo K$_\alpha$ radiation, λ = 0.71073 Å | Mo K$_\alpha$ radiation, λ = 0.71073 Å |
| μ(mm$^{-1}$) | 0.84 | 0.86 |
| Crystal size (mm × mm × mm) | 0.23 × 0.20 × 0.03 | 0.13 × 0.09 × 0.03 |
| Data collection |  |  |
| Diffractometer | Bruker AXS SMART APEX2 CCD diffractometer | Bruker AXS SMART APEX2 CCD diffractometer |
| Absorption correction | Multi-scan | Multi-scan |
|  | SADABS V2012/1 (Bruker AXS Inc) | SADABS V2012/1 (Bruker AXS Inc) |
| No. of measured, independent and observed [with I > 2σ(I)] reflections | 74994<br>7026<br>5916 | 46079<br>6321<br>5382 |
| R$_{int}$ | 0.041 | 0.049 |
| θ$_{max}$, θ$_{min}$ | 29.4°, 1.7° | 28.3°, 2.3° |
| Refinement |  |  |
| R [F$^2$ > 2σ(F$^2$)] | 0.032 | 0.059 |
| wR(F$^2$) | 0.084 | 0.124 |
| S | 1.03 | 1.19 |
| No. of reflections | 7026 | 6321 |
| No. of parameters | 321 | 403 |
| No. of restraints | 0 | 117 |
| H-atom treatment | Constrained | Constrained |
| Δρ$_{max}$, Δρ$_{min}$ (e Å$^{-3}$) | 0.69, −0.59 | 1.01, −0.71 |

TABLE 10

Selected metric parameters for the crystal structures of complexes 11 (same as $1^{NMe2}$) and 12.

|  | Complex 11 (same as $1^{NMe2}$) | Complex 12 |
|---|---|---|
| Crystal data |  |  |
| Chemical formula | (C$_{19}$H$_{24}$N$_8$ClRu)·(CF$_3$SO$_3$) | C$_{29}$H$_{28}$N$_8$ClRu·CF$_3$O$_3$ |
| M$_r$ | 650.05 | 774.18 |
| Crystal System, Space group | Orthorhombic, Pbcn | Monoclinic, P2$_1$/n |
| Temperature (K) | 223 K | 101 (2) |
| Unit cell dimensions | a = 16.922 (3) Å<br>b = 12.696 (2) Å<br>c = 24.854 (4) Å | a = 8.40020 (14) Å<br>b = 30.6074 (6) Å<br>β = 96.9584 (17)°<br>c = 12.1466 (2) Å |
| V(Å$^3$) | 5339.7 (15) | 3099.99 (10) |
| Z | 8 | 4 |
| Radiation type | Mo K$_\alpha$ radiation, λ = 0.71073 Å | Mo K$_\alpha$ radiation, λ = 0.71073 Å |
| μ(mm$^{-1}$) | 0.83 | 0.725 |
| Crystal size (mm × mm × mm) | 0.10 × 0.07 × 0.07 | 0.18 × 0.071 × 0.052 |
| Data collection |  |  |
| Diffractometer | Bruker AXS SMART APEX2 CCD diffractometer | XtaLAB, Synergy R, DW System, HyPix diffractometer |
| Absorption correction | Multi-scan | Numerical & Empirical |
|  | SADABS V2012/1 (Bruker AXS Inc) | CrysAlisPro 1.171.40.53 |
| No. of measured, independent and observed [with I > 2σ(I)] reflections | 184351<br>8196<br>5501 | 46197<br>9052<br>7649 |
| R$_{int}$ | 0.070 | 0.0477 |
| θ$_{max}$, θ$_{min}$ | 30.6°, 1.6° | 30.034°, 2.150° |
| Refinement |  |  |
| R [F$^2$ > 2σ(F$^2$)] | 0.056 | 0.0423 |
| wR(F$^2$) | 0.190 | 0.0931 |
| S | 1.08 | 1.056 |
| No. of reflections | 8196 | 9052 |
| No. of parameters | 340 | 428 |
| No. of restraints | 0 | 0 |
| H-atom treatment | Constrained | Constrained |
| Δρ$_{max}$, Δρ$_{min}$ (e Å$^{-3}$) | 2.32, −1.33 | 1.38, −1.07 |

TABLE 11

Selected metric parameters for the crystal structures of complexes 13 (same as $1^{OH}$) and 13e.

|  | Complex 13e | Complex 13 (same as $1^{OH}$) |
|---|---|---|
| Crystal data |  |  |
| Chemical formula | C$_{24}$H$_{25}$ClN$_7$ORu·CF$_3$SO$_3$ | C$_{17}$H$_{18}$ClN$_7$ORu.C$_{17}$H$_{19}$ClN$_7$O·CF$_3$SO$_3$·2(C$_2$H$_3$N)·C$_2$N |
| M$_r$ | 713.10 | 1216.02 |
| Crystal System, Space group | Triclinic, P−1 | Triclinic, P−1 |
| Temperature (K) | 223 K | 223 K |
| Unit cell dimensions | a = 8.339 (5) Å<br>α = 96.546 (7)°<br>b = 13.091 (7) Å<br>β = 102.773 (7)°<br>c = 14.232 (8) Å<br>γ = 101.947 (7)° | a = 13.474 (4) Å<br>α = 119.411 (4)°<br>b = 15.275 (4) Å<br>β = 110.445 (4)°<br>c = 15.370 (4) Å<br>γ = 93.344(4)° |

TABLE 11-continued

Selected metric parameters for the crystal structures of complexes 13 (same as $1^{OH}$) and 13e.

| | Complex 13e | Complex 13 (same as $1^{OH}$) |
|---|---|---|
| V(Å$^3$) | 1461.4 (14) | 2477.6 (12) |
| Z | 2 | 2 |
| Radiation type | Mo K$_\alpha$ radiation, $\lambda$ = 0.71073 Å | Mo K$_\alpha$ radiation, $\lambda$ = 0.71073 Å |
| u(mm-1) | 0.76 | 0.83 |
| Crystal size (mm × mm × mm) | 0.06 × 0.05 × 0.02 | 0.06 × 0.04 × 0.02 |
| Data collection | | |
| Diffractometer | Bruker AXS SMART APEX2 CCD diffractometer | Bruker AXS SMART APEX2 CCD diffractometer |
| Absorption correction | Multi-scan | Multi-scan |
| | SADABS V2012/1 (Bruker AXS Inc) | SADABS V2012/1 (Bruker AXS Inc) |
| No. of measured, independent and | 39958 | 64866 |
| observed [with $I > 2\sigma(I)$] reflections | 6521 5304 | 10348 5898 |
| $R_{int}$ | 0.065 | 0.139 |
| $\theta_{max}$, $\theta_{min}$ | 27.3°, 1.5° | 26.6°, 1.6° |
| Refinement | | |
| R [$F^2 > 2\sigma(F^2)$] | 0.038 | 0.079 |
| wR($F^2$) | 0.087 | 0.250 |
| S | 1.05 | 1.04 |
| No. of reflections | 6521 | 10348 |
| No. of parameters | 383 | 584 |
| No. of restraints | 0 | 1 |
| H-atom treatment | Constrained | Mixture of Independent and Constrained |
| $\Delta\rho_{max}$, $\Delta\rho_{min}$ (e Å$^{-3}$) | 0.59, -0.75 | 1.85, -1.58 |

Complex 10 was found to have two components disorder at the CF$_3$SO$_3^-$ counter-anion. Restraints were applied onto one of the disordered components to make sure all atoms have similar U$_{ij}$ components (SIMU). SADI was also applied to make sure within the triflate moiety, all bonds are sensible and similar bonds have similar distances. SAME was used to make sure respective disordered moieties have similar geometries. All the atoms were subjected to rigid bond restraint (RIGU).

Complex 12: A suitable crystal was selected and mounted on a Mitegen cryoloop in a random orientation on an XtaLAB Synergy R, DW system, HyPix diffractometer. The crystal was kept at 101(2) K during data collection. Using Olex2 (Dolomanov, 0. V.; Bourhis, L. J.; Gildea, R. J.; Howard, J. A. K.; Puschmann, H., *J. Appl. Crystallogr.* 2009, 42 (2), 339-341), the structure was solved with the ShelXT (Sheldrick, G., *Acta Crystallographica Section C* 2015, 71 (1), 3-8.) structure solution program using Intrinsic Phasing and refined with ShelXL (Sheldrick, G., *Acta Crystallographica Section C* 2015, 71 (1), 3-8_refinement package using Least Squares minimization using either Olex2 (Dolomanov, O. V.; Bourhis, L. J.; Gildea, R. J.; Howard, J. A. K.; Puschmann, H., *J. Appl. Crystallogr.* 2009, 42 (2), 339-341) or ShelXle (Hübschle, C. B.; Sheldrick, G. M.; Dittrich, B., *J. Appl. Cryst.* 2011, 44, 1281-1284) or both.

Synthesis of Complex 9

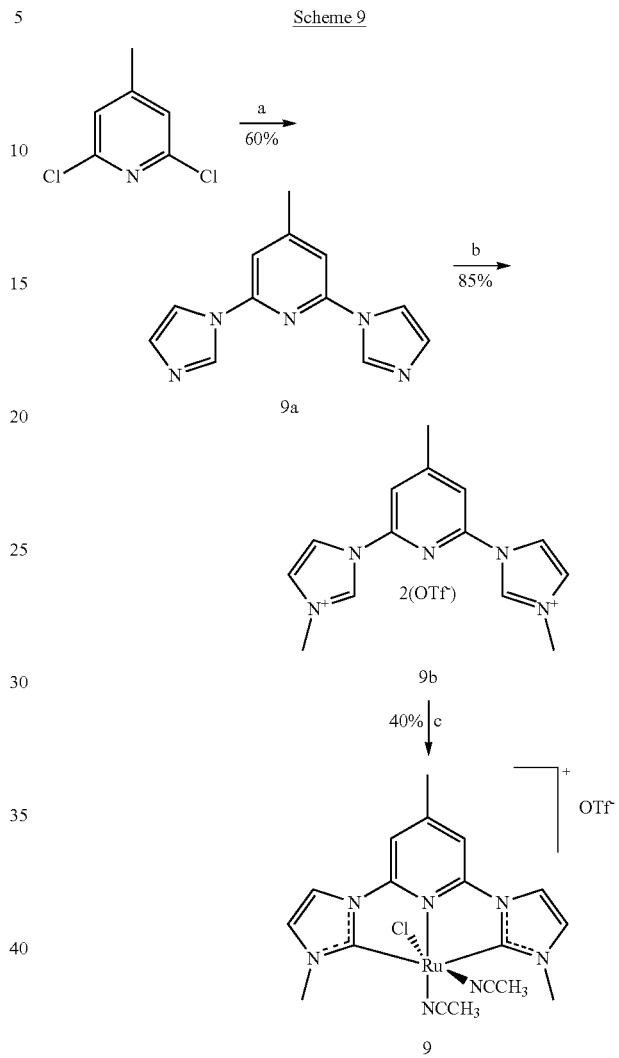

Scheme 9

*(a) 1H-imidazole, K$_2$CO$_3$, DMF;
(b) methyl trifluoromethanesulfonate, DMF; and
(c) [{Ru(p-Cym)Cl$_2$}$_2$], triethylamine, acetonitrile.

2,6-di(1H-imidazol-1-yl)-4-methylpyridine (9a)

A Schlenk flask was loaded with 2,6-dichloro-4-methylpyridine (1.0 g, 6.172 mmol, 1.0 equiv.), 1H-imidazole (0.924 g, 13.578 mmol, 2.2 equiv.), K$_2$CO$_3$ (3.412 g, 24.688 mmol, 4.0 equiv.) and a stir-bar. The flask was filled with DMF (20 mL) from SPS. Then the flask was connected to a Schlenk line under N$_2$ and sealed with a rubber septum. The reaction mixture was stirred while heating at 100° C. for two days. After cooling to room temperature, the reaction mixture was diluted with ice-cooled water (20 mL) and extracted with ethyl acetate (3×50 mL). Combined ethyl acetate part was washed with brine, dried over anhydrous MgSO$_4$, filtered and concentrated to get the crude product. Crude was purified by column (silica gel) chromatography using 0-10% methanol in dichloromethane as eluent to obtain the product (9a) as white solid (0.834 g, 3.703 mmol) with 60% yield. $^1$H-NMR (CDCl$_3$, 500 MHz, ppm): δ 8.31

(apparently singlet, 2H); 7.60 (apparently singlet, 2H); 7.16 (apparently singlet, 2H); 7.06 (s, 2H); 2.48 (s, 3H). {$^1$H}$^{13}$C-NMR (CDCl$_3$, 126 MHz, ppm): δ 154.42, 148.55, 135.23, 131.16, 116.36, 110.69, 21.84.

1,1'-(4-methylpyridine-2,6-diyl)bis(3-methyl-1H-imidazol-3-ium)triflate (9b)

A Schlenk flask was loaded with 2,6-di(1H-imidazol-1-yl)-4-methylpyridine (0.8 g, 3.552 mmol, 1.0 equiv) and a stir-bar. The flask was filled with DMF (25 mL) from SPS. Then the flask was connected to a Schlenk line under N2 and sealed with a rubber septum. Methyl trifluoromethanesulfonate (1.61 mL, 14.208 mmol, 4.0 equiv) was added to the reaction mixture using a syringe through the septum. Then the reaction mixture was stirred at room temperature for 16 hours. After 16 hours, the reaction mixture was concentrated to about 10 mL and diluted with dichloromethane (25 mL) and diethyl ether (25 mL), which resulted in a suspension. The resulting suspension was stirred for 10 minutes then filtered over a fritted-funnel to obtain the product (9b) as white solid (1.67 g, 3.019 mmol) with an 85% yield. $^1$H-NMR (DMSO-d6, 360 MHz, ppm): δ 10.21 (s, 2H); 8.68 (apparently singlet, 2H); 8.10 (s, 2H); 8.05 (apparently singlet, 2H); 4.01 (s, 6H); 2.61 (s, 3H). {$^1$H}$^{13}$C-NMR (DMSO-d6, 126 MHz, ppm): δ 156.82; 145.18; 136.12; 125.01; 120.65 (q, J$_{CF}$=323 Hz); 119.03; 114.58; 36.56; 21.21. $^{19}$F-NMR (DMSO-d6, 339 MHz, ppm): δ −77.80.

Ru-[{Im(Me)-py(4-Me)-Im(Me)}(CH$_3$CN)$_2$Cl]triflate (9)

A Schlenk flask was loaded with [Ru(p-Cym)Cl$_2$]$_2$ (0.100 g, 0.163 mmol, 1.0 equiv.), 1,1'-(4-methylpyridine-2,6-diyl) bis(3-methyl-1H-imidazol-3-ium)triflate (0.176 g, 0.310 mmol, 1.90 equiv), triethylamine (0.23 mL, 1.630 mmol, 10.0 equiv.) and a stir-bar. The flask was filled with acetonitrile (10 mL), sealed with a rubber septum and connected to a Schlenk line under N$_2$. Then the reaction mixture was stirred while heating at 50° C. for one two days. After cooling to room temperature, reaction mixture was filtered. Filtrate was concentrated to obtain brownish yellow solid which was washed with acetonitrile (1 mL) and diethyl ether (5 mL) five times to obtain the product (9) as yellow solid (0.077 g, 0.124 mmol) with 40% yield. Single crystal was grown by slow vapor diffusion of diethyl ether into acetonitrile solution of the compound. $^1$H-NMR (DMSO-d6, 360 MHz, ppm): δ 8.38 (d, 2H, J$_{HH}$=1.5 Hz); 7.76 (s, 2H); 7.65 (d, 2H, J$_{HH}$=1.5 Hz); 4.10 (s, 6H); 2.73 (s, 3H); 2.63 (s, 3H); 2.10 (s, 3H). $^{19}$F-NMR (DMSO-d6, 339 MHz, ppm): δ −77.76. HRMS (ESI) calculated for RuC$_{18}$H$_{21}$N$_7$Cl (M-triflate): 472.0590, found 472.0595. Anal. calculated for RuC$_{21}$H$_{24}$N$_6$O$_3$F$_3$SCl (M+CH$_3$CN): C—38.10, H-3.65, N—16.93; found C—37.90, H—3.45, N—16.31. FT-IR (ATR, cm$^{-1}$): 3160.70, 3118.12, 2983.11, 2928.06, 2268.08, 1627.71, 1578.88, 1551.48, 1479.69, 1432.91, 1404.92, 1384.43, 1349.10, 1262.48, 1223.44, 1199.78, 1155.61, 1098.54, 1048.07, 1028.71, 990.17, 957.68, 945.93, 877.36, 855.22, 788.13, 749.45, 739.16, 698.52, 636.57, 590.26, 572.05, 563.48, 517.02, 430.77.

Synthesis of Complex 10

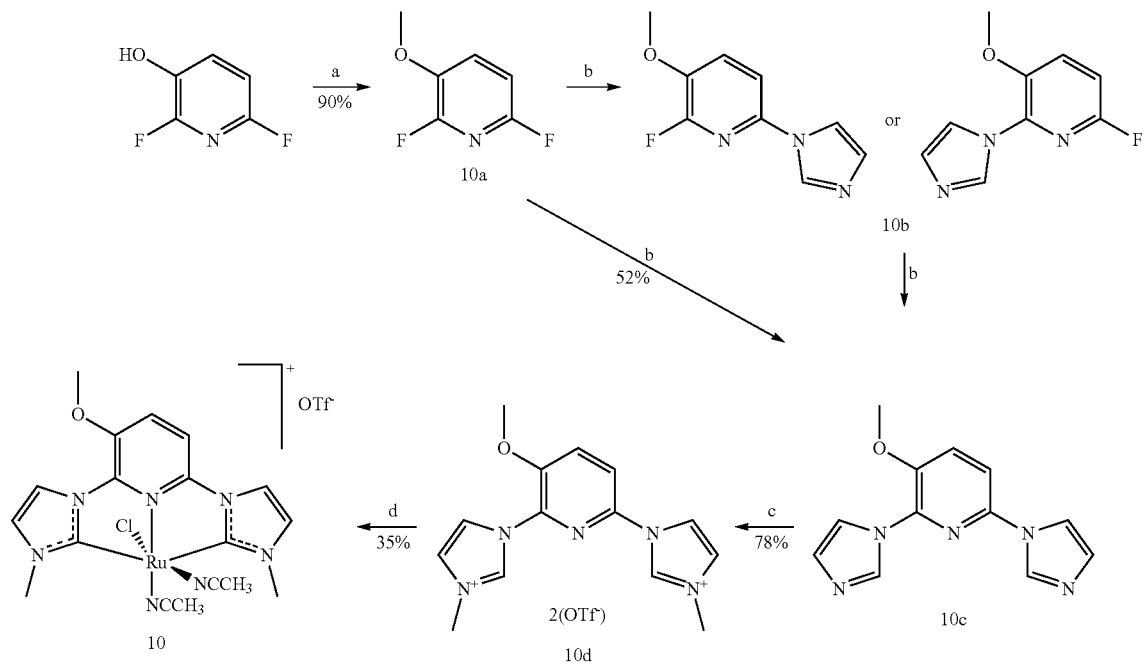

Scheme 10

*(a) K$_2$CO$_3$, MeI, acetone;
(b) 1H-imidazole, K$_2$CO$_3$, DMF;
(c) methyl trifluoromethanesulfonate, DMF; and
(d) [{Ru(p-Cym)Cl$_2$}$_2$], triethylamine, acetonitrile.

2,6-difluoro-3-methoxypyridine (10a)

A Schlenk flask was loaded with 2,6-difluoropyridin-3-ol (0.4 g, 3.052 mmol, 1.0 equiv.), $K_2CO_3$ (0.844 g, 6.104 mmol, 2.0 equiv.), acetone (10 mL) and a stir-bar. The flask was sealed with a rubber septum and connected to a Schlenk line under $N_2$. Iodomethane (0.38 mL, 6.104 mmol, 2.0 equiv.) was added using a syringe through the septum. Then the reaction mixture was heated at 55° C. while stirring for five hours. After cooling to room temperature, the mixture was filtered through a celite plug. Filtrate was evaporated to dryness, and the crude product was layered between water (10 mL) and ethyl acetate (20 mL) and separated. Aqueous part was further extracted with ethyl acetate (2×20 mL), combined ethyl acetate part was washed with brine, dried over anhydrous $MgSO_4$, filtered and concentrated to obtain the product (10a) as a colorless liquid (0.4 g, 2.747 mmol) with 90% yield. $^1$H-NMR (500 MHz, $CDCl_3$, ppm): δ 7.42 (m, 1H), 6.74 (m, 1H), 3.87 (s, 3H). $^{19}$F-NMR ($CDCl_3$, 339 MHz, ppm): δ −79.89; −84.03.

2,6-di(1H-imidazol-1-yl)-3-methoxypyridine (10c)

A Schlenk flask was loaded with 2,6-difluoro-3-methoxylpyridine (0.4 g, 2.757 mmol, 1.0 equiv.), 1H-imidazole (0.413 g, 6.065 mmol, 2.2 equiv), $K_2CO_3$ (1.524 g, 11.028 mmol, 4.0 equiv) and a stir-bar. The flask was filled with DMF (10 mL) from SPS. Then the flask was connected to a Schlenk line under N2 and sealed with a rubber septum. The reaction mixture was stirred while heating at 100° C. for two days. After cooling to room temperature, the reaction mixture was diluted with ice-cooled water (15 mL) and extracted with ethyl acetate (3×30 mL). Combined ethyl acetate part was washed with brine, dried over anhydrous $MgSO_4$, filtered and concentrated to get the crude product. Mixture of crude products was separated by column (silica gel) chromatography using 0-10% methanol in dichloromethane as eluent.

2-fluoro-6-(1H-imidazol-1-yl)-3-methoxypyridine or 6-fluoro-2-(1H-imidazol-1-yl)-3-methoxypyridine (10b) was isolated as white solid (major product) along with 2,6-di(1H-imidazol-1-yl)-3-methoxypyridine (10c). $^1$H-NMR of 2b ($CDCl_3$, 360 MHz, ppm): δ 8.48 (s, 1H), 7.82 (s, 1H), 7.51 (dd, 1H, $J_{HH,HF}$=8.6, 6.1 Hz), 7.15 (s, 1H), 6.85 (dd, 1H, $J_{HH,HF}$=8.6, 3.6 Hz); 3.97 (s, 3H). $^{19}$F-NMR ($CDCl_3$, 339 MHz, ppm): δ −77.97.

10b was further reacted with 1H-imidazole (2.0 equiv.) and $K_2CO_3$ (4.0 equiv.) at 100° C. for two more days. Finally, 2,6-di(1H-imidazol-1-yl)-3-methoxypyridine (10c) was obtained as white solid (0.346 g, 1.434 mmol) with 52% overall yield. $^1$H-NMR of 10c ($CDCl_3$, 360 MHz, ppm): δ 8.53 (s, 1H), 8.26 (s, 1H), 7.88 (m, 1H), 7.59 (m, 1H), 7.55 (d, 1H, $J_{HH}$=8.6 Hz); 7.28 (d, 1H, $J_{HH}$=8.6 Hz); 7.22 (m, 1H), 7.19 (m, 1H), 4.03 (s, 3H).

1,1'-(3-methoxypyridine-2,6-diyl)bis(3-methyl-1H-imidazol-3-ium)triflate (10d)

Synthesis is similar as that of 9b. 1,1'-(3-methoxypyridine-2,6-diyl)bis(3-methyl-1H-imidazol-3-ium)triflate (10d) was obtained as white solid (0.626 g, 1.099 mmol) with 78% yield. $^1$H-NMR (DMSO-$d_6$, 360 MHz, ppm): δ 10.12 (s, 1H), 10.03 (s, 1H), 8.66 (m, 1H), 8.64 (m, 1H), 8.32 (d, 1H, $J_{HH}$=9.4 Hz); 8.20 (d, 1H, $J_{HH}$=9.4 Hz); 8.05 (m, 1H), 8.01 (m, 1H), 4.13 (s, 3H); 4.03 (s, 3H); 3.99 (s, 3H). $^{19}$F-NMR (DMSO-d6, 339 MHz, ppm): δ −77.76.

Ru-[{Im(Me)-py(3-OMe)-Im(Me)}$(CH_3CN)_2$Cl] triflate (10)

Synthesis is similar as that of 9. Ru-[{Im(Me)-py(3-OMe)-Im(Me)}$(CH_3CN)_2$Cl]triflate (10) was obtained as yellow solid (0.069 g, 0.108 mmol) with 35% yield. $^1$H-NMR (DMSO-d6, 360 MHz, ppm): δ 8.38 (m, 2H); 7.83 (d, 1H, $J_{HH}$=9.4 Hz); 7.79 (d, 1H, $J_{HH}$=9.4 Hz); 7.61 (m, 2H); 4.11 (s, 3H); 4.09 (s, 3H); 4.08 (s, 3H); 2.74 (s, 3H); 2.11 (s, 3H). $^{19}$F-NMR (DMSO-d6, 339 MHz, ppm): δ−77.76. HRMS (ESI) calculated for $RuC_{18}H21N_7OCl$ (M-triflate): 488.0539, found 488.0541. Anal. calculated for $RuC_{19}H_{23}N_7O_5F_3SCl$ (M+$H_2O$): C—34.84, H—3.54, N—14.97; found C—34.80, H—3.52, N—14.84. FT-IR (ATR, cm$^{-1}$): 3515.89, 3091.49, 2931.62, 2773.66, 2084.79, 1621.33, 1584.59, 1561.09, 1497.01, 1469.49, 1401.52, 1350.81, 1255.62, 1239.30, 1222.72, 1147.42, 1096.00, 1028.01, 941.03, 831.91, 737.59, 697.74, 636.33, 572.13, 516.45, 442.65, 426.05, 413.14.

Synthesis of Complex 11 ($1^{NMe2}$)

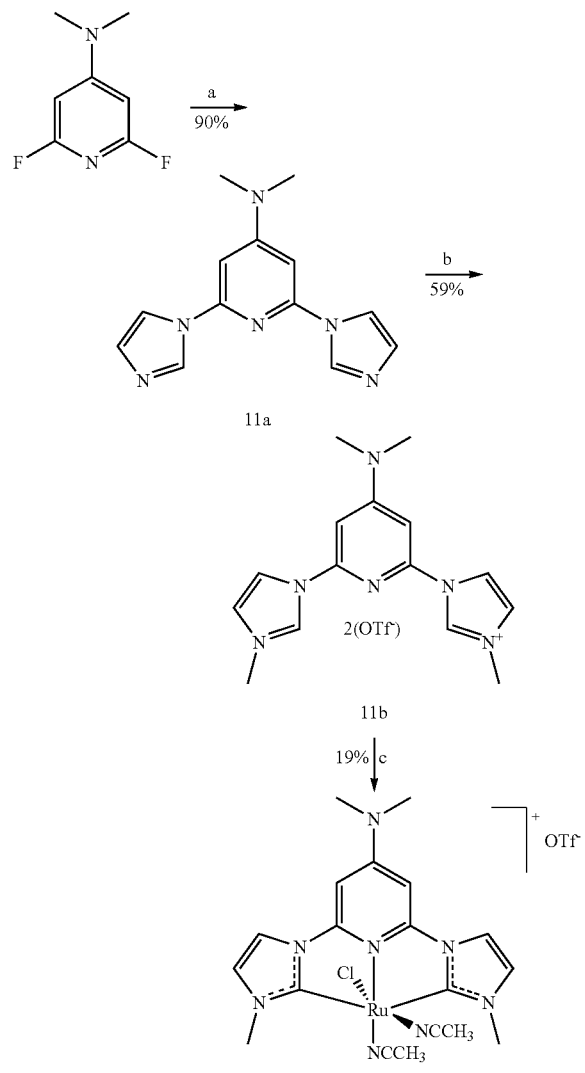

Scheme 11

11 (same as $1^{NMe2}$)

*(a) 1H-imidazole, 95% NaH, DMF; (b) methyl trifluoromethanesulfonate, DMF; and (c) [{Ru(p-Cym)$Cl_2$}$_2$], $Cs_2CO_3$, acetonitrile.

2,6-difluoro-N,N-dimethylpyridin-4-amine (11a)

Inside the glovebox, a Schlenk flask was loaded with 95% NaH (0.168 g, 6.640 mmol, 2.1 equiv.), DMF (15 mL) and a stir-bar and the resulting suspension were stirred for ten minutes. 1H-imidazole (0.452 g, 6.640 mmol, 2.1 equiv) was added to the above suspension portion-wise, and the resulting mixture was stirred for five minutes. 2,6-difluoro-N,N-dimethylpyridin-4-amine (0.5 g, 3.162 mmol, 1.0 equiv.) was added to the reaction mixture, the flask was sealed with a rubber septum, taken out of the box, connected to a Schlenk line under $N_2$, and the reaction mixture was stirred at 70° C. for 23 hours. After cooling to room temperature, the reaction mixture was diluted with ice-cooled water (20 mL) and extracted with ethyl acetate (3×50 mL). Combined organic part was washed with brine, dried over anhydrous $MgSO_4$, filtered, and the filtrate was concentrated to get the crude product. Recrystallization of the crude product from methanol gave the product (11a) as white solid (0.724 g, 2.846 mmol) with a 90% yield. $^1$H-NMR (500 MHz, $CDCl_3$, ppm): δ 8.32 (m, 2H); 7.61 (m, 2H); 7.19 (m, 2H); 6.40 (s, 2H); 3.16 (s, 6H).

1,1'-(4-(dimethylamino)pyridine-2,6-diyl)bis(3-methyl-1H-imidazol-3-ium)triflate (11b)

Synthesis is similar as that of 9b. 1,1'-(4-(dimethylamino)pyridine-2,6-diyl)bis(3-methyl-1H-imidazol-3-ium)triflate (11 b) was obtained as white solid (0.676 g, 1.160 mmol) with 59% yield. $^1$H-NMR (DMSO-d6, 360 MHz, ppm): δ 10.15 (s, 2H); 8.71 (s, 2H); 8.01 (s, 2H); 7.25 (s, 2H); 3.99 (s, 6H); 3.21 (s, 6H).

Ru-[{Im(Me)-py(4-NMe$_2$)-Im(Me)}(CH$_3$CN)$_2$Cl] triflate (11) (same as $1^{NMe2}$)

A Schlenk flask was loaded with [Ru(p-Cym)Cl$_2$]$_2$ (0.141 g, 0.230 mmol, 1.0 equiv.), 1,1'-(4-(dimethylamino)pyridine-2,6-diyl)bis(3-methyl-1H-imidazol-3-ium)triflate (0.308 g, 0.529 mmol, 2.3 equiv.), Cs$_2$CO$_3$ (0.517 g, 1.587 mmol, 6.9 equiv.) and a stir-bar. The flask was filled with acetonitrile (10 mL) from SPS, connected to a Schlenk line under $N_2$ and sealed with a rubber septum. Then the reaction mixture was stirred while heating at 70° C. for four hours, followed by stirring at room temperature for 16 hours. Reaction mixture was filtered through an alumina plug and the alumina plug was washed with acetonitrile until the filtrate ran colorless. Filtrate was concentrated to obtain brownish yellow solid which was washed with acetonitrile (2 mL) and diethyl ether (5 mL) three times to obtain the product (11 (same as $1^{NMe2}$)) (0.056 g, 0.086 mmol) as yellow solid with 19% yield. Single crystal was grown by slow vapor diffusion of diethyl ether into acetonitrile solution of the compound. $^1$H-NMR (CD$_3$CN, 500 MHz, rt): δ 7.95 (d, 2H, $J_{HH}$=2.0 Hz); 7.28 (d, 2H, $J_{HH}$=2.0 Hz); 6.74 (s, 2H); 4.12 (s, 6H); 3.19 (s, 6H); 2.54 (s, 3H); 1.90 (s, 3H). HRMS (ESI) calculated for RuC$_{19}$H$_{24}$N$_8$Cl (M-triflate): 501.0856, found 501.0858. Anal. calculated for RuC$_{20}$H$_{24}$N$_8$O$_3$F$_3$SCl (M): C—36.95, H—3.72, N—17.24; found C—37.14, H—3.53, N—17.26. FT-IR (ATR, cm$^{-1}$): 3456.50, 3156.55, 3090.05, 2928.97, 2821.16, 2259.70, 1631.82, 1570.07, 1537.20, 1502.62, 1488.09, 1464.05, 1429.71, 1401.19, 1348.38, 1335.36, 1259.72, 1222.02, 1180.06, 1146.08, 1100.19, 1084.69, 1030.56, 990.29, 958.18, 936.74, 813.63, 789.81, 750.14, 695.10, 635.82, 598.89, 570.61, 516.06, 492.85, 463.07, 446.22, 430.81.

Synthesis of Complex 12

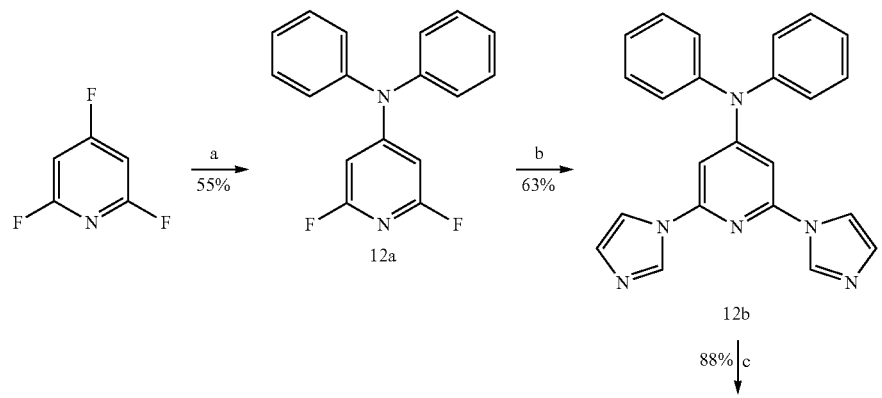

Scheme 12

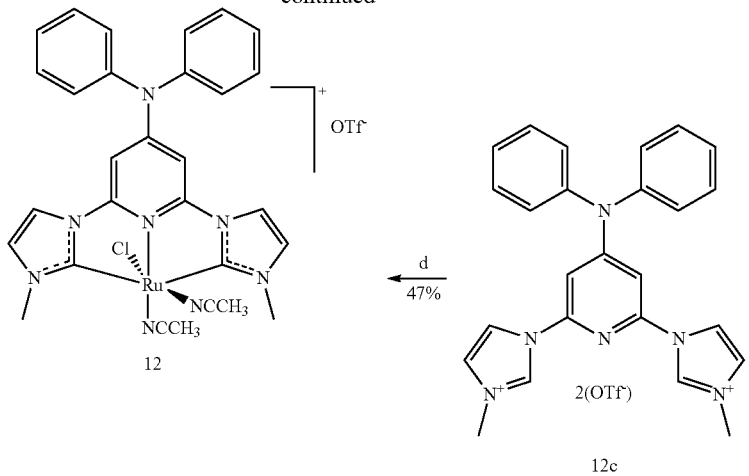

*(a) Diphenylamine, 1.6M n-butyllithium solution in hexane, 2,4,6-trifluoropyridine, THF;
(b) 1H-imidazole; K$_2$CO$_3$, DMF;
(c) methyl trifluoromethanesulfonate, DMF; and
(d) [{Ru(p-Cym)Cl$_2$}$_2$], triethylamine, acetonitrile.

2,6-difluoro-N,N-diphenylpyridin-4-amine (12a)

A Schlenk flask was loaded with diphenylamine (1.41 mL, 10.0 mmol, 1.0 equiv.) and a stir-bar. The flask was filled with THF (30 mL) from SPS. Then the flask was connected to a Schlenk line under N$_2$, sealed with a rubber septum and cooled in an ice-water bath. 1.6M n-butyllithium solution in hexane (6.25 mL, 10.0 mmol, 1.0 equiv.) was added dropwise to the flask using a syringe through the septum. The resulting mixture was stirred at room temperature for one hour. Another Schlenk flask was loaded with 2,4,6-trifluoropyridine (10.0 mL, 113.0 mmol, 11.3 equiv.) and a stir-bar and filled with THF (70 mL) from SPS. Then the flask was connected to a Schlenk line under N$_2$, sealed with a rubber septum and cooled in an ice-water bath. The resulting solution from the first flask was cannula transferred to the second flask, and the reaction mixture was stirred at room temperature for six hours. Brine solution (50 mL) was added to the reaction mixture, dichloromethane (3×50 mL) was used to extract the aqueous phase. Combined organic part was dried over anhydrous MgSO$_4$, filtered, and the filtrate was concentrated to get the crude product. Recrystallization of the crude product from methanol gave the product (12a) as white solid (1.56 g, 5.526 mmol) with a 55% yield. $^1$H-NMR (500 MHz, CDCl$_3$, ppm): δ 7.42-7.39 (m, 4H); 7.29-7.22 (m, 6H); 6.08 (s, 2H). {$^1$H}$^{13}$C-NMR (CDCl$_3$, 126 MHz, ppm): δ 163.17 (dd, J$_{CF,CF}$=21, 240 Hz); 160.94 (t, J$_{CF}$=12 Hz); 144.33; 130.26; 127.25; 127.00; 92.69. $^{19}$F-NMR (CDCl$_3$, 339 MHz, ppm): δ −70.18.

This reaction was done with extreme precaution under a completely inert atmosphere.

2,6-di(1H-imidazol-1-yl)-N,N-diphenylpyridin-4-amine (12b)

Synthesis is similar as that of 9a. 2,6-di(1H-imidazol-1-yl)-N,N-diphenylpyridin-4-amine (12b) was obtained as white solid (0.304 g, 0.803 mmol) with 63% yield. $^1$H-NMR (CDCl$_3$, 360 MHz, ppm): δ 8.18 (s, 2H); 7.47-7.44 (m, 6H); 7.34-7.28 (m, 4H); 7.25 (s, 2H); 7.13 (s, 2H); 6.59 (s, 2H). {$^1$H}$^{13}$C-NMR (CDCl$_3$, 126 MHz, ppm): δ 158.47; 149.35; 144.26; 135.15; 130.71; 130.38; 127.10; 127.08; 116.30; 97.76.

1,1'-(4-(diphenylamino)pyridine-2,6-diyl)bis(3-methyl-1H-imidazol-3-ium)triflate (12c)

Synthesis is similar as that of 9b. 1,1'-(4-(diphenylamino)pyridine-2,6-diyl)bis(3-methyl-1H-imidazol-3-ium)triflate (12c) was obtained as white solid (0.410 g, 0.581 mmol) with 88% yield. $^1$H-NMR (DMSO-d6, 360 MHz, ppm): δ 10.00 (s, 2H); 8.56 (m, 2H); 7.95 (m, 2H); 7.55-7.51 (m, 4H); 7.42-7.36 (m, 6H); 7.12 (s, 2H); 3.93 (s, 6H). {$^1$H}$^{13}$C-NMR (DMSO-d6, 126 MHz, ppm): δ 158.90; 146.32; 143.54; 136.04; 130.57; 127.43; 126.95; 124.57; 120.66 (q, J$_{CF}$=323 Hz); 119.32; 100.34; 36.38. $^{19}$F-NMR (DMSO-d6, 339 MHz, ppm): δ −77.76.

Ru-[{Im(Me)-py(4-NPh$_2$)-Im(Me)}(CH$_3$CN)$_2$Cl]triflate (12)

Synthesis is similar as that of 9. Ru-[{Im(Me)-py(4-NPh$_2$)-Im(Me)}(CH$_3$CN)$_2$Cl]triflate (12) was obtained as yellow solid (0.057 g, 0.073 mmol) with 47% yield. $^1$H-NMR (DMSO-d6, 360 MHz, ppm): δ 8.26 (d, 2H, J$_{HH}$=2.2 Hz); 7.53 (d, 2H, J$_{HH}$=2.2 Hz); 7.52-7.47 (m, 4H); 7.36-7.31 (m, 6H); 7.00 (s, 2H); 4.07 (s, 6H); 2.70 (s, 3H); 2.14 (s, 3H). $^{19}$F-NMR (DMSO-d6, 339 MHz, ppm): δ −77.76. HRMS (ESI) calculated for RuC$_{29}$H$_{28}$N$_8$Cl (M-triflate): 625.1169, found 625.1174. Anal. calculated for RuC$_{30}$H$_{30}$N$_8$O$_4$F$_3$SCl (M+H$_2$O): C—45.48, H—3.82, N—14.14; found C—46.07, H—3.76, N—14.36. FT-IR (ATR, cm$^{-1}$): 3850.66, 3156.03, 3071.03, 2977.32, 2284.93, 2273.62, 2168.24, 2088.57, 2047.02, 1977.58, 1639.21, 1597.93, 1564.24, 1536.35, 1482.12, 1440.69, 1400.78, 1347.15, 1321.68, 1306.10, 1257.21, 1224.57, 1149.62, 1087.49, 1077.18, 1062.64, 1030.55, 996.23, 963.15, 943.58, 916.61, 849.71, 803.85, 788.07, 771.32, 752.66, 732.24, 721.02, 709.30, 693.29, 639.29, 593.69, 571.89, 553.16, 516.85, 500.14, 466.44, 444.15, 429.38, 408.51.

Synthesis of complex 13 (1$^{OH}$)

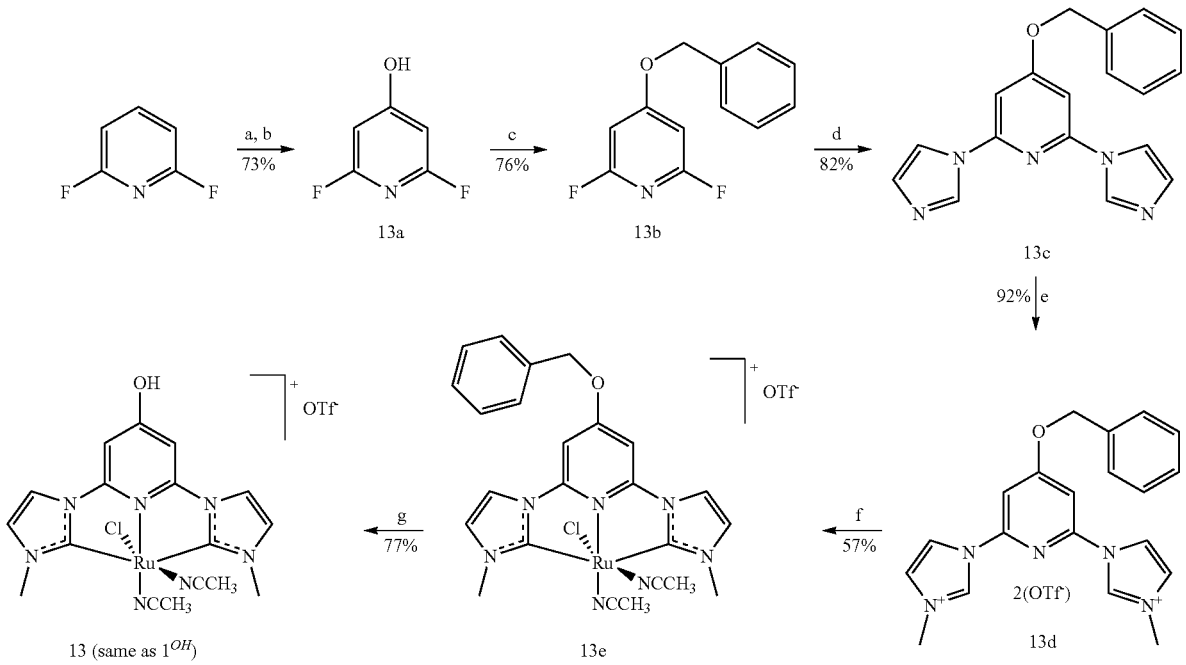

Scheme 13

*(a) [{Ir(COD)Cl}$_2$], pinacolborane, DPPE, THF; (b) K-Oxone, H$_2$O; (c) benzylchloride, K$_2$CO$_3$, tetra-n-butylammoniumiodide (TBAI), DMF; (d) 1H-imidazole, K$_2$CO$_3$, DMF; (e) methyl trifluoromethanesulfonate, DMF; (f) [{Ru(p-Cym)Cl$_2$}$_2$], triethylamine, acetonitrile; and (g) 10% Pd—C, acetonitrile.

2,6-difluoropyridin-4-ol (13a) (Maleczka, R. E.; et al., *Journal of the American Chemical Society* 2003, 125 (26), 7792-7793).

A Schlenk flask was loaded with 2,6-difluoropyridine (0.79 mL, 8.690 mmol, 1.0 equiv.), pinacolborane (2.52 mL, 17.380 mmol, 2.0 equiv.), [Ir(COD)Cl]$_2$ (0.058 g, 1 mol %), DPPE (0.069 g, 2 mol %), dry THF (25 mL) and a stir-bar inside a glove-box. The flask was sealed with a rubber septum and taken out of the glove-box. Then the flask was connected to a Schlenk line under N$_2$, and the reaction mixture was heated at 80° C. while stirring for 16 hours. After cooling to room temperature, an aqueous solution (50 mL) of K-Oxone (5.88 g, 19.118 mmol, 2.2 equiv.) was added slowly, stirring continued for 10 minutes. Then saturated aqueous solution (50 mL) of NaHSO$_3$ was added to quench the excess K-oxone. The resulting mixture was extracted with ethyl acetate (3×50 mL), combined ethyl acetate part was washed with brine, dried over anhydrous MgSO$_4$, filtered and evaporated to get the crude product. Crude was purified by column chromatography (silica gel) using 0-30% ethyl acetate in hexane as eluent to obtain the product (13a) as white solid (0.83 g, 6.344 mmol) with 73% yield. $^1$H-NMR (DMSO-d6, 500 MHz, ppm): δ 11.90 (s, 1H); 6.40 (s, 2H). {$^1$H}$^{13}$C-NMR (DMSO-d$_6$, 126 MHz, ppm): δ 171.66 (t, J$_{CF}$=12.9 Hz), 162.18 (dd, J$_{CF,CF}$=238, 22 Hz); 93.49 (m). $^{19}$F-NMR (DMSO-d6, 339 MHz, ppm): δ −70.66.

2,6-difluoropyridin-3-ol was formed as a minor product.

4-(benzyloxy)-2,6-difluoropyridine (13b)

A Schlenk flask was loaded with 2,6-difluoropyridin-4-ol (0.7 g, 5.340 mmol, 1.0 equiv.), K$_2$CO$_3$ (1.48 g, 10.680 mmol, 2.0 equiv.), TBAI (0.04 g, 2 mol %) and a stir-bar. The flask was filled with DMF (15 mL) from SPS. Then the flask was connected to a Schlenk line under N$_2$ and sealed with a rubber septum. Benzylchloride (1.23 mL, 10.680 mmol, 2.0 equiv.) was added to the flask dropwise using a syringe through the septum. Then the reaction mixture was stirred at room temperature for 16 hours. After 16 hours, cold water (20 mL) was added to the reaction mixture and was extracted with ethyl acetate (3×50 mL), combined ethyl acetate part was washed with brine, dried over anhydrous MgSO$_4$, filtered and evaporated to get the crude product. Finally, the crude was purified by column (silica gel) chromatography using 0-12% ethyl acetate in hexane to obtain the product (13b) as white solid (1.03 g, 4.638 mmol) with 76% yield. $^1$H-NMR (CDCl$_3$, 500 MHz, ppm): δ 7.44-7.37 (m, 5H); 6.37 (s, 2H); 5.13 (s, 2H). {$^1$H}$^{13}$C-NMR (CDCl$_3$, 126 MHz, ppm): δ 171.62 (t, 11.8 Hz), 162.98 (dd, J$_{CF, CF}$=246, 20.2 Hz), 134.69; 129.06; 128.97; 127.72; 93.07 (m); 71.41. $^{19}$F-NMR (CDCl$_3$, 339 MHz, ppm): δ −67.88.

4-(benzyloxy)-2,6-di(1H-imidazol-1-yl)pyridine (13c)

Synthesis is similar as that of 9a. 4-(benzyloxy)-2,6-di (1H-imidazol-1-yl)pyridine (5c) was obtained as white solid (1.06 g, 3.336 mmol) with 82% yield. $^1$H-NMR (CDCl$_3$, 500 MHz, ppm): δ 8.30 (m, 2H); 7.58 (m, 2H); 7.44-7.38 (m, 5H); 7.19 (m, 2H); 6.82 (s, 2H); 5.24 (s, 2H). {$^1$H}$^{13}$C-NMR (CDCl$_3$, 126 MHz, ppm): 169.24; 149.75; 135.16; 134.65; 131.05; 129.12; 129.04; 127.67; 116.28; 97.01; 71.24.

1,1'-(4-(benzyloxy)pyridine-2,6-diyl)bis(3-methyl-1H-imidazol-3-ium)triflate (13d)

Synthesis is similar as that of 9b. 1,1'-(4-(benzyloxy) pyridine-2,6-diyl)bis(3-methyl-1H-imidazol-3-ium)triflate (13d) was obtained as white solid (1.12 g, 0.174 mmol) with 92% yield. $^1$H-NMR (DMSO-d6, 500 MHz, ppm): δ 10.21 (s, 2H); 8.72 (m, 2H); 8.04 (m, 2H); 7.95 (s, 2H); 7.57-7.42 (m, 5H); 5.46 (s, 2H); 4.02 (s, 6H). {$^1$H}$^{13}$C-NMR (DMSO-d6, 126 MHz, ppm): δ 170.16; 146.67; 136.19; 134.73; 128.79; 128.74; 128.39; 125.01; 120.66 (q, $J_{CF}$=323 Hz); 119.08; 101.02; 71.71; 36.61. $^{19}$F-NMR (DMSO-d6, 339 MHz, ppm): δ −77.76.

Ru-[{Im(Me)-py(4-OCH$_2$Ph)-Im(Me)}(CH$_3$CN)$_2$Cl] triflate (13e)

Synthesis is similar as that of 9. Ru-[{Im(Me)-OCH$_2$Ph)-Im(Me)}(CH$_3$CN)$_2$Cl]triflate (13e) was obtained as greenish-yellow solid (0.126 g, 0.177 mmol) with 57% yield. $^1$H-NMR (DMSO-d6, 360 MHz, ppm): δ 8.41 (d, $J_{HH}$=2.2 Hz, 2H); 7.72 (s, 2H); 7.64 (d, $J_{HH}$=2.2 Hz, 2H); 7.58-7.42 (m, 5H); 5.38 (s, 2H); 4.11 (s, 6H); 2.72 (s, 3H); 2.11 (s, 3H). $^{19}$F-NMR (DMSO-d6, 339 MHz, ppm): δ 77.75. Anal. calculated for RuC$_{25}$H$_{25}$N$_7$O$_4$F$_3$SCl: C—42.11, H—3.53, N—13.75, found C—41.62, H—3.52, N—13.58. FT-IR (ATR, cm$^{-1}$): 3493.80, 3082.72, 3044.90, 2928.50, 2269.95, 2110.27, 1629.93, 1578.90, 1551.58, 1483.39, 1402.87, 1386.57, 1348.91, 1257.11, 1238.18, 1219.78, 1208.13, 1148.22, 1101.20, 1084.67, 1065.60, 1029.86, 965.55, 916.46, 894.45, 842.70, 788.57, 743.97, 733.72, 698.76, 655.66, 635.39, 597.34, 571.07, 516.04, 444.46, 429.56.

Ru-[{Im(Me)-py(4-OH)-Im(Me)}(CH$_3$CN)$_2$Cl]triflate (13 (the same as 1$^{OH}$))

Ru-[{Im(Me)-py(4-OCH$_2$Ph)-Im(Me)}(CH$_3$CN)$_2$Cl]triflate (0.120 g, 0.168 mmol, 1.0 equiv.) was dissolved in acetonitrile (20 mL) in a two necked round bottomed flask containing a stir bar. The flask was sealed with a vacuum adapter and a rubber septum. Then the solution was purged with N2 gas for 10 minutes while stirring, and 10% Pd—C (0.020 g) was added to the flask. The head-space of the flask was evacuated and filled back with H$_2$ gas using an H$_2$ filled balloon, and this process was repeated three times. The resulting mixture was stirred at room temperature under H$_2$ gas for 10 hours. After 10 hours, the reaction mixture was filtered through a celite plug to remove Pd—C, more acetonitrile (20 mL) was used to wash the celite plug. The filtrate was concentrated to get a greenish-yellow solid, which was washed with acetonitrile (1 mL) and diethyl ether (5 mL) three times to obtain the product (13 (1$^{OH}$)) as a greenish-yellow solid (0.08 g, 0.129 mmol) with 77% yield. Single crystal was grown by slow vapor diffusion of diethyl ether into acetonitrile solution of the compound. $^1$H-NMR (DMSO-d6, 500 MHz, ppm): δ 8.31 (s, 2H); 7.60 (s, 2H); 7.18 (s, 2H); 4.09 (s, 6H); 2.70 (s, 3H); 2.11 (s, 3H). $^{19}$F-NMR (DMSO-d$_6$, 339 MHz, ppm): δ −77.75. HRMS (ESI) calculated for RuC$_{17}$H$_{19}$ON$_7$Cl (M-triflate): 474.0383, found 473.0372. Anal. calculated for RuC$_{18}$H$_{21}$N$_7$O$_5$F$_3$SCl: C—33.73, H—3.30, N—15.30; found C—34.85, H—3.39, N—15.69. FT-IR (ATR, cm$^{-1}$): 3097.64, 2980.71, 2274.48, 1632.75, 1590.71, 1566.04, 1500.01, 1478.34, 1404.49, 1347.56, 1254.77, 1239.76, 1221.74, 1207.92, 1156.49, 1098.84, 1026.84, 948.70, 898.73, 850.01, 819.26, 791.94, 743.38, 697.36, 635.44, 599.59, 571.43, 516.36, 443.05, 422.36.

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

The claims are not intended to include, and should not be interpreted to include, means-plus- or step-plus-function limitations, unless such a limitation is explicitly recited in a given claim using the phrase(s) "means for" or "step for," respectively.

In view of the described processes and compositions, hereinbelow are described certain more particularly described aspects of the inventions. These particularly recited aspects should not, however, be interpreted to have any limiting effect on any different claims containing different or more general teachings described herein, or that the "particular" aspects are somehow limited in some way other than the inherent meanings of the language and formulas literally used therein.

ASPECTS

Aspect 1: A method comprising: selectively deoxygenating at least one oxygenated aromatic compound in the presence of a hydrogen gas and a catalyst system to form a reaction product, wherein the catalyst system comprises a catalyst of formula (I):

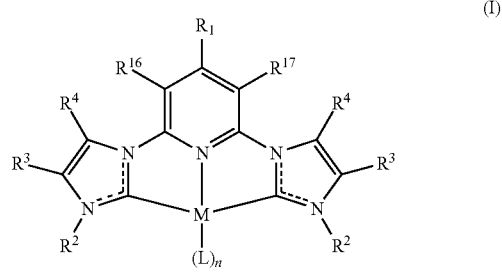

wherein,
R$^1$ is hydrogen, OH, O$^-$, halogen, amine, C$_1$-C$_{10}$ alkyl, C$_1$-C$_{10}$ alkoxy, C$_2$-C$_{10}$ alkenyl, C$_2$-C$_{10}$ alkynyl, C$_6$-C$_{14}$ aryl, C$_1$-C$_{13}$ heteroaryl, C$_6$-C$_{14}$ aryloxy, C$_3$-C$_{10}$ cycloalkyl, or C$_3$-C$_{10}$ cycloalkenyl, wherein R$^1$ is optionally substituted with C$_1$-C$_{10}$ alkyl, C$_1$-C$_{10}$ alkoxy, C$_2$-C$_{10}$ alkenyl, C$_2$-C$_{10}$ alkynyl, C$_6$-C$_{14}$ aryl, C$_1$-C$_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl;

each R$^2$ is, independent of the other, C$_1$-C$_{10}$ alkyl, C$_2$-C$_{10}$ alkenyl, C$_2$-C$_{10}$ alkynyl, C$_6$-C$_{14}$ aryl, or C$_1$-C$_{13}$ heteroaryl, wherein R$^2$ is optionally substituted with C$_1$-C$_{10}$ alkyl, C$_1$-C$_{10}$ alkoxy, C$_2$-C$_{10}$ alkenyl, C$_2$-C$_{10}$ alkynyl, C$_6$-C$_{14}$ aryl, C$_1$-C$_{13}$ heteroaryl, aldehyde, amino, carboxylic acid, ester, ether, halide, hydroxy, ketone, nitro, cyano, silyl, sulfo-oxo, sulfonyl, sulfone, sulfoxide, or thiol, each R$^3$ and R$^4$ are, independent of the other, hydrogen, C$_1$-C$_{10}$ alkyl, C$_2$-C$_{10}$ alkenyl, C$_2$-C$_{10}$ alkynyl, C$_6$-C$_{14}$ aryl, or C$_1$-C$_{13}$ heteroaryl, wherein R$^3$ and R$^4$ are optionally substituted with C$_1$-C$_{10}$ alkyl, C$_1$-C$_{10}$ alkoxy, C$_2$-C$_{10}$ alkenyl, C$_2$-C$_{10}$ alkynyl, C$_6$-C$_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, or thiol, or $R^3$ and $R^4$ combine together with the atoms to which they are attached to form a cycloalkyl, cycloheteroaryl, aryl, or heteroaryl;

each $R^{16}$ and $R^{17}$ are, independent of the other, hydrogen, OH, O$^-$, halogen, amine, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, $C_6$-$C_{14}$ aryloxy, $C_3$-$C_{10}$ cycloalkyl, or $C_3$-$C_{10}$ cycloalkenyl, wherein each $R^{16}$ and $R_{15}$, independent of the other, is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl;

M is Ru or Ir;

each L is independently selected from Cl, Br, $CH_3CN$, DMF, $H_2O$, bipyridine, phenylpyridine, $CO_2$, and a CNC-pincer ligand; and n is 1, 2, or 3.

Aspect 2: The method of Aspect 1, wherein the oxygenated aromatic compound has a formula (II)

(II)

wherein $R^5$ is independently selected from hydrogen, substituted or unsubstituted $C_6$-alkyl, $R^{11}$—OH; —$OR^{12}$, $R^{18}OR^{19}$, $R^{20}COR^{21}$ substituted or unsubstituted $C_3$-$C_{10}$ cycloalkyls and heteroalkyls, $C_2$-$C_{10}$ alkenyl, and Ar';

$R^6$ is independently selected from hydrogen, hydrogen, substituted or unsubstituted $R^{11}$—OH; —$OR^{12}$, $R^{18}OR^{19}$, $R^{20}COR^{21}$, substituted or unsubstituted $C_3$-$C_{10}$ cycloalkyls and heteroalkyls, $C_2$-$C_{10}$ alkenyl, and Ar';

$R^7$ is independently selected from hydrogen, substituted or unsubstituted $C_6$-alkyl, $R^{11}$—OH, —$OR^{12}$, $R^{18}OR^{19}$, $R^{20}COR^{21}$, substituted or unsubstituted $C_3$-$C_{10}$ cycloalkyls and heteroalkyls, $C_2$-$C_{10}$ alkenyl, and Ar';

$R^8$ is independently selected from hydrogen, substituted or unsubstituted $C_6$-alkyl, $R^{11}$—O$_H$; —$OR^{12}$, $R^{18}OR^{19}$, $R^{20}COR^{21}$, substituted or unsubstituted $C_3$-$C_{10}$ cycloalkyls and heteroalkyls, $C_2$-$C_{10}$ alkenyl, and Ar';

$R^9$ is independently selected from hydrogen, substituted or unsubstituted $C_6$-alkyl, $R^{11}$—OH; —$OR^{12}$, $R^{18}OR^{19}$, $R^{20}COR^{21}$, substituted or unsubstituted $C_3$-$C_{10}$ cycloalkyls and heteroalkyls, $C_2$-$C_{10}$ alkenyl, and Ar';

$R^{10}$ is independently selected from hydrogen, substituted or unsubstituted $C_6$-alkyl, $R^{11}$—OH; —$OR^{12}$, $R^{18}OR^{19}$, $R^{20}COR^{21}$, substituted or unsubstituted $C_3$-$C_{10}$ cycloalkyls and heteroalkyls, $C_2$-$C_{10}$ alkenyl, and Ar';

wherein when $R^6$, $R^7$, $R^9$, and $R^{10}$ are all hydrogen, $R^5$ is $R^{11}$—OH, $R^{18}OR^{19}$, or $R^{20}COR^{21}$, wherein $R^{11}$ is a bond, substituted or unsubstituted $C_1$-$C_6$ alkyl, $C_2$-$C_{10}$ alkenyl, or Ar'';

$R^{12}$ is independently selected from hydrogen, substituted or unsubstituted $C_1$-$C_6$ alkyl, $C_2$-$C_{10}$ alkenyl, and Ar''', $R^{18}$ is independently selected from substituted or unsubstituted $C_1$-$C_6$-alkyl, substituted or unsubstituted $C_3$-$C_{10}$ cycloalkyls and heteroalkyls, $C_2$-$C_{10}$ alkenyl, and Ar';

$R^{19}$ is independently selected from substituted or unsubstituted $C_1$-$C_6$-alkyl, substituted or unsubstituted $C_3$-$C_{10}$ cycloalkyls and heteroalkyls, $C_2$-$C_{10}$ alkenyl, and Ar';

$R^{20}$ is independently selected from a bond, substituted or unsubstituted $C_1$-$C_6$-alkyl, substituted or unsubstituted $C_3$-$C_{10}$ cycloalkyls and heteroalkyls, $C_2$-$C_{10}$ alkenyl, and Ar';

$R^{21}$ is independently selected from hydrogen, hydroxyl, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, $C_6$-$C_{14}$ aryloxy, $C_3$-$C_{10}$ cycloalkyl, or $C_3$-$C_{10}$ cycloalkenyl and Ar', wherein $R^{21}$ is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl;

Ar' is a $C_6$-$C_{14}$ aryl or heteroaryl group optionally substituted with 1, 2, or 3 optional substituents; and Ar'' is a $C_6$-$C_{14}$ aryl or heteroaryl group optionally substituted with 1, 2, or 3 optional substituents;

Ar''' is a $C_6$-$C_{14}$ aryl or heteroaryl group optionally substituted with 1, 2, or 3 optional substituents;

wherein Ar', Ar'', or Ar''', are the same or different.

Aspect 3: The method of Aspect 2, wherein $R^5$ is $R^{11}$—OH, $R^{18}OR^{19}$, or $R^{20}COR^{21}$, $R^6$ is independently selected from hydrogen, substituted or unsubstituted $R^{11}$—OH; —$OR^{12}$, substituted or unsubstituted $C_3$-$C_{10}$ cycloalkyls and heteroalkyls, $C_2$-$C_{10}$ alkenyl, and Ar'; $R^7$ is independently selected from hydrogen, substituted or unsubstituted $R^{11}$—OH; —$OR^{12}$, substituted or unsubstituted $C_3$-$C_{10}$ cycloalkyls and heteroalkyls, $C_2$-$C_{10}$ alkenyl, and Ar'; $R^8$ is independently selected from hydrogen, substituted or unsubstituted $R^{11}$—OH; —$OR^{12}$, substituted or unsubstituted $C_3$-$C_{10}$ cycloalkyls and heteroalkyls, $C_2$-$C_{10}$ alkenyl, and Ar'; wherein $R^9$ is independently selected from hydrogen, substituted or unsubstituted $R^{11}$—OH; —$OR^{12}$, substituted or unsubstituted $C_3$-$C_{10}$ cycloalkyls and heteroalkyls, $C_2$-$C_{10}$ alkenyl, and Ar'; $R^{10}$ is independently selected from hydrogen, substituted or unsubstituted $C_1$-$C_6$-alkyl, $R^{11}$—OH; —$OR^{12}$, substituted or unsubstituted $C_3$-$C_{10}$ cycloalkyls and heteroalkyls, $C_2$-$C_{10}$ alkenyl, and Ar'; $R^{11}$ is a bond, substituted or unsubstituted $C_1$-$C_6$ alkyl, $C_2$-$C_{10}$ alkenyl, or Ar''; $R^{12}$ is independently selected from hydrogen, substituted or unsubstituted $C_1$-$C_6$ alkyl, $C_2$-$C_{10}$ alkenyl, and Ar''', $R^{18}$ is independently selected from substituted or unsubstituted $C_1$-$C_6$-alkyl, substituted or unsubstituted $C_3$-$C_{10}$ cycloalkyls and heteroalkyls, $C_2$-$C_{10}$ alkenyl, and Ar'; $R^{19}$ is independently selected from substituted or unsubstituted $C_1$-$C_6$-alkyl, substituted or unsubstituted $C_3$-$C_{10}$ cycloalkyls and heteroalkyls, $C_2$-$C_{10}$ alkenyl, and Ar'; $R^{20}$ is independently selected from a bond, substituted or unsubstituted $C_3$-$C_{10}$ cycloalkyls and heteroalkyls, $C_2$-$C_{10}$ alkenyl, and Ar'; $R^{21}$ is independently selected from hydrogen, hydroxyl, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, $C_6$-$C_{14}$ aryloxy, $C_3$-$C_{10}$ cycloalkyl, or $C_3$-$C_{10}$ cycloalkenyl and Ar', wherein $R^{21}$ is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl; Ar' is a $C_6$-$C_{14}$ aryl or heteroaryl group optionally substituted with 1, 2, or 3 optional substituents; Ar" is a $C_6$-$C_{14}$ aryl or heteroaryl group optionally substituted with 1, 2, or 3 optional substituents; Ar'" is a $C_6$-$C_{14}$ aryl or heteroaryl group optionally substituted with 1, 2, or 3 optional substituents; and wherein Ar', Ar", and Ar'" are the same or different.

Aspect 4: The method of Aspect 2 or 3, wherein the aromatic compound of formula (II) comprises at least two hydroxyl groups.

Aspect 5: The method of any one of Aspects 3-4, wherein the aromatic compound of formula (II) is selected from

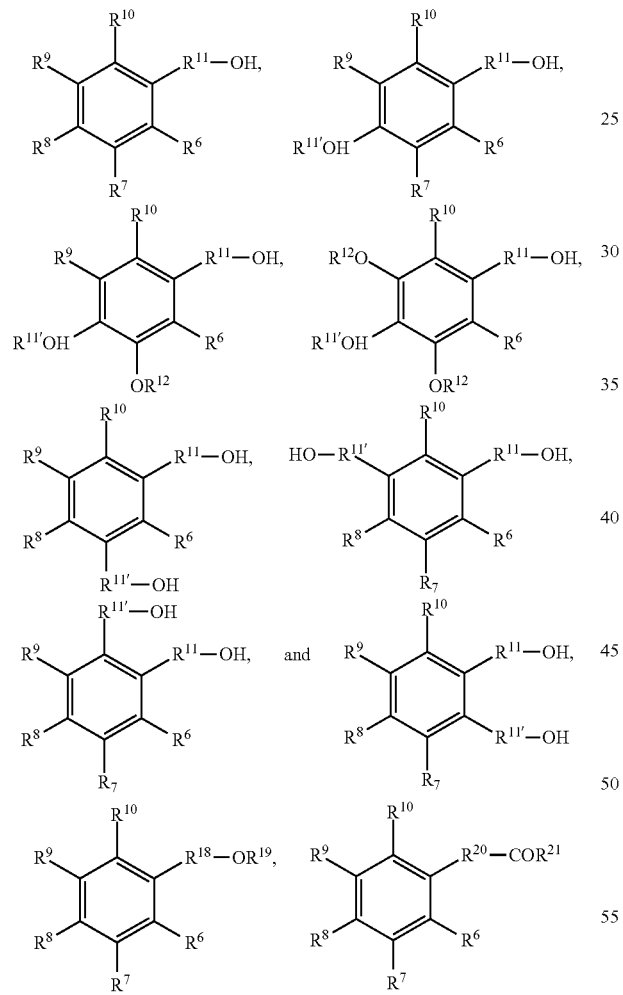

wherein $R^{11'}$ is a bond, substituted or unsubstituted $C_1$-$C_6$ alkyl, $C_2$-$C_{10}$ alkenyl, and Ar"; and wherein $R^{11'}$ and $R^{11}$ are the same or different.

Aspect 6: The method of Aspect 5, wherein $R^{11'}$ and $R^{11}$ are not the same.

Aspect 7: The method of any one of Aspects 1-6, wherein $R^1$ is hydrogen, OH, O−, halogen, or optionally substituted amine, alkyl, aryl, alkoxy, or aryloxy.

Aspect 8: The method of any one of Aspects 1-7, wherein $R^3$ and $R^4$ combine together with the atoms to which they are attached to form an aryl or heteroaryl.

Aspect 9: The method of any one of Aspects 1-8, wherein $R^3$ and $R^4$ are both hydrogen.

Aspect 10: The method of any one of Aspects 1-9, wherein M is Ru or Ir.

Aspect 11: The method of any one of Aspects 1-10, wherein at least one L is Cl, Br, $CH_3CN$, DMF, $H_2O$, bipyridine or phenylpyridine.

Aspect 12: The method of any one of Aspects 1-11, wherein the catalyst is

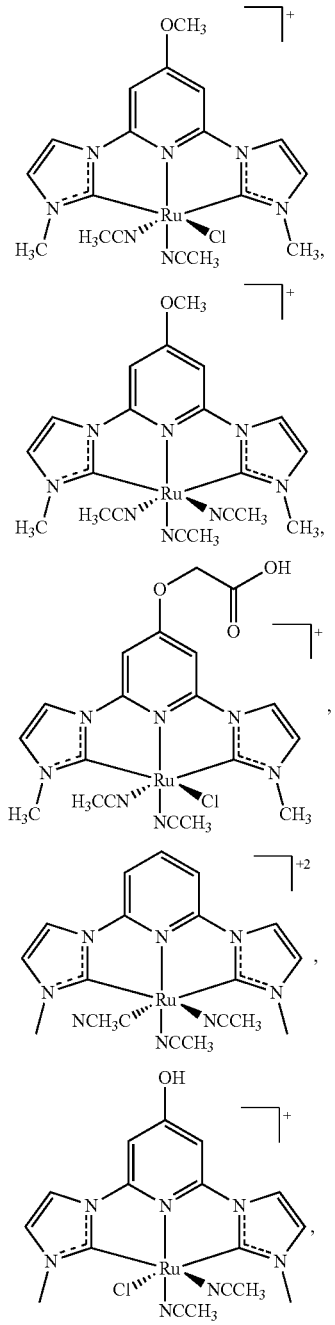

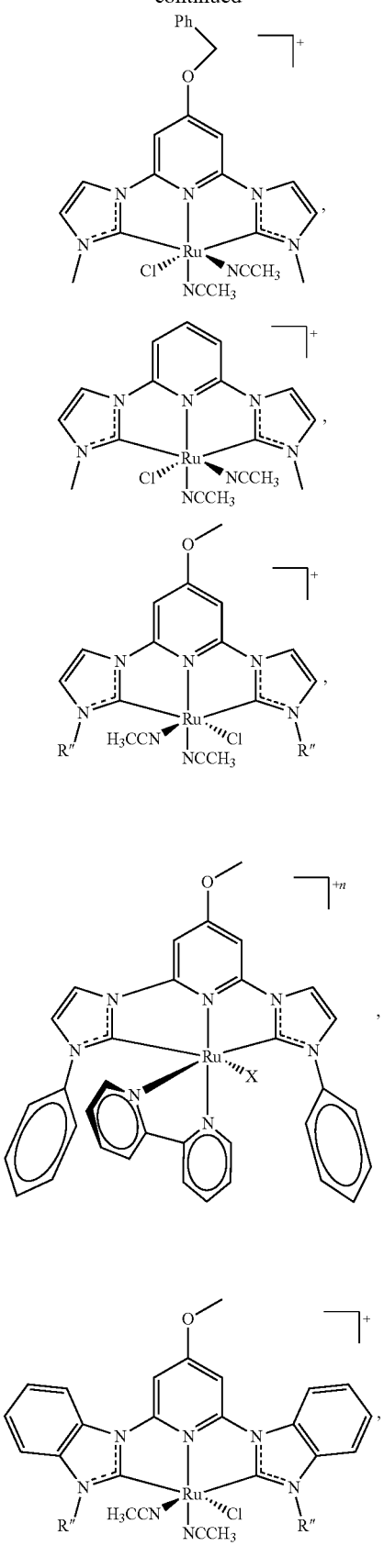
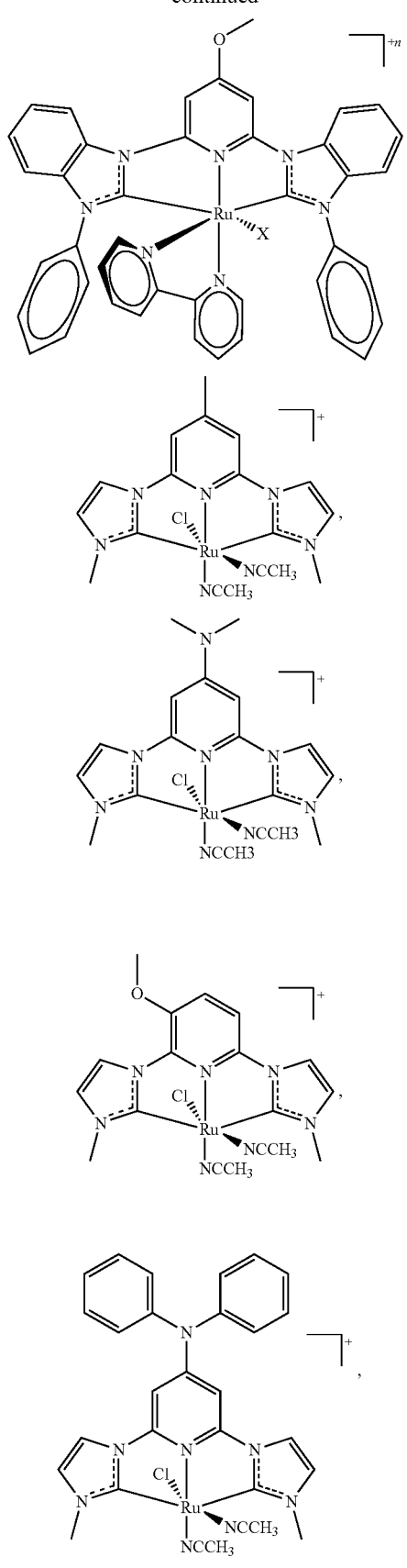

-continued

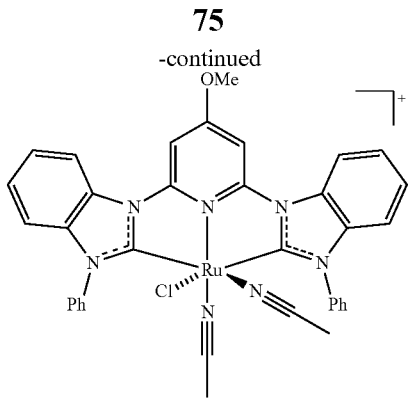

wherein R" is methyl or phenyl, and X is Cl, Br, or CH$_3$CN, wherein n=1 when X is Cl or Br and n=2 when X is CH$_3$CN.

Aspect 13: The method of any one of Aspects 1-12, further comprising one or more counteranions selected from I$^-$, Br$^-$, CF$_3$COO$^-$, BF$_4^-$, OTf$^-$, or PF$_6^-$.

Aspect 14: The method of any one of Aspects 1-13, wherein the catalyst system further comprises an external acid or base.

Aspect 15: The method of any one of Aspects 1-14, wherein the catalyst system does not comprise an external acid.

Aspect 16: The method of Aspect 14 or 15, wherein the base comprises an inorganic base or organic base.

Aspect 17: The method of any one of Aspects 14-16, wherein the base comprises a strong base, a weak base, or a Lewis base.

Aspect 18: The method of any one of Aspects 3-17, wherein the reaction product comprises a compound A of formula (III)

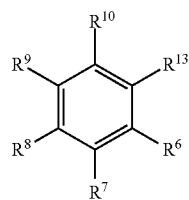
(III)

wherein R$^{13}$ is R$^{11}$—H.

Aspect 19: The method of Aspect 18, wherein when the aromatic compound of formula (II) is selected from

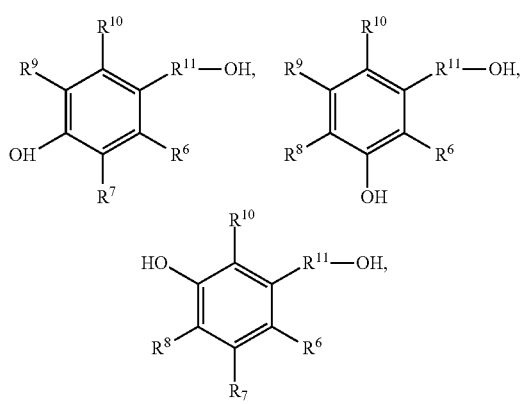

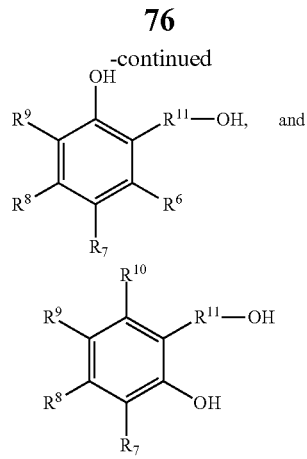

the compound A comprises:

[structures shown]

Aspect 20: The method of any one of Aspects 3-19, wherein the reaction product further comprises a compound B of formula (IV):

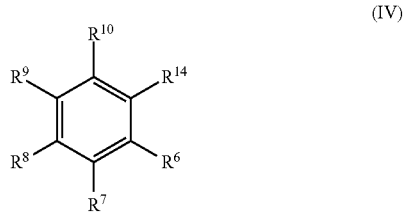
(IV)

wherein R$^{14}$ is —OR$^{15}$, wherein R$^{15}$ is C$_1$-C$_{10}$ alkyl.

Aspect 21: The method of Aspect 20, wherein when the aromatic compound of formula (II) is selected from

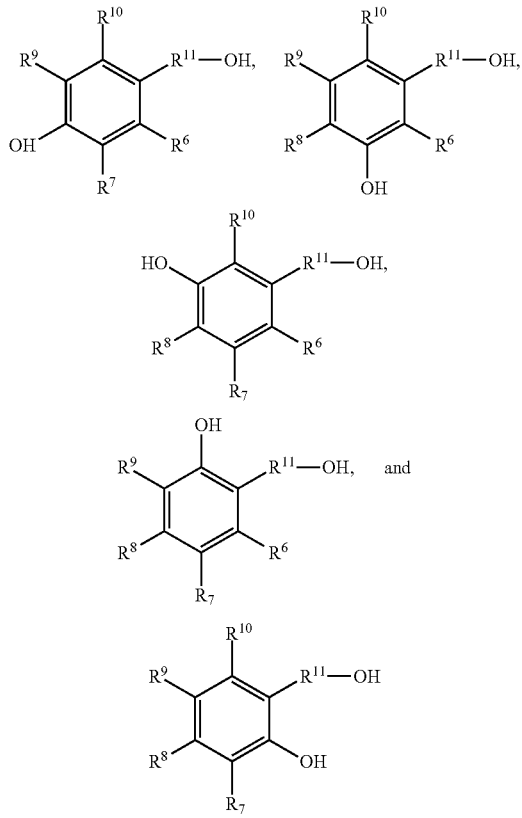

the compound B comprises:

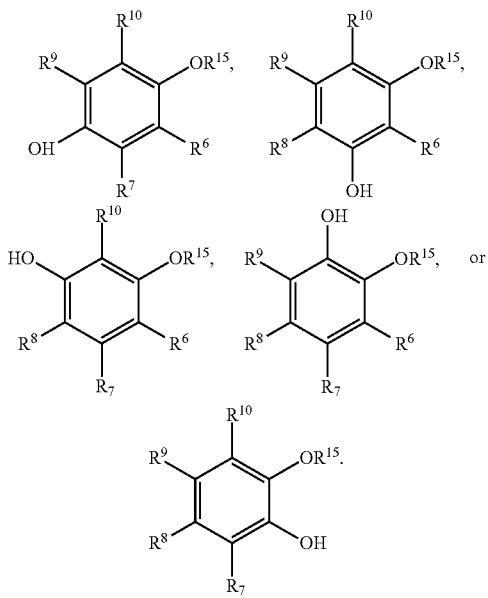

Aspect 22: The method of any one of Aspects 19-21, wherein the compound A is selectively formed over the compound B.

Aspect 23: The method of any one of Aspects 19-22, wherein the selectivity of the compound A is from about 50% to 100%.

Aspect 24: The method of any one of Aspects 19-23, wherein the compound A has a yield from about 50% to 100%.

Aspect 25: The method of Aspect 24, wherein the compound A has a yield from about 85% to 100%.

Aspect 26: The method of Aspect 23, wherein the selectivity of the compound A is from about 85% to 100%.

Aspect 27: The method of any one of Aspects 1-24, wherein the catalyst is present in an amount of greater than 0 mol % to about 1.5 mol %.

Aspect 28: The method of any one of Aspects 14-27, wherein the base is present in an amount from about 50 mol % to 100 mol %.

Aspects 29: A catalyst of formula (I):

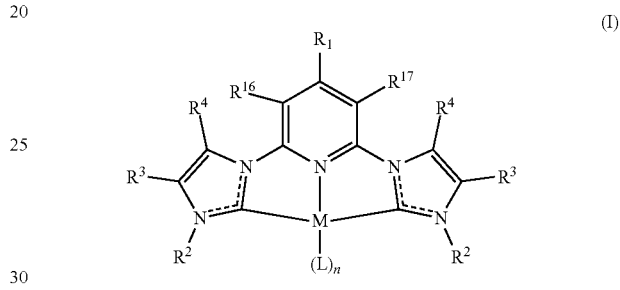

(I)

wherein, $R^1$ is hydrogen, OH, O⁻, halogen, amine, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, $C_6$-$C_{14}$ aryloxy, $C_3$-$C_{10}$ cycloalkyl, or $C_3$-$C_{10}$ cycloalkenyl, wherein $R^1$ is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl;

each $R^2$ is, independent of the other, $C_1$-$C_{10}$ alkyl, $C_2$-$C_{10}$ alkenyl, $C_2$-$C_{10}$ alkynyl, $C_6$-$C_{14}$ aryl, or $C_1$-$C_{13}$ heteroaryl, wherein $R^2$ is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, or thiol, each $R^3$ and $R^4$ are, independent of the other, hydrogen, $C_1$-$C_{10}$ alkyl, $C_2$-$C_{10}$ alkenyl, $C_2$-$C_{10}$ alkynyl, $C_6$-$C_{14}$ aryl, or $C_1$-$C_{13}$ heteroaryl, wherein $R^3$ and $R^4$ are optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, or thiol, or $R^3$ and $R^4$ combine together with the atoms to which they are attached to form a cycloalkyl, cycloheteroaryl, aryl, or heteroaryl;

each $R^{16}$ and $R^{17}$ are, independent of the other, hydrogen, OH, O⁻, halogen, amine, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, $C_6$-$C_{14}$ aryloxy, $C_3$-$C_{10}$ cycloalkyl, or $C_3$-$C_{10}$ cycloalkenyl, wherein each $R^{16}$ and $R_{15}$, independent of the other, is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl;

M is Ru or Ir;

each L is independently selected from Cl, Br, $CH_3CN$, DMF, $H_2O$, bipyridine, phenylpyridine, $CO_2$, and a CNC-pincer ligand; and n is 1, 2, or 3.

Aspect 30: The catalyst of Aspect 29, selected from

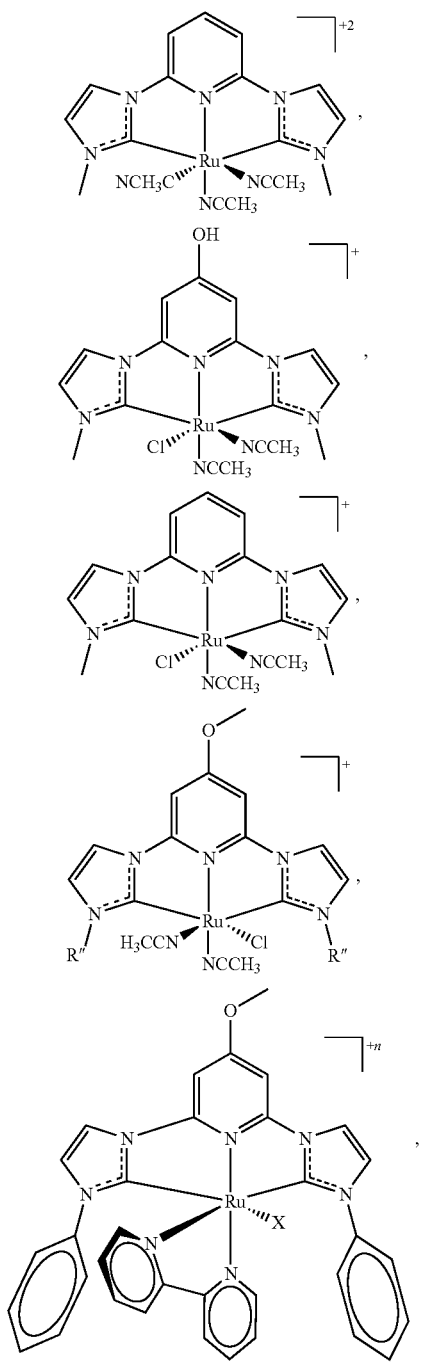

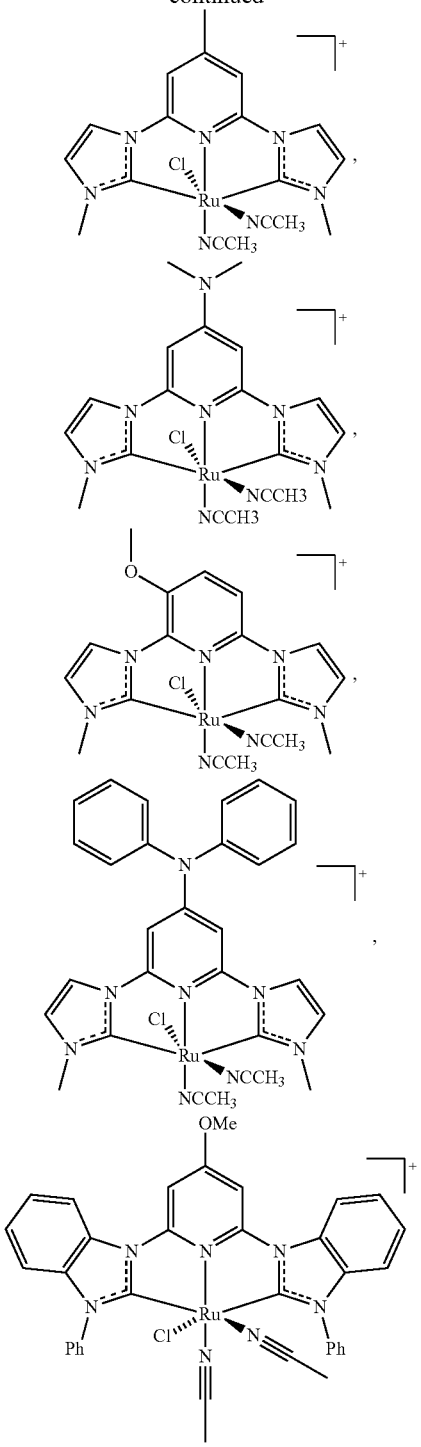

wherein R" is methyl or phenyl, and X is Cl, Br, or $CH_3CN$, wherein n=1 when X is Cl or Br, and n=2 when X is $CH_3CN$.

The invention claimed is:

1. A method comprising:
   selectively deoxygenating at least one oxygenated aromatic compound in the presence of a hydrogen gas and a catalyst system to form a reaction product, wherein the catalyst system comprises a complex of formula (I):

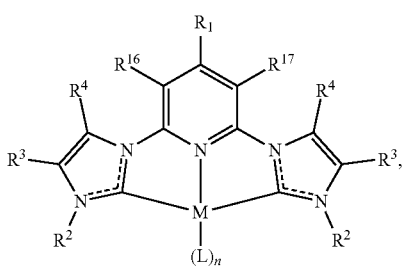

(I)

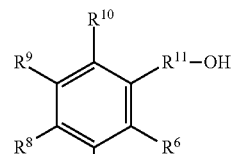

or

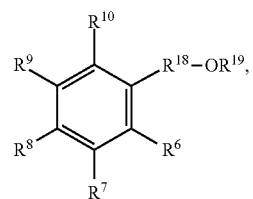

wherein

R¹ is hydrogen, OH, halogen, amine, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, $C_6$-$C_{14}$ aryloxy, $C_3$-$C_{10}$ cycloalkyl, or $C_3$-$C_{10}$ cycloalkenyl, wherein R¹ is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl;

each R² is, independent of the other, $C_1$-$C_{10}$ alkyl, $C_2$-$C_{10}$ alkenyl, $C_2$-$C_{10}$ alkynyl, $C_6$-$C_{14}$ aryl, or $C_1$-$C_{13}$ heteroaryl, wherein R² is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, or thiol;

each R³ and R⁴ are, independent of the other, hydrogen, $C_1$-$C_{10}$ alkyl, $C_2$-$C_{10}$ alkenyl, $C_2$-$C_{10}$ alkynyl, $C_6$-$C_{14}$ aryl, or $C_1$-$C_{13}$ heteroaryl, wherein R³ and R⁴ are optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, or thiol, or R³ and R⁴ combine together with the atoms to which they are attached to form a cycloalkene ring, heteroaromatic ring, or aromatic ring;

each $R^{16}$ and $R^{17}$ are, independent of the other, hydrogen, OH, halogen, amine, $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, $C_6$-$C_{14}$ aryloxy, $C_3$-$C_{10}$ cycloalkyl, or $C_3$-$C_{10}$ cycloalkenyl, wherein each $R^{16}$ and $R_{15}$, independent of the other, is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl;

M is Ru or Ir;

each L is independently selected from $C_1$, Br, $CH_3CN$, DMF, $H_2O$, bipyridine, phenylpyridine, $CO_2$, and a CNC-pincer ligand; and n is 1, 2, or 3;

wherein the oxygenated aromatic compound has the formula:

wherein

R⁶ is independently selected from hydrogen, substituted or unsubstituted $C_1$-$C_6$-alkyl, substituted or unsubstituted $C_3$-$C_{10}$ cycloalkyl and heteroalkyl, $C_2$-$C_{10}$ alkenyl, and Ar';

R⁷ is independently selected from hydrogen, substituted or unsubstituted $C_1$-$C_6$-alkyl, substituted or unsubstituted $C_3$-$C_{10}$ cycloalkyl and heteroalkyl, $C_2$-$C_{10}$ alkenyl, and Ar';

R⁸ is independently selected from hydrogen, substituted or unsubstituted $C_1$-$C_6$-alkyl, substituted or unsubstituted $C_3$-$C_{10}$ cycloalkyl and heteroalkyl, $C_2$-$C_{10}$ alkenyl, and Ar';

R⁹ is independently selected from hydrogen, substituted or unsubstituted $C_1$-$C_6$-alkyl, substituted or unsubstituted $C_3$-$C_{10}$ cycloalkyl and heteroalkyl, $C_2$-$C_{10}$ alkenyl, and Ar';

$R^{10}$ is independently selected from hydrogen, substituted or unsubstituted $C_1$-$C_6$-alkyl; substituted or unsubstituted $C_3$-$C_{10}$ cycloalkyl and heteroalkyl, $C_2$-$C_{10}$ alkenyl, and Ar';

wherein $R^{11}$ is a bond, substituted or unsubstituted $C_1$-$C_6$ alkylene, $C_2$-$C_{10}$ alkenylene, or Ar";

$R^{18}$ is independently selected from substituted or unsubstituted $C_1$-$C_6$-alkylene, $C_2$-$C_{10}$ alkenylene, and Ar";

$R^{19}$ is independently selected from substituted or unsubstituted $C_1$-$C_6$-alkyl, substituted or unsubstituted $C_3$-$C_{10}$ cycloalkyl and heteroalkyl, $C_2$-$C_{10}$ alkenyl, and Ar';

Ar' is a $C_6$-$C_{14}$ aryl or heteroaryl group optionally substituted with 1, 2, or 3 substituents;

Ar" is a $C_6$-$C_{14}$ arylene or heteroarylene group optionally substituted with 1, 2, or 3 substituents;

wherein Ar' and Ar" are the same or different, and wherein the reaction product has the formula:

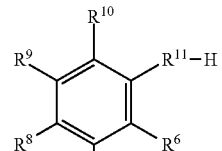

or

-continued

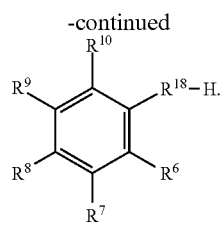

2. The method of claim 1, wherein

R$^6$ is independently selected from hydrogen, substituted or unsubstituted C$_1$-C$_6$-alkyl, substituted or unsubstituted C$_3$-C$_{10}$ cycloalkyl and heteroalkyl, C$_2$-C$_{10}$ alkenyl, and Ar';

R$^7$ is independently selected from hydrogen, substituted or unsubstituted C$_1$-C$_6$-alkyl, substituted or unsubstituted C$_3$-C$_{10}$ cycloalkyl and heteroalkyl, C$_2$-C$_{10}$ alkenyl, and Ar';

R$^8$ is independently selected from hydrogen, substituted or unsubstituted C$_1$-C$_6$-alkyl, substituted or unsubstituted C$_3$-C$_{10}$ cycloalkyl and heteroalkyl, C$_2$-C$_{10}$ alkenyl, and Ar';

wherein R$^9$ is independently selected from hydrogen, substituted or unsubstituted C$_1$-C$_6$-alkyl, substituted or unsubstituted C$_3$-C$_{10}$ cycloalkyl and heteroalkyl, C$_2$-C$_{10}$ alkenyl, and Ar';

R$^{10}$ is independently selected from hydrogen, substituted or unsubstituted C$_1$-C$_6$ alkyl substituted or unsubstituted C$_3$-C$_{10}$ cycloalkyl and heteroalkyl, C$_2$-C$_{10}$ alkenyl, and Ar';

R$^{11}$ is a substituted or unsubstituted C$_1$-C$_6$ alkylene.

3. The method of claim 1, wherein R$^3$ and R$^4$ combined together with the atoms to which they are attached, form an aromatic ring or heteroaromatic ring.

4. The method of claim 1, wherein R$^3$ and R$^4$ are both hydrogen.

5. The method of claim 1, wherein at least one L is Cl, Br, CH$_3$CN, DMF, H$_2$O, bipyridine or phenylpyridine.

6. The method of claim 1, wherein the catalyst is a complex having the formula:

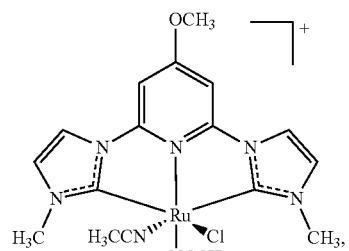

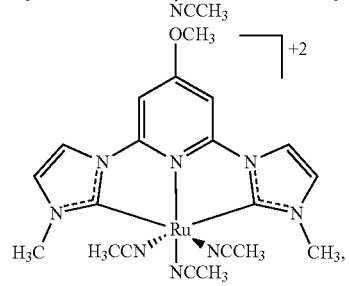

-continued

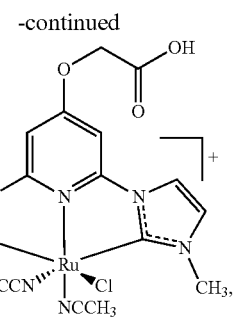

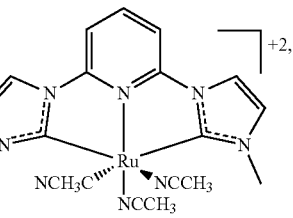

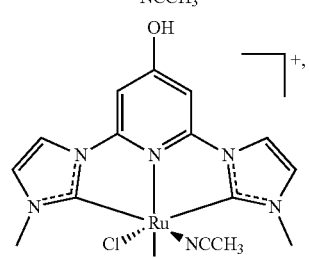

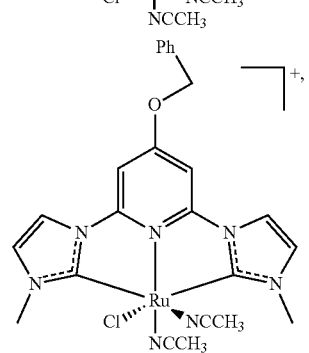

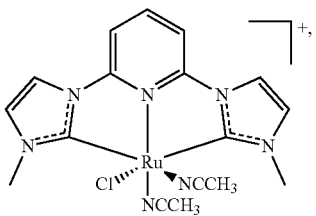

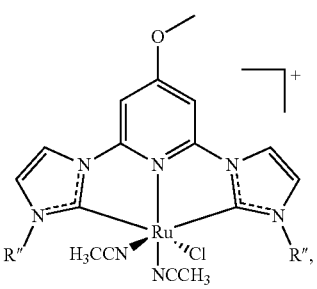

-continued

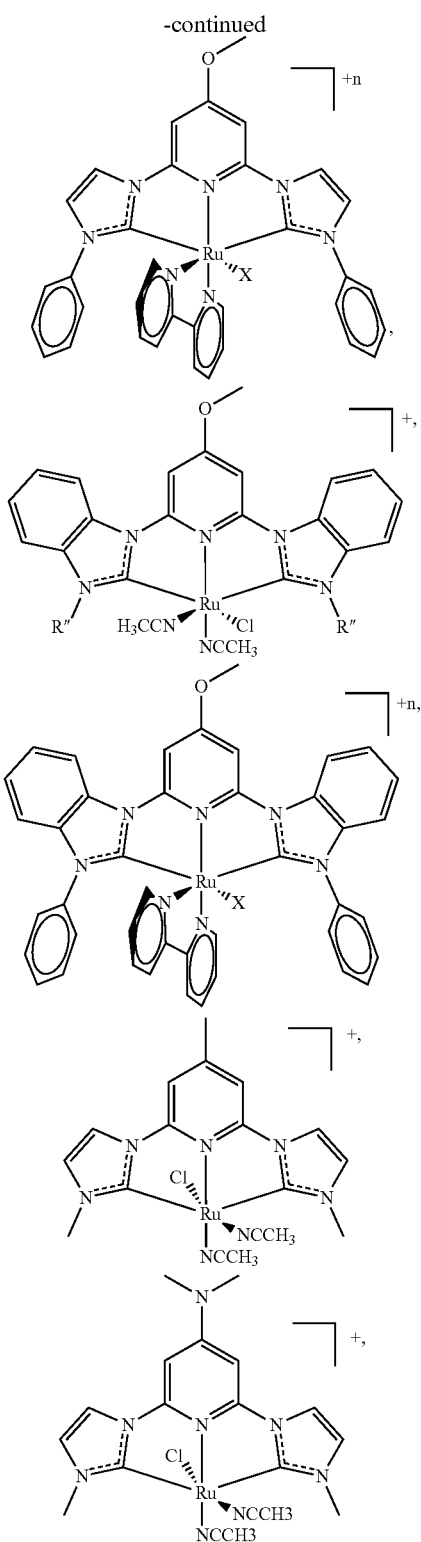

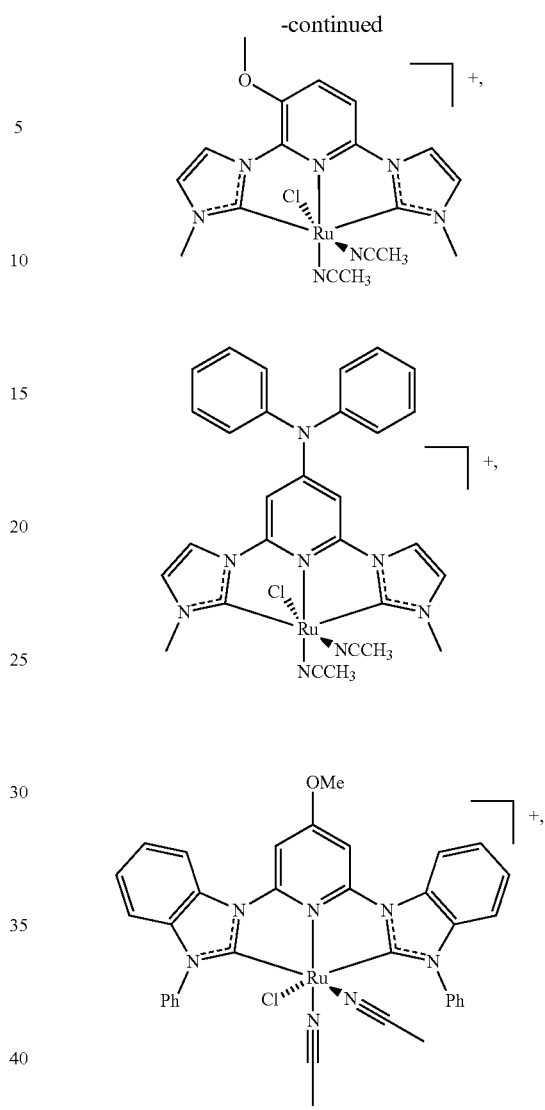

wherein R″ is methyl or phenyl, and X is Cl, Br, or CH₃CN, wherein n=1 when X is Cl or Br and n=2 when X is CH₃CN.

7. The method of claim 6, wherein the catalyst system further comprises one or more counteranions selected from I⁻, Br⁻, CF₃COO⁻, BF₄⁻, OTf⁻, or PF₆⁻.

8. The method of claim 1, wherein the catalyst system further comprises an external acid or base, and wherein when the base is present, the base comprises an inorganic base or organic base in an amount from about 50 mol % to 100 mol %.

9. The method of claim 1, wherein the catalyst system does not comprise an external acid.

10. The method of claim 1, wherein the catalyst is present in an amount of greater than 0 mol % to about 1.5 mol %.

* * * * *